United States Patent
Baker et al.

(10) Patent No.: US 6,228,642 B1
(45) Date of Patent: May 8, 2001

(54) ANTISENSE OLIGONUCLEOTIDE MODULATION OF TUMOR NECROSIS FACTOR-(α) (TNF-α) EXPRESSION

(75) Inventors: Brenda F. Baker; C. Frank Bennett, both of Carlsbad; Madeline M. Butler, Rancho Sante Fe; William R. Shanahan, Jr., Encinitas, all of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/313,932

(22) Filed: May 18, 1999

Related U.S. Application Data

(63) Continuation-in-part of application No. 09/166,186, filed on Oct. 5, 1998, now Pat. No. 6,080,580.

(51) Int. Cl.$^7$ ............................. C07H 21/04; C12Q 1/68; C12N 15/85
(52) U.S. Cl. ............................. 435/375; 435/6; 435/91.1; 435/366; 536/23.1; 536/24.31; 536/24.33; 536/24.5
(58) Field of Search ........................... 435/6, 91.31, 91.1, 435/375, 366; 536/23.1, 23.2, 24.3, 24.5; 514/44

(56) References Cited

U.S. PATENT DOCUMENTS 5,650,316   7/1997   Aggrawal et al. .................... 435/375

FOREIGN PATENT DOCUMENTS

| | | |
|---|---|---|
| 0 414 607 B1 | 8/1990 | (WO) . |
| WO 93/09813 | 5/1993 | (WO) . |
| WO 9402595 * | 2/1994 | (WO) . |
| WO 94/10301 | 5/1994 | (WO) . |
| WO 95/00103 | 1/1995 | (WO) . |
| WO 95/23225 | 8/1995 | (WO) . |
| WO 95/32628 | 12/1995 | (WO) . |
| WO 95/33493 | 12/1995 | (WO) . |
| WO 9710840 * | 9/1996 | (WO) . |
| WO 9710332 * | 3/1997 | (WO) . |

OTHER PUBLICATIONS

Branch, TIBS 23, pp 45–50, Feb. 1998.*
Flanagan et al., Nature Biotech. 17:48–52, Jan. 1999.*
Crook, Basic Principles of Antisense Therapeutics, from *Antisense Research & Application*, pp 1–50, 1998.*
Zou et al., Metabolism, 46(1) 114–8, Jan. 1997.*
Trayhurn et al., FEBS Lett., 368(3) 488–90, Jul. 1995.*
Uhlmann et al., Chem Rev., 90(4) 543–584, Jun. 1990.*
Martin, Helvetica Chemica Acta vol. 78:486–504, 1995.*
Lane et al., Int. J. Obes. Rel. Metals Disord: 20 Suppl 3 p S91–6, Mar. 1996.*
Kiv chgessner et al, J. Clin Invest, 100(4)2777–82, Dec. 1997.*
Aggarwal et al., "Triple Helix–forming Oligodeoxyribonucleotides Targeted to the Human Tumor Necrosis Factor (TNF) Gene Inhibit TNF Production and Block the TNF–dependent Growth of Human Glioblastoma Tumor Cells", 1996, Cancer Res., 56, 5156–5164.
dHellencourt, "Inhibition of human TNFα and LT in cell–free extracts and in cell culture by antisense oligonucleotides", 1996, Biochim. Biophys. Acta, 1317, 168–174.
Hartmann, "Oligodeoxynucleotides Enhance Lipopolysaccharide–Stimulated Synthesis of Tumor Necrosis Factor: Dependence on Phosphorothioate Modification and Reversal by Heparin", 1996, Mol. Med., 2, 429–438.
Hartmann, "Specific Suppression of Human Tumor Necrosis Factor–α Synthesis by Antisense Oligodeoxynucleotides", 1996, Antisense Nucleic Acid Drug Devel., 6, 291–299.
Rojanasakul, "Antisense Inhibition of Silica–induced Tumor Necrosis Factor in Alveolar macrophanges", 1997, J. Biol.Chem., 272, 3910–3914.
Taylor et al., "In Vitro Efficacy of Morpholino–modified Antisense Oligomers Directed against Tumor Necrosis Factor–α mRNA", 1998, Antisense Nucleic Acid Drug Devel., 8, 199–205.
Taylor et al., "Effect of TNF–α Antisense Oligomers on Cytokine Production by Primary Murine Alveolar macrophages", 1996, J. Biol. Chem., 271, 17445–17452.
Tu et al., "Tetranucleotide GGGA Motif in Primary RNA Transcripts", 1998, J. Biol. Chem., 273, 25125–25131.

* cited by examiner

*Primary Examiner*—Robert A. Schwartzman
*Assistant Examiner*—M Schmidt
(74) *Attorney, Agent, or Firm*—Licata & Tyrrell P.C.

(57) ABSTRACT

Compositions and methods are provided for inhibiting the expression of human tumor necrosis factor-α (TNF-α). Antisense oligonucleotides targeted to nucleic acids encoding TNF-α are preferred. Methods of using these oligonucleotides for inhibition of TNF-α expression and for treatment of diseases, particularly inflammatory and autoimmune diseases, associated with overexpression of TNF-α are provided.

14 Claims, No Drawings

ANTISENSE OLIGONUCLEOTIDE MODULATION OF TUMOR NECROSIS FACTOR-(α) (TNF-α) EXPRESSION

INTRODUCTION

This application is a continuation-in-part of U.S. application Ser. No. 09/166,186 filed Oct. 5, 1998, now U.S. Pat. No. 6,080,580.

FIELD OF THE INVENTION

This invention relates to compositions and methods for modulating expression of the human tumor necrosis factor-α (TNF-α) gene, which encodes a naturally present cytokine involved in regulation of immune function and implicated in infectious and inflammatory disease. This invention is also directed to methods for inhibiting TNF-α mediated immune responses; these methods can be used diagnostically or therapeutically. Furthermore, this invention is directed to treatment of conditions associated with expression of the human TNF-α gene.

BACKGROUND OF THE INVENTION

Tumor necrosis factor α (TNF-α also cachectin) is an important cytokine that plays a role in host defense. The cytokine is produced primarily in macrophages and monocytes in response to infection, invasion, injury, or inflammation. Some examples of inducers of TNF-α include bacterial endotoxins, bacteria, viruses, lipopolysaccharide (LPS) and cytokines including GM-CSF, IL-1, IL-2 and IFN-γ.

TNF-α interacts with two different receptors, TNF receptor I (TNFRI, p55) and TNFRII (p75), in order to transduce its effects, the net result of which is altered gene expression. Cellular factors induced by TNF-α include interleukin-1 (IL-1), interleukin-6 (IL-6), interleukin-8 (IL-8), interferon-γ (IFN-γ), platelet derived growth factor (PDGF) and epidermal growth factor (EGF), and endothelial cell adhesion molecules including endothelial leukocyte adhesion molecule 1 (ELAM-1), intercellular adhesion molecule-1 (ICAM-1) and vascular cell adhesion molecule-1 (VCAM-1) (Tracey, K. J., et al., *Annu. Rev. Cell Biol.*, 1993, 9, 317–343; Arvin, B., et al., *Ann. NY Acad. Sci.*, 1995, 765, 62–71).

Despite the protective effects of the cytokine, overexpression of TNF-α often results in disease states, particularly in infectious, inflammatory and autoimmune diseases. This process may involve the apoptotic pathways (Ksontini, R., et al., *J. Immunol.*, 1998, 160, 4082–4089). High levels of plasma TNF-α have been found in infectious diseases such as sepsis syndrome, bacterial meningitis, cerebral malaria, and AIDS; autoimmune diseases such as rheumatoid arthritis, inflammatory bowel disease (including Crohn's disease), sarcoidosis, multiple sclerosis, Kawasaki syndrome, graft-versus-host disease and transplant (allograft) rejection; and organ failure conditions such as adult respiratory distress syndrome, congestive heart failure, acute liver failure and myocardial infarction (Eigler, A., et al., *Immunol. Today,* 1997, 18, 487–492). Other diseases in which TNF-α is involved include asthma (Shah, A., et al., *Clinical and Experimental Allergy*, 1995, 25, 1038–1044), brain injury following ischemia (Arvin, B., et al., *Ann. NY Acad. Sci.*, 1995, 765, 62–71), non-insulin-dependent diabetes mellitus (Hotamisligil, G. S., et al., *Science,* 1993, 259, 87–90), insulin-dependent diabetes mellitus (Yang, X.-D., et al., *J. Exp. Med.*, 1994, 180, 995–1004), hepatitis (Ksontini, R., et al., *J. Immunol.*, 1998, 160, 4082–4089), atopic dermatitis (Sumimoto, S., et al., *Arch. Dis. Child.*, 1992, 67, 277–279), and pancreatitis (Norman, J. G., et al., *Surgery,* 1996, 120, 515–521). Further, inhibitors of TNF-α have been suggested to be useful for cancer prevention (Suganuma, M., et al. (*Cancer Res.*, 1996, 56, 3711–3715). Elevated TNF-α expression may also play a role in obesity (Kern, P. A., *J. Nutr.*, 1997, 127, 1917S–1922S). TNF-α was found to be expressed in human adipocytes and increased expression, in general, correlated with obesity.

There are currently several approaches to inhibiting TNF-α expression. Approaches used to treat rheumatoid arthritis include a chimeric anti-TNF-α antibody, a humanized monoclonal anti-TNF-α antibody, and recombinant human soluble TNF-α receptor (Camussi, G., *Drugs,* 1998, 55, 613–620). Other examples are indirect TNF-α inhibitors including phosphodiesterase inhibitors (e.g. pentoxifylline) and metalloprotease inhibitors (Eigler, A., et al., *Immunol. Today,* 1997, 18, 487–492). An additional class of direct TNF-α inhibitors is oligonucleotides, including triplex-forming oligonucleotides, ribozymes, and antisense oligonucleotides.

Several publications describe the use of oligonucleotides targeting TNF-α by non-antisense mechanisms. U.S. Pat. No. 5,650,316, WO 95/33493 and Aggarwal, B. B. et al. (*Cancer Research,* 1996, 56, 5156–5164) disclose triplex-forming oligonucleotides targeting TNF-α. WO 95/32628 discloses triplex-forming oligonucleotides especially those possessing one or more stretches of guanosine residues capable of forming secondary structure. WO 94/10301 discloses ribozyme compounds active against TNF-α mRNA. WO 95/23225 discloses enzymatic nucleic acid molecules active against TNF-α mRNA.

A number of publications have described the use of antisense oligonucleotides targeting nucleic acids encoding TNF-α. The TNF-α gene has four exons and three introns. WO 93/09813 discloses TNF-α antisense oligonucleotides conjugated to a radioactive moiety, including sequences targeted to the 5'-UTR, AUG start site, exon 1, and exon 4 including the stop codon of human TNF-α. EP 0 414 607 B1 discloses antisense oligonucleotides targeting the AUG start codon of human TNF-α. WO 95/00103 claims antisense oligonucleotides to human TNF-α including sequences targeted to exon 1 including the AUG start site. Hartmann, G. et al. (*Mol. Med.,* 1996, 2, 429–438) disclose uniform phosphorothioates and mixed backbone phosphorothioate/ phosphodiester oligonucleotides targeted to the AUG start site of human TNF-α. Hartmann, G. et al. (*Antisense Nucleic Acid Drug Devel.*, 1996, 6, 291–299) disclose antisense phosphorothioate oligonucleotides targeted to the AUG start site, the exon 1/intron 1 junction, and exon 4 of human TNF-α. d'Hellencourt, C. F. et al. (*Biochim. Biophys. Acta,* 1996, 1317, 168–174) designed and tested a series of unmodified oligonucleotides targeted to the 5'-UTR, and exon 1, including the AUG start site, of human TNF-α. Additionally, one oligonucleotide each was targeted to exon 4 and the 3'-UTR of human TNF-α and one oligonucleotide was targeted to the AUG start site of mouse TNF-α. Rojanasakul, Y. et al. (*J. Biol. Chem.*, 1997, 272, 3910–3914) disclose an antisense phosphorothioate oligonucleotide targeted to the AUG start site of mouse TNF-α. Taylor, M. F. et al. (*J. Biol. Chem.*, 1996, 271, 17445–17452 and *Antisense Nucleic Acid Drug Devel.*, 1998, 8, 199–205) disclose morpholino, methylmorpholino, phosphodiester and phosphorothioate oligonucleotides targeted to the 5'-UTR and AUG start codon of mouse TNF-α. Tu, G.-C. et al. (*J. Biol. Chem.*, 1998, 273, 25125–25131) designed and tested 42 phosphorothioate oligonucleotides targeting sequences throughout the rat TNF-α gene.

Interestingly, some phosphorothioate oligodeoxynucleotides have been found to enhance lipopolysaccharide-stimulated TNF-α synthesis up to four fold due to nonspecific immunostimulatory effects (Hartmann et al. *Mol. Med.,* 1996, 2, 429–438).

Accordingly, there remains an unmet need for therapeutic compositions and methods for inhibiting expression of TNF-α, and disease processes associated therewith.

BRIEF DESCRIPTION OF THE INVENTION

The present invention provides oligonucleotides which are targeted to nucleic acids encoding TNF-α and are capable of modulating TNF-α expression. The present invention also provides chimeric oligonucleotides targeted to nucleic acids encoding human TNF-α. The oligonucleotides of the invention are believed to be useful both diagnostically and therapeutically, and are believed to be particularly useful in the methods of the present invention.

The present invention also comprises methods of modulating the expression of human TNF-α, in cells and tissues, using the oligonucleotides of the invention. Methods of inhibiting TNF-α expression are provided; these methods are believed to be useful both therapeutically and diagnostically. These methods are also useful as tools, for example, for detecting and determining the role of TNF-α in various cell functions and physiological processes and conditions and for diagnosing conditions associated with expression of TNF-α.

The present invention also comprises methods for diagnosing and treating infectious and inflammatory diseases, particularly diabetes, rheumatoid arthritis, Crohn's disease, pancreatitis, multiple sclerosis, atopic dermatitis and hepatitis. These methods are believed to be useful, for example, in diagnosing TNF-α-associated disease progression. These methods employ the oligonucleotides of the invention. These methods are believed to be useful both therapeutically, including prophylactically, and as clinical research and diagnostic tools.

DETAILED DESCRIPTION OF THE INVENTION

TNF-α plays an important regulatory role in the immune response to various foreign agents. Overexpression of TNF-α results in a number of infectious and inflammatory diseases. As such, this cytokine represents an attractive target for treatment of such diseases. In particular, modulation of the expression of TNF-α may be useful for the treatment of diseases such as Crohn's disease, diabetes mellitus, multiple sclerosis, rheumatoid arthritis, hepatitis, pancreatitis and asthma.

The present invention employs antisense compounds, particularly oligonucleotides, for use in modulating the function of nucleic acid molecules encoding TNF-α, ultimately modulating the amount of TNF-α produced. This is accomplished by providing oligonucleotides which specifically hybridize with nucleic acids, preferably mRNA, encoding TNF-α.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding TNF-α; in other words, a gene encoding TNF-α, or mRNA expressed from the TNF-α gene. mRNA which encodes TNF-α is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding TNF-α, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNAs. The remaining (and therefore translated) regions are known as "exons" and are spliced together to form a continuous mRNA sequence. mRNA splice sites, i.e., exon—exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of TNF-α. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects of antisense oligonucleotides of the present invention on TNF-α expression can also be determined as taught in the examples of the instant application. Inhibition is presently a preferred form of modulation.

The oligonucleotides of this invention can be used in diagnostics, therapeutics, prophylaxis, and as research reagents and in kits. Since the oligonucleotides of this invention hybridize to nucleic acids encoding TNF-α, sandwich, colorimetric and other assays can easily be constructed to exploit this fact. Provision of means for detecting hybridization of oligonucleotides with the TNF-α gene or mRNA can routinely be accomplished. Such provision may include enzyme conjugation, radiolabelling or any other suitable detection systems. Kits for detecting the presence or absence of TNF-α may also be prepared.

The present invention is also suitable for diagnosing abnormal inflammatory states in tissue or other samples from patients suspected of having an inflammatory disease such as rheumatoid arthritis. The ability of the oligonucleotides of the present invention to inhibit inflammatory processes may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262. Further teaching of PNA compounds can be found in Nielsen et al. (*Science,* 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$O——N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Crooke, S. T. and Lebleu, B., eds., *Antisense Research and Applications* 1993, CRC Press, Boca Raton, pages 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. No. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH$)$_3$ modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; © salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. I n contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the compositions of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents such as those used for tumor and cancer treatment. When used with the compounds of the invention, such chemotherapeutic agents may be used individually, sequentially, or in combination with one or more other such chemotherapeutic agents.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (*J. Med. Chem.* 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies. Standard methods are also used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (*Helv. Chim. Acta* 1995, 78, 486–506). For ease of synthesis, the last nucleotide may be a deoxynucleotide. 2'-O—CH$_2$CH$_2$OCH$_3$-cytosines may be 5-methyl cytosines.

Synthesis of 5-Methyl cytosine monomers:

2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine

2'-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

Oligonucleotides having methylene(methylimino) (MMI) backbones were synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Example 2

Human TNF-α Oligodeoxynucleotide Sequences

Antisense oligonucleotides were designed to target human TNF-α. Target sequence data are from the TNF-α cDNA sequence published by Nedwin, G. E. et al. (*Nucleic Acids Res.* 1985, 13, 6361–6373); Genbank accession number X02910, provided herein as SEQ ID NO: 1. Oligodeoxynucleotides were synthesized primarily with phosphorothioate linkages. Oligonucleotide sequences are shown in Table 1. Oligonucleotide 14640 (SEQ ID NO. 2) is a published TNF-α antisense oligodeoxynucleotide targeted to the start site of the TNF-α gene (Hartmann, G., et al., *Antisense Nucleic Acid Drug Dev.,* 1996, 6, 291–299). Oligonucleotide 2302 (SEQ ID NO. 41) is an antisense oligodeoxynucleotide targeted to the human intracellular adhesion molecule-1 (ICAM-1) and was used as an unrelated (negative) target control. Oligonucleotide 13664 (SEQ ID NO. 42) is an antisense oligodeoxynucleotide targeted to the Herpes Simplex Virus type 1 and was used as an unrelated target control.

NeoHK cells, human neonatal foreskin keratinocytes (obtained from Cascade Biologicals, Inc., Portland, Oreg.) were cultured in Keratinocyte medium containing the supplied growth factors (Life Technologies, Rockville, Md.).

At assay time, the cells were between 70% and 90% confluent. The cells were incubated in the presence of Keratinocyte medium, without the supplied growth factors added, and the oligonucleotide formulated in LIPOFECTIN® (Life Technologies), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. For an initial screen, the oligonucleotide concentration was 300 nM in 9 μg/mL LIPOFECTIN®. Treatment was for four hours. After treatment, the medium was removed and the cells were further incubated in Keratinocyte medium containing the supplied growth factors and 100 nM phorbol 12-myristate 13-acetate (PMA, Sigma, St. Louis, Mo.). mRNA was analyzed 2 hours post-induction with PMA. Protein levels were analyzed 12 to 20 hours post-induction.

Total mRNA was isolated using the RNEASY® Mini Kit (Qiagen, Valencia, Calif.; similar kits from other manufacturers may also be used), separated on a 1% agarose gel, transferred to HYBOND™N+ membrane (Amersham Pharmacia Biotech, Piscataway, N.J.), a positively charged nylon membrane, and probed. A TNF-α probe consisted of the 505 bp EcoRI-HindIII fragment from BBG 18 (R&D Systems, Minneapolis, Minn.), a plasmid containing human TNF-α cDNA. A glyceraldehyde 3-phosphate dehydrogenase (G3PDH) probe consisted of the 1.06 kb HindIII fragment from pHcGAP (American Type Culture Collection, Manassas, Va.), a plasmid containing human G3PDH cDNA. The restriction fragments were purified from low-melting temperature agarose, as described in Maniatis, T., et al., *Molecular Cloning: A Laboratory Manual,* 1989 and labeled with REDIVUE™ $^{32}$P-dCTP (Amersham Pharmacia Biotech, Piscataway, N.J.) and PRIME-A-GENE® labeling kit (Promega, Madison, Wis.). mRNA was quantitated by a PhosphoImager (Molecular Dynamics, Sunnyvale, Calif.).

Secreted TNF-α protein levels were measured using a human TNF-α ELISA kit (R&D Systems, Minneapolis, Minn. or Genzyme, Cambridge, Mass.).

TABLE 1

Nucleotide Sequences of Human TNF-α
Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 14640 | CATGCTTTCAGTGCTCAT | 2 | 0796–0813 | AUG |
| 14641 | TGAGGGAGCGTCTGCTGGCT | 3 | 0615–0634 | 5'-UTR |
| 14642 | GTGCTCATGGTGTCCTTTCC | 4 | 0784–0803 | AUG |
| 14643 | TAATCACAAGTGCAAACATA | 5 | 3038–3057 | 3'-UTR |
| 14644 | TACCCCGGTCTCCCAAATAA | 6 | 3101–3120 | 3'-UTR |
| 14810 | GTGCTCATGGTGTCCTTTCC | 4 | 0784–0803 | AUG |
| 14811 | AGCACCGCCTGGAGCCCT | 7 | 0869–0886 | coding |
| 14812 | GCTGAGGAACAAGCACCGCC | 8 | 0878–0897 | coding |
| 14813 | AGGCAGAAGAGCGTGGTGGC | 9 | 0925–0944 | coding |
| 14814 | AAAGTGCAGCAGGCAGAAGA | 10 | 0935–0954 | coding |

TABLE 1-continued

Nucleotide Sequences of Human TNF-α Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 14815 | TTAGAGAGAGGTCCCTGG | 11 | 1593–1610 | coding |
| 14816 | TGACTGCCTGGGCCAGAG | 12 | 1617–1634 | junction |
| 14817 | GGGTTCGAGAAGATGATC | 13 | 1822–1839 | junction |
| 14818 | GGGCTACAGGCTTGTCACTC | 14 | 1841–1860 | coding |
| 14820 | CCCCTCAGCTTGAGGGTTTG | 15 | 2171–2190 | junction |
| 14821 | CCATTGGCCAGGAGGGCATT | 16 | 2218–2237 | coding |
| 14822 | ACCACCAGCTGGTTATCTCT | 17 | 2248–2267 | coding |
| 14823 | CTGGGAGTAGATGAGGTACA | 18 | 2282–2301 | coding |
| 14824 | CCCTTGAAGAGGACCTGGGA | 19 | 2296–2315 | coding |
| 14825 | GGTGTGGGTGAGGAGCACAT | 20 | 2336–2355 | coding |
| 14826 | GTCTGGTAGGAGACGGCGAT | 21 | 2365–2384 | coding |
| 14827 | GCAGAGAGGAGGTTGACCTT | 22 | 2386–2405 | coding |
| 14828 | GCTTGGCCTCAGCCCCCTCT | 23 | 2436–2455 | coding |
| 14829 | CCTCCCAGATAGATGGGCTC | 24 | 2464–2483 | coding |
| 14830 | CCCTTCTCCAGCTGGAAGAC | 25 | 2485–2504 | coding |
| 14831 | ATCTCAGCGCTGAGTCGGTC | 26 | 2506–2525 | coding |
| 14832 | TCGAGATAGTCGGGCCGATT | 27 | 2527–2546 | coding |
| 14833 | AAGTAGACCTGCCCAGACTC | 28 | 2554–2573 | coding |
| 14834 | GGATGTTCGTCCTCCTCACA | 29 | 2588–2607 | STOP |
| 14835 | ACCCTAAGCCCCCAATTCTC | 30 | 2689–2708 | 3'-UTR |
| 14836 | CCACACATTCCTGAATCCCA | 31 | 2758–2777 | 3'-UTR |
| 14837 | AGGCCCCAGTGAGTTCTGGA | 32 | 2825–2844 | 3'-UTR |
| 14838 | GTCTCCAGATTCCAGATGTC | 33 | 2860–2879 | 3'-UTR |
| 14839 | CTCAAGTCCTGCAGCATTCT | 34 | 2902–2921 | 3'-UTR |
| 14840 | TGGGTCCCCCAGGATACCCC | 35 | 3115–3134 | 3'-UTR |
| 14841 | ACGGAAAACATGTCTGAGCC | 36 | 3151–3170 | 3'-UTR |
| 14842 | CTCCGTTTTCACGGAAAACA | 37 | 3161–3180 | 3'-UTR |
| 14843 | GCCTATTGTTCAGCTCCGTT | 38 | 3174–3193 | 3'-UTR |
| 14844 | GGTCACCAAATCAGCATTGT | 39 | 3272–3292 | 3'-UTR |
| 14845 | GAGGCTCAGCAATGAGTGAC | 40 | 3297–3316 | 3'-UTR |
| 2302 | GCCCAAGCTGGCATCCGTCA | 41 | | target control |
| 13664 | GCCGAGGTCCATGTCGTACGC | 42 | | target control |

[1] "C" residues are 5-methyl-cytosines except "C" residues are unmodified cytidines; all linkages are phosphorothioate linkages.
[2] Co-ordinates from Genbank Accession No. X02910, locus name "HSTNFA", SEQ ID NO. 1.

Results are shown in Table 2. Oligonucleotides 14828 (SEQ ID NO. 23), 14829 (SEQ ID NO. 24), 14832 (SEQ ID NO. 27), 14833 (SEQ ID NO. 28), 14834 (SEQ ID NO. 29), 14835 (SEQ ID NO. 30), 14836 (SEQ ID NO. 31), 14839 (SEQ ID NO. 34), 14840 (SEQ ID NO. 35), and 14844 (SEQ ID NO. 39) inhibited TNF-α expression by approximately 50% or more.

Oligonucleotides 14828 (SEQ ID NO. 23), 14834 (SEQ ID NO. 29), and 14840 (SEQ ID NO. 35) gave better than 70% inhibition.

TABLE 2

Inhibition of Human TNF-α mRNA Expression by Phosphorothioate Oligodeoxynucleotides

| ISIS No.: | SEQ ID NO: | GENE TARGET REGION | % mRNA EXPRESSION | % mRNA INHIBITION |
|---|---|---|---|---|
| basal | — | — | 16% | — |
| induced | — | — | 100% | 0% |
| 13664 | 42 | control | 140% | — |
| 14640 | 2 | AUG | 61% | 39% |
| 14641 | 3 | 5'-UTR | 95% | 5% |
| 14642 | 4 | AUG | 131% | — |
| 14810 | 4 | AUG | 111% | — |
| 14815 | 11 | coding | 85% | 15% |
| 14816 | 12 | junction | 106% | — |
| 14817 | 13 | junction | 97% | 3% |
| 14818 | 14 | coding | 64% | 36% |
| 14820 | 15 | junction | 111% | — |
| 14821 | 16 | coding | 91% | 9% |
| 14822 | 17 | coding | 57% | 43% |
| 14827 | 22 | coding | 67% | 33% |
| 14828 | 23 | coding | 27% | 73% |
| 14829 | 24 | coding | 33% | 67% |
| 14830 | 25 | coding | 71% | 29% |
| 14831 | 26 | coding | 62% | 38% |
| 14832 | 27 | coding | 40% | 60% |
| 14833 | 28 | coding | 43% | 57% |
| 14834 | 29 | STOP | 26% | 74% |
| 14835 | 30 | 3'-UTR | 32% | 68% |
| 14836 | 31 | 3'-UTR | 40% | 60% |
| 14837 | 32 | 3'-UTR | 106% | — |
| 14838 | 33 | 3'-UTR | 70% | 30% |
| 14839 | 34 | 5'-UTR | 49% | 51% |
| 14840 | 35 | 3'-UTR | 28% | 72% |
| 14841 | 36 | 3'-UTR | 60% | 40% |
| 14842 | 37 | 3'-UTR | 164% | — |
| 14843 | 38 | 3'-UTR | 67% | 33% |
| 14844 | 39 | 3'-UTR | 46% | 54% |
| 14845 | 40 | 3'-UTR | 65% | 35% |

Example 3

Dose Response of Antisense Phosphorothioate Oligonucleotide Effects on Human TNF-α mRNA Levels in NeoHK Cells Four of the more active oligonucleotides from the initial screen were chosen for dose response assays. These include oligonucleotides 14828 (SEQ ID NO. 23), 14833 (SEQ ID NO. 28), 14834 (SEQ ID NO. 29) and 14839 (SEQ ID NO. 34). NeoHK cells were grown, treated and processed as described in Example 2. LIPOFECTIN® was added at a ratio of 3 μg/mL per 100 nM of oligonucleotide. The control included LIPOFECTIN® at a concentration of 9 μg/mL. The effect of the TNF-α antisense oligonucleotides was normalized to the non-specific target control. Results are shown in Table 3. Each oligonucleotide showed a dose response effect with maximal inhibition greater than 70%. Oligonucleotides 14828 (SEQ ID NO. 23) had an $IC_{50}$ of approximately 185 nM. Oligonucleotides 14833 (SEQ ID NO. 28) had an $IC_{50}$ of approximately 150 nM. Oligonucleotides 14834 (SEQ ID NO. 29) and 14839 (SEQ ID NO. 34) had an IC$_{50}$ of approximately 140 nM.

TABLE 3

Dose Response of NeoHK Cells to TNF-α
Antisense Phosphorothioate Oligodeoxynucleotides (ASOs)

| ISIS # | SEQ ID NO: | ASO Gene Target | Dose | % mRNA Expression | % mRNA Inhibition |
|---|---|---|---|---|---|
| 2302 | 41 | control | 25 nM | 100% | — |
| " | " | " | 50 nM | 100% | — |
| " | " | " | 100 nM | 100% | — |
| " | " | " | 200 nM | 100% | — |
| " | " | " | 300 nM | 100% | — |
| 14828 | 23 | coding | 25 nM | 122% | — |
| " | " | " | 50 nM | 97% | 3% |
| " | " | " | 100 nM | 96% | 4% |
| " | " | " | 200 nM | 40% | 60% |
| " | " | " | 300 nM | 22% | 78% |
| 14833 | 28 | coding | 25 nM | 89% | 11% |
| " | " | " | 50 nM | 78% | 22% |
| " | " | " | 100 nM | 64% | 36% |
| " | " | " | 200 nM | 36% | 64% |
| " | " | " | 300 nM | 25% | 75% |
| 14834 | 29 | STOP | 25 nM | 94% | 6% |
| " | " | " | 50 nM | 69% | 31% |
| " | " | " | 100 nM | 65% | 35% |
| " | " | " | 200 nM | 26% | 74% |
| " | " | " | 300 nM | 11% | 89% |
| 14839 | 34 | 3'-UTR | 25 nM | 140% | — |
| " | " | " | 50 nM | 112% | — |
| " | " | " | 100 nM | 65% | 35% |

TABLE 3-continued

Dose Response of NeoHK Cells to TNF-α
Antisense Phosphorothioate Oligodeoxynucleotides (ASOs)

| ISIS # | SEQ ID NO: | ASO Gene Target | Dose | % mRNA Expression | % mRNA Inhibition |
|---|---|---|---|---|---|
| " | " | " | 200 nM | 29% | 71% |
| " | " | " | 300 nM | 22% | 78% |

Example 4

Design and Testing of Chimeric (Deoxy Gapped)
2'-O-methoxyethyl TNF-α Antisense
Oligonucleotides on TNF-α Levels in NeoHK Cells Oligonucleotides having SEQ ID NO: 28 and SEQ ID NO: 29 were synthesized as uniformly phosphorothioate or mixed phosphorothioate/phosphodiester chimeric oligonucleotides having variable regions of 2'-O-methoxyethyl (2'-MOE) nucleotides and deoxynucleotides. The sequences and the oligonucleotide chemistries are shown in Table 4. All 2'-MOE cytosines were 5-methyl-cytosines.

Dose response experiments, as discussed in Example 3, were performed using these chimeric oligonucleotides. The effect of the TNF-α antisense oligonucleotides was normalized to the non-specific target control. Results are shown in Table 5. The activities of the chimeric oligonucleotides tested were comparable to the parent phosphorothioate oligonucleotide.

TABLE 4

Nucleotide Sequences of TNF-α
Chimeric (deoxy gapped) 2'-O-methoxyethyl Oligonucleotides

| ISIS NO. | NUCLEOTIDE SEQUENCE (5' ->3') | SEQ ID NO: | TARGET GENE NUCLEOTIDE CO-ORDINATES[1] | GENE TARGET REGION |
|---|---|---|---|---|
| 14833 | AsAsGsTsAsGsAsCsCsTsGsCsCsCsAsGsAsCsTsC | 28 | 2554–2573 | coding |
| 16467 | AoAoGoToAsGsAsCsCsTsGsCsCsCsAsGoAoCoToC | 28 | 2554–2573 | coding |
| 16468 | AsAsGsTsAsGsAsCsCsTsGsCsCsCsAsGsAsCsTsC | 28 | 2554–2573 | coding |
| 16469 | AsAsGsTsAsGsAsCsCsTsGsCsCsCsAsGsAsCsTsC | 28 | 2554–2573 | coding |
| 16470 | AsAsGsTsAsGsAsCsCsTsGsCsCsCsAsGsAsCsTsC | 28 | 2554–2573 | coding |
| 16471 | AsAsGsTsAsGsAsCsCsTsGsCsCsCsAsGsAsCsTsC | 28 | 2554–2573 | coding |
| 14834 | GsGsAsTsGsTsTsCsGsTsCsCsTsCsCsTsCsAsCsA | 29 | 2588–2607 | STOP |
| 16472 | GoGoAoToGsTsTsCsGsTsCsCsTsCsCsTsCoAoCoA | 29 | 2588–2607 | STOP |
| 16473 | GsGsAsTsGsTsTsCsGsTsCsCsTsCsCsTsCsAsCsA | 29 | 2588–2607 | STOP |
| 16474 | GsGsAsTsGsTsTsCsGsTsCsCsTsCsCsTsCsAsCsA | 29 | 2588–2607 | STOP |

TABLE 4-continued

Nucleotide Sequences of TNF-α
Chimeric (deoxy gapped) 2'-O-methoxyethyl Oligonucleotides

| ISIS NO. | NUCLEOTIDE SEQUENCE (5' ->3') | SEQ ID NO: | TARGET GENE NUCLEOTIDE CO-ORDINATES[1] | GENE TARGET REGION |
|---|---|---|---|---|
| 16475 | GsGsAsTsGsTsTsCsGsTsCsCsTsCsCsTsCsAsCsA | 29 | 2588–2607 | STOP |
| 16476 | GsGsAsTsGsTsTsCsGsTsCsCsTsCsCsTsCsAsCsA | 29 | 2588–2607 | STOP |

[1] Emboldened residues are 2'-methoxyethoxy residues (others are 2'-deoxy-). All 2'-methoxyethoxy cytidines are 5-methyl-cytidines; "s" linkages are phosphorothioate linkages, "o" linkages are phosphodiester linkages.
[2] Co-ordinates from Genbank Accession No. X02910, locus name "HSTNFA", SEQ ID NO. 1.

TABLE 5

Dose Response of NeoHK Cells to TNF-α
Chimeric (deoxy gapped) 2'-O-methoxyethyl Antisense Oligonucleotides

| ISIS # | SEQ ID NO: | ASO Gene Target | Dose | % mRNA Expression | % mRNA Inhibition |
|---|---|---|---|---|---|
| 13664 | 42 | control | 50 nM | 100% | — |
| " | " | " | 100 nM | 100% | — |
| " | " | " | 200 nM | 100% | — |
| " | " | " | 300 nM | 100% | — |
| 14833 | 28 | coding | 50 nM | 69% | 31% |
| " | " | " | 100 nM | 64% | 36% |
| " | " | " | 200 nM | 56% | 44% |
| " | " | " | 300 nM | 36% | 64% |
| 16468 | 28 | coding | 50 nM | 66% | 34% |
| " | " | " | 100 nM | 53% | 47% |
| " | " | " | 200 nM | 34% | 66% |
| " | " | " | 300 nM | 25% | 75% |
| 16471 | 28 | coding | 50 nM | 77% | 23% |
| " | " | " | 100 nM | 56% | 44% |
| " | " | " | 200 nM | 53% | 47% |
| " | " | " | 300 nM | 31% | 69% |
| 14834 | 29 | STOP | 50 nM | 74% | 26% |
| " | " | " | 100 nM | 53% | 47% |
| " | " | " | 200 nM | 24% | 76% |
| " | " | " | 300 nM | 11% | 89% |
| 16473 | 29 | STOP | 50 nM | 71% | 29% |
| " | " | " | 100 nM | 51% | 49% |
| " | " | " | 200 nM | 28% | 72% |
| " | " | " | 300 nM | 23% | 77% |
| 16476 | 29 | STOP | 50 nM | 74% | 26% |
| " | " | " | 100 nM | 58% | 42% |
| " | " | " | 200 nM | 32% | 68% |
| " | " | " | 300 nM | 31% | 69% |

Example 5

Design and Testing of Chimeric Phosphorothioate/ MMI TNF-α Antisense Oligodeoxynucleotides on TNF-α Levels in NeoHK Cells Oligonucleotides having SEQ ID NO. 29 were synthesized as mixed phosphorothioate/methylene(methylimino) (MMI) chimeric oligodeoxynucleotides. The sequences and the oligonucleotide chemistries are shown in Table 6. Oligonucleotide 13393 (SEQ ID NO. 49) is an antisense oligonucleotide targeted to the human intracellular adhesion molecule-1 (ICAM-1) and was used as an unrelated target control. All cytosines were 5-methyl-cytosines.

Dose response experiments were performed using these chimeric oligonucleotides, as discussed in Example 3 except quantitation of TNF-α mRNA levels was determined by real-time PCR (RT-PCR) using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents were obtained from PE-Applied Biosystems, Foster City, Calif. RT-PCR reactions were carried out by adding 25 μl PCR cocktail (1× TAQMAN® buffer A, 5.5 mM $MgCl_2$, 300 μM each of dATP, dCTP and dGTP, 600 μM of dUTP, 100 nM each of forward primer, reverse primer, and probe, 20 U RNAse inhibitor, 1.25 units AMPLITAQ GOLD®, and 12.5 U MuLV reverse transcriptase) to 96 well plates containing 25 μl poly(A) mRNA solution. The RT reaction was carried out by incubation for 30 minutes at 48° C. following a 10 minute incubation at 95° C. to activate the AMPLITAQ GOLD®, 40 cycles of a two-step PCR protocol were carried out: 95° C. for 15 seconds (denaturation) followed by 60° C. for 1.5 minutes (annealing/extension).

For TNF-α the PCR primers were:

Forward: 5'-CAGGCGGTGCTTGTTCCT-3' SEQ ID NO. 43

Reverse: 5'-GCCAGAGGGCTGATTAGAGAGA-3' SEQ ID NO. 44 and the PCR probe was: FAM-CTTCTCCTTCCTGATCGTGGCAGGC-TAMRA (SEQ ID NO. 45) where FAM or JOE (PE-Applied Biosystems, Foster City, Calif.) is the fluorescent reporter dye) and TAMRA (PE-Applied Biosystems, Foster City, Calif.) is the quencher dye.

For GAPDH the PCR primers were:

Forward primer: 5'-GAAGGTGAAGGTCGGAGTC-3' SEQ ID NO. 46

Reverse primer: 5'-GAAGATGGTGATGGGATTTC-3' SEQ ID NO. 47 and the PCR probe was: 5' JOE-CAAGCTTCCCGTTCTCAGCC-TAMRA 3' (SEQ ID NO. 48) where FAM or JOE (PE-Applied Biosystems, Foster City, Calif.) is the fluorescent reporter dye) and TAMRA (PE-Applied Biosystems, Foster City, Calif.) is the quencher dye.

Results are shown in Table 7. The oligonucleotide containing MMI linkages was more effective in reducing TNF-α mRNA levels than the uniformly phosphorothioate oligonucleotide. The $IC_{50}$ value was reduced from approximately 75 nM, for oligonucleotide 14834 (SEQ ID NO: 29), to approximately 30 nM for oligonucleotide 16922 (SEQ ID NO: 29).

Dose response experiments were also performed measuring the effect on TNF-α protein levels. Protein levels were measured as described in Example 2. Results are shown in Table 8. The oligonucleotide containing four MMI linkages on each end was more effective in reducing protein levels than the uniformly phosphorothioate oligonucleotide. The $IC_{50}$ value was reduced from approximately 90 nM, for oligonucleotide 14834 (SEQ ID NO: 29), to approximately 45 nM for oligonucleotide 16922 (SEQ ID NO: 29).

TABLE 7

Dose Response of Chimeric Phosphorothioate/MMI TNF-α Antisense Oligodeoxynucleotides on TNF-α mRNA Levels in PMA-Induced NeoHK Cells

| ISIS # | SEQ ID NO: | ASO Gene Target | Dose | % mRNA Expression | % mRNA Inhibition |
|---|---|---|---|---|---|
| induced | — | — | — | 100% | — |
| 13393 | 49 | control | 25 nM | 87.3% | 12.7% |
| " | " | " | 50 nM | 98.5% | 1.5% |
| " | " | " | 100 nM | 133.1% | — |
| " | " | " | 200 nM | 139.6% | — |
| 14834 | 29 | STOP | 25 nM | 98.7% | 1.3% |
| " | " | " | 50 nM | 70.8% | 29.2% |
| " | " | " | 100 nM | 36.0% | 64.0% |
| " | " | " | 200 nM | 38.2% | 61.8% |
| 16922 | 29 | STOP | 25 nM | 58.9% | 41.1% |
| " | " | " | 50 nM | 28.2% | 71.8% |
| " | " | " | 100 nM | 22.2% | 77.8% |
| " | " | " | 200 nM | 18.9% | 81.1% |

TABLE 8

Dose Response of Chimeric Phosphorothioate/MMI TNF-α Antisense Oligodeoxynucleotides on TNF-α Protein Levels in PMA-Induced NeoHK Cells

| ISIS # | SEQ ID NO: | ASO Gene Target | Dose | % protein Expression | % protein Inhibition |
|---|---|---|---|---|---|
| induced | — | — | — | 100.0% | — |
| 13393 | 49 | control | 25 nM | 117.0% | — |
| " | " | " | 50 nM | 86.6% | 13.4% |
| " | " | " | 100 nM | 98.7% | 1.3% |
| " | " | " | 200 nM | 78.0% | 22.0% |
| 14834 | 29 | STOP | 25 nM | 84.8% | 15.2% |
| " | " | " | 50 nM | 76.9% | 23.1% |
| " | " | " | 100 nM | 44.5% | 55.5% |
| " | " | " | 200 nM | 18.7% | 81.3% |
| 16922 | 29 | STOP | 25 nM | 67.1% | 32.9% |
| " | " | " | 50 nM | 48.6% | 51.4% |

TABLE 6

Nucleotide Sequences of Human TNF-α Chimeric Phosphorothioate/MMI Oligodeoxynucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 14834 | GsGsAsTsGsTsTsCsGsTsCsCsTsCsCsTsCsAsCsA | 29 | 2588–2607 | STOP |
| 16922 | GmGmAmTmGsTsTsCsGsTsCsCsTsCsCsTmCmAmCmA | 29 | 2588–2607 | STOP |
| 16923 | GmGmAmTmGmTmTsCsGsTsCsCsTsCmCmTmCmAmCmA | 29 | 2588–2607 | STOP |
| 13393 | TsCsTsGsAsGsTsAsGsCsAsGsAsGsGsAsGsCsTsC | 49 | target control | |

[1] All cytosine residues are 5-methyl-cytosines; "s" linkages are phosphorothioate linkages, "m" linkages are methylene (methylimino) (MMI).
[2] Co-ordinates from Genbank Accession No. X0291Q, locus name "HSTNFA", SEQ ID NO. 1.

TABLE 8-continued

Dose Response of Chimeric Phosphorothioate/MMI TNF-α
Antisense Oligodeoxynucleotides on TNF-α Protein Levels in
PMA-Induced NeoHK Cells

| ISIS # | SEQ ID NO: | ASO Gene Target | Dose | % protein Expression | % protein Inhibition |
|---|---|---|---|---|---|
| " | " | " | 100 nM | 20.0% | 80.0% |
| " | " | " | 200 nM | 7.9% | 92.1% |
| 16923 | 29 | STOP | 25 nM | 79.9% | 20.1% |
| " | " | " | 50 nM | 69.9% | 30.1% |
| " | " | " | 100 nM | 56.0% | 44.0% |
| " | " | " | 200 nM | 44.5% | 55.5% |

Example 6

Additional Human TNF-α Antisense Oligonucleotide Sequences

A second screening of human TNF-α antisense oligonucleotides was performed. Oligonucleotides were designed specifically against specific regions of the TNF-α gene. A series of oligonucleotides was designed to target introns 1 and 3, and exon 4. Sequences targeting introns 1 or 3 were synthesized as uniformly phosphorothioate oligodeoxynucleotides or mixed phosphorothioate/phosphodiester chimeric backbone oligonucleotides having variable regions of 2'-O-methoxyethyl (2'-MOE) nucleotides and deoxynucleotides. Sequences targeting exon 4 were synthesized as mixed phosphorothioate/phosphodiester chimeric backbone oligonucleotides having variable regions of 2'-O-methoxyethyl (2'-MOE) nucleotides and deoxynucleotides. The sequences of the chimeric oligonucleotides are shown in Table 9. Sequences of the uniformly phosphorothioate oligodeoxynucleotides are shown in Table 11.

These oligonucleotides were screened at 50 nM and 200 nM for their ability to inhibit TNF-α protein secretion, essentially as described in Example 2. Results for the chimeric backbone oligonucleotides are shown in Table 10; results for the uniformly phosphorothioate oligodeoxynucleotides are shown in Table 12.

For the chimeric backbone oligonucleotides targeting introns 1 or 3, oligonucleotide 21688 (SED ID NO. 69) gave 60% inhibition or greater. For chimeric backbone oligonucleotides targeting exon 4, two-thirds of the oligonucleotides gave nearly 60% inhibition or greater (SEQ ID NOs. 88, 90, 91, 92, 93, 94, 97, and 98). See Table 10. For the uniformly phosphorothioate oligodeoxynucleotides, five of nine oligonucleotides targeting intron 3 were effective in reducing TNF-α expression by nearly 60% or greater (SEQ ID NOs. 79, 80, 81, 82, and 84). See Table 12.

Oligonucleotides having SEQ ID NO. 91 and SEQ ID NO. 98 were synthesized as a uniformly phosphorothioate oligodeoxynucleotides or mixed phosphorothioate/phosphodiester chimeric backbone oligonucleotides having variable regions of 2'-O-methoxyethyl (2'-MOE) nucleotides and deoxynucleotides. The sequences and the oligonucleotide chemistries are shown in Table 13. All 2'-MOE cytosines and 2'-deoxy cytosines were 5-methyl-cytosines.

Dose response experiments, as discussed in Example 3, were performed using these oligonucleotides. Included in this experiment were two oligonucleotides targeting intron 1 and two oligonucleotides targeting intron 3. Results are shown in Tables 14 and 15. The oligonucleotides targeting exon 4 with variable regions of 2'-O-methoxyethyl (2'-MOE) nucleotides and deoxynucleotides and/or uniformly phosphorothioate or mixed phosphorothioate/phosphodiester were, in general, comparable to the parent compound.

Oligonucleotides targeting introns 1 or 3 having SEQ ID NOs 66, 69 and 80 were effective in reducing TNF-α mRNA levels by greater than 80% and showed a dose response effect with an $IC_{50}$ approximately 110 nM. See Tables 14 and 15.

TABLE 9

Nucleotide Sequences of TNF-α
Chimeric Backbone (deoxy gapped) 2'-O-methoxyethyl Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 21669 | ToGoCoGoTsCsTsCsTsCsAsTsTsTsCsCoCoCoToT | 50 | 1019–1038 | intron 1 |
| 21670 | ToCoCoCoAsTsCsTsCsTsCsTsCsCsCsToCoToCoT | 51 | 1039–1058 | intron 1 |
| 21671 | CoAoGoCoGsCsAsCsAsTsCsTsTsTsCsAoCoCoCoA | 52 | 1059–1078 | intron 1 |
| 21672 | ToCoToCoTsCsTsCsAsTsCsCsCsTsCsCoCoToAoT | 53 | 1079–1098 | intron 1 |
| 21673 | CoGoToCoTsTsTsCsTsCsCsAsTsGsTsToToToToT | 54 | 1099–1118 | intron 1 |
| 21674 | CoAoCoAoTsCsTsCsTsTsTsCsTsGsCsAoToCoCoC | 55 | 1119–1138 | intron 1 |
| 21675 | CoToCoToCsTsTsCsCsCsAsTsCsTsCoToToGoC | 56 | 1139–1158 | intron 1 |
| 21676 | GoToCoToCsTsCsAsTsCsTsTsTsCsCoToToCoT | 57 | 1159–1178 | intron 1 |
| 21677 | ToToCoCoAsTsGsTsGsCsCsAsGsAsCsAoToCoCoT | 58 | 1179–1198 | intron 1 |
| 21678 | AoToAoCoAsCsAsCsTsTsAsGsTsGsAsGoCoAoCoC | 59 | 1199–1218 | intron 1 |
| 21679 | ToToCoAoTsTsCsAsTsTsCsAsTsTsCsAoCoToCoC | 60 | 1219–1238 | intron 1 |
| 21680 | ToAoToAoTsCsTsGsCsTsTsGsTsTsCsAoToToCoA | 61 | 1239–1258 | intron 1 |

TABLE 9-continued

Nucleotide Sequences of TNF-α
Chimeric Backbone (deoxy gapped) 2'-O-methoxyethyl Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 21681 | CoToGoToCsTsCsCsAsTsAsTsCsTsTsAoToToToA | 62 | 1259–1278 | intron 1 |
| 21682 | ToCoToCoTsTsCsTsCsAsCsAsCsCsCsCoAoCoAoT | 63 | 1279–1298 | intron 1 |
| 21683 | CoAoCoToGsTsTsTsCsTsTsCsCsCsCoCoAoToC | 64 | 1299–1318 | intron 1 |
| 21684 | CoToCoAoCsCsAsTsCsTsTsTsAsTsTsCoAoToAoT | 65 | 1319–1338 | intron 1 |
| 21685 | AoToAoToTsTsCsCsCsGsCsTsCsTsTsToCoToGoT | 66 | 1339–1358 | intron 1 |
| 21686 | CoAoToCoTsCsTsCsTsCsCsTsTsAsGsCoToGoToC | 67 | 1359–1378 | intron 1 |
| 21687 | ToCoToTsCsTsCsCsCsTsTsAsTsCsToCoCoCoC | 68 | 1379–1398 | intron 1 |
| 21688 | GoToGoToGsCsCsAsGsAsCsAsCsCsCsToAoToCoT | 69 | 1399–1418 | intron 1 |
| 21689 | ToCoToToTsCsCsCsTsGsAsGsTsGsTsCoToToCoT | 70 | 1419–1438 | intron 1 |
| 21690 | AoCoCoToTsCsAsGsCsAsTsTsCsAsAoCoAoGoC | 71 | 1439–1458 | intron 1 |
| 21691 | CoToCoCoAsTsTsCsAsTsCsTsGsTsGsToAoToToC | 72 | 1459–1478 | intron 1 |
| 21692 | ToGoAoGoGsTsGsTsCsTsGsGsTsTsTsToCoToCoT | 73 | 1479–1498 | intron 1 |
| 21693 | AoCoAoCoAsTsCsCsTsCsAsGsAsGsCsToCoToToA | 74 | 1871–1890 | intron 3 |
| 21694 | CoToAoGoCsCsCsTsCsCsAsGsGsTsTsCoCoAoAoG | 75 | 1891–1910 | intron 3 |
| 21695 | CoGoGoGoCsTsTsCsAsAsTsCsCsCsCsAoAoAoToC | 76 | 1911–1930 | intron 3 |
| 21696 | AoAoGoToTsCsTsGsCsCsTsAsCsCsAsToCoAoGoC | 77 | 1931–1950 | intron 3 |
| 21697 | GoToCoCoTsCsTsCsCsAsCsAsTsTsGsToCoToCoC | 78 | 1951–1970 | intron 3 |
| 21698 | CoCoToToCsCsCsTsGsAsGsCsTsCsAoGoCoGoA | 79 | 1971–1990 | intron 3 |
| 21699 | GoGoCoCoTsGsTsGsCsTsGsTsTsCsCsToCoCoAoC | 80 | 1991–2010 | intron 3 |
| 21700 | CoGoToToCsTsGsAsGsTsAsTsCsCsCsAoCoToAoA | 81 | 2011–2030 | intron 3 |
| 21701 | CoAoCoAoTsCsCsAsCsCsTsGsGsCsCoAoToGoA | 82 | 2031–2050 | intron 3 |
| 21702 | GoToCoCoTsCsTsCsTsGsTsCsTsGsTsCoAoToCoC | 83 | 2051–2070 | intron 3 |
| 21703 | CoCoAoCoCsCsCsAsCsAsTsCsCsGsGoToToCoCoT | 84 | 2071–2090 | intron 3 |
| 21704 | ToCoCoToGsGsCsCsCsTsCsGsAsGsCsToCoToGoC | 85 | 2091–2110 | intron 3 |
| 21705 | AoToGoToCsGsTsTsCsAsCsTsCsTsCoCoAoCoA | 86 | 2111–2130 | intron 3 |
| 21706 | AoGoAoGoGsAsGsAsGsTsCsAsGsTsGsToGoGoCoC | 87 | 2131–2150 | intron 3 |
| 21722 | GoAoToCoCsAsAsAsGsTsAsGsAsCsCoToGoCoC | 88 | 2561–2580 | exon 4 |
| 21723 | CoAoGoAoCsTsCsGsGsCsAsAsAsGsTsCoGoAoGoA | 89 | 2541–2560 | exon 4 |
| 21724 | ToAoGoToCsGsGsGsCsCsGsAsTsTsGsAoToCoToC | 90 | 2521–2540 | exon 4 |
| 21725 | AoGoCoGoCsTsGsAsGsTsCsGsGsTsCsAoCoCoCoT | 91 | 2501–2520 | exon 4 |
| 21726 | ToCoToCoCsAsGsCsTsGsGsAsAsGsAsCoCoCoCoT | 92 | 2481–2500 | exon 4 |
| 21727 | CoCoCoAoGsAsTsAsGsAsTsGsGsGsCsToCoAoToA | 93 | 2461–2480 | exon 4 |
| 21728 | CoCoAoGoGsGsCsTsTsGsGsCsCsTsCsAoGoCoCoC | 94 | 2441–2460 | exon 4 |
| 21729 | CoCoToCoTsGsGsGsGsTsCsTsCsCsCsToCoToGoG | 95 | 2421–2440 | exon 4 |
| 21730 | CoAoGoGoGsGsCsTsCsTsTsGsAsTsGsGoCoAoGoA | 96 | 2401–2420 | exon 4 |
| 21731 | GoAoGoGoAsGsGsTsTsGsAsCsCsTsTsGoGoToCoT | 97 | 2381–2400 | exon 4 |

TABLE 9-continued

Nucleotide Sequences of TNF-α Chimeric Backbone (deoxy gapped) 2'-O-methoxyethyl Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 21732 | GoGoToAoGsGsAsGsAsCsGsGsCsGsAsToGoCoGoG | 98 | 2361–2380 | exon 4 |
| 21733 | CoToGoAoTsGsGsTsGsTsGsGsGsTsGsAoGoGoAoG | 99 | 2341–2360 | exon 4 |

[1]Emboldened residues are 2'-methoxyethoxy residues (others are 2'-deoxy-). All 2'-methoxyethoxy cytidines and 2'-deoxycytidines are 5-methyl-cytidines; "s" linkages are phosphorothioate linkages, "o" linkages are phosphodiester linkages.
[2]Co-ordinates from Genbank Accession No. X02910, locus name "HSTNFA", SEQ ID NO. 1.

TABLE 10

Dose Response of PMA-Induced neoHK Cells to Chimeric Backbone (deoxy gapped) 2'-O-methoxyethyl TNF-α Antisense Oligonucleotides

| ISIS # | SEQ ID NO: | ASO Gene Target | Dose | % protein Expression | % protein Inhibition |
|---|---|---|---|---|---|
| induced | — | — | — | 100% | — |
| 14834 | 29 | STOP | 50 nM | 76% | 24% |
| " | " | " | 200 nM | 16% | 84% |
| 21669 | 50 | intron 1 | 50 nM | 134% | — |
| " | " | " | 200 nM | 114% | — |
| 21670 | 51 | intron 1 | 50 nM | 122% | — |
| " | " | " | 200 nM | 101% | — |
| 21671 | 52 | intron 1 | 50 nM | 90% | 10% |
| " | " | " | 200 nM | 58% | 42% |
| 21672 | 53 | intron 1 | 50 nM | 122% | — |
| " | " | " | 200 nM | 131% | — |
| 21673 | 54 | intron 1 | 50 nM | 102% | — |
| " | " | " | 200 nM | 110% | — |
| 21674 | 55 | intron 1 | 50 nM | 111% | — |
| " | " | " | 200 nM | 96% | 4% |
| 21675 | 56 | intron 1 | 50 nM | 114% | — |
| " | " | " | 200 nM | 99% | 1% |
| 21676 | 57 | intron 1 | 50 nM | 107% | — |
| " | " | " | 200 nM | 96% | 4% |
| 21677 | 58 | intron 1 | 50 nM | 86% | 14% |
| " | " | " | 200 nM | 95% | 5% |
| 21678 | 59 | intron 1 | 50 nM | 106% | — |
| " | " | " | 200 nM | 107% | — |
| 21679 | 60 | intron 1 | 50 nM | 75% | 25% |
| " | " | " | 200 nM | 73% | 27% |
| 21680 | 61 | intron 1 | 50 nM | 76% | 24% |
| " | " | " | 200 nM | 80% | 20% |
| 21681 | 62 | intron 1 | 50 nM | 79% | 21% |
| " | " | " | 200 nM | 82% | 18% |
| 21682 | 63 | intron 1 | 50 nM | 102% | — |
| " | " | " | 200 nM | 88% | 12% |
| 21683 | 64 | intron 1 | 50 nM | 80% | 20% |
| " | " | " | 200 nM | 66% | 34% |
| 21684 | 65 | intron 1 | 50 nM | 91% | 9% |
| " | " | " | 200 nM | 69% | 31% |
| 21685 | 66 | intron i | 50 nM | 98% | 2% |
| " | " | " | 200 nM | 90% | 10% |
| 21686 | 67 | intron 1 | 50 nM | 97% | 3% |
| " | " | " | 200 nM | 72% | 28% |
| 21687 | 68 | intron 1 | 50 nM | 103% | — |
| " | " | " | 200 nM | 64% | 36% |
| 21688 | 69 | intron 1 | 50 nM | 87% | 13% |
| " | " | " | 200 nM | 40% | 60% |
| 21689 | 70 | intron 1 | 50 nM | 78% | 22% |
| " | " | " | 200 nM | 74% | 26% |
| 21690 | 71 | intron 1 | 50 nM | 84% | 16% |
| " | " | " | 200 nM | 80% | 20% |
| 21691 | 72 | intron 1 | 50 nM | 86% | 14% |
| " | " | " | 200 nM | 75% | 25% |
| 21692 | 73 | intron 1 | 50 nM | 85% | 15% |
| " | " | " | 200 nM | 61% | 39% |
| 21693 | 74 | intron 3 | 50 nM | 81% | 19% |
| " | " | " | 200 nM | 83% | 17% |
| 21694 | 75 | intron 3 | 50 nM | 99% | 1% |
| " | " | " | 200 nM | 56% | 44% |
| 21695 | 76 | intron 3 | 50 nM | 87% | 13% |
| " | " | " | 200 nM | 84% | 16% |
| 21696 | 77 | intron 3 | 50 nM | 103% | — |
| " | " | " | 200 nM | 86% | 14% |
| 21697 | 78 | intron 3 | 50 nM | 99% | 1% |
| " | " | " | 200 nM | 52% | 48% |
| 21698 | 79 | intron 3 | 50 nM | 96% | 4% |
| " | " | " | 200 nM | 47% | 53% |
| 21699 | 80 | intron 3 | 50 nM | 73% | 27% |
| " | " | " | 200 nM | 84% | 16% |
| 21700 | 81 | intron 3 | 50 nM | 80% | 20% |
| " | " | " | 200 nM | 53% | 47% |
| 21701 | 82 | intron 3 | 50 nM | 94% | 6% |
| " | " | " | 200 nM | 56% | 44% |
| 21702 | 83 | intron 3 | 50 nM | 86% | 14% |
| " | " | " | 200 nM | 97% | 3% |
| 21703 | 84 | intron 3 | 50 nM | 88% | 12% |
| " | " | " | 200 nM | 74% | 26% |
| 21704 | 85 | intron 3 | 50 nM | 69% | 31% |
| " | " | " | 200 nM | 65% | 35% |
| 21705 | 86 | intron 3 | 50 nM | 92% | 8% |
| " | " | " | 200 nM | 77% | 23% |
| 21706 | 87 | intron 3 | 50 nM | 95% | 5% |
| " | " | " | 200 nM | 82% | 18% |
| 21722 | 88 | exon 4 | 50 nM | 81% | 19% |
| " | " | " | 200 nM | 41% | 59% |
| 21723 | 89 | exon 4 | 50 nM | 87% | 13% |
| " | " | " | 200 nM | 74% | 26% |
| 21724 | 90 | exon 4 | 50 nM | 68% | 32% |
| " | " | " | 200 nM | 33% | 67% |
| 21725 | 91 | exon 4 | 50 nM | 55% | 45% |
| " | " | " | 200 nM | 30% | 70% |
| 21726 | 92 | exon 4 | 50 nM | 72% | 28% |
| " | " | " | 200 nM | 40% | 60% |
| 21727 | 93 | exon 4 | 50 nM | 67% | 33% |
| " | " | " | 200 nM | 40% | 60% |
| 21728 | 94 | exon 4 | 50 nM | 62% | 38% |
| " | " | " | 200 nM | 41% | 59% |
| 21729 | 95 | exon 4 | 50 nM | 78% | 22% |
| " | " | "y | 200 nM | 53% | 47% |
| 21730 | 96 | exon 4 | 50 nM | 68% | 32% |
| " | " | " | 200 nM | 48% | 52% |

TABLE 10-continued

Dose Response of PMA-Induced neoHK Cells to Chimeric Backbone (deoxy gapped) 2'-O-methoxyethyl TNF-α Antisense Oligonucleotides

| ISIS # | SEQ ID NO: | ASO Gene Target | Dose | % protein Expression | % protein Inhibition |
|---|---|---|---|---|---|
| 21731 | 97 | exon 4 | 50 nM | 77% | 23% |
| " | " | " | 200 nM | 41% | 59% |
| 21732 | 98 | exon 4 | 50 nM | 62% | 38% |
| " | " | " | 200 nM | 28% | 72% |
| 21733 | 99 | exon 4 | 50 nM | 92% | 8% |
| " | " | " | 200 nM | 74% | 26% |

TABLE 11

Nucleotide Sequences of Additional Human TNF-α Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 21804 | TGCGTCTCTCATTTCCCCTT | 50 | 1019–1038 | intron 1 |
| 21805 | TCCCATCTCTCTCCCTCTCT | 51 | 1039–1058 | intron 1 |
| 21806 | CAGCGCACATCTTTCACCCA | 52 | 1059–1078 | intron 1 |
| 21807 | TCTCTCTCATCCCTCCCTAT | 53 | 1079–1098 | intron 1 |
| 21808 | CGTCTTTCTCCATGTTTTTT | 54 | 1099–1118 | intron 1 |
| 21809 | CACATCTCTTTCTGCATCCC | 55 | 1119–1138 | intron 1 |
| 21810 | CTCTCTTCCCCATCTCTTGC | 56 | 1139–1158 | intron 1 |
| 21811 | GTCTCTCCATCTTTCCTTCT | 57 | 1159–1178 | intron 1 |
| 21812 | TTCCATGTGCCAGACATCCT | 58 | 1179–1198 | intron 1 |
| 21813 | ATACACACTTAGTGAGCACC | 59 | 1199–1218 | intron 1 |
| 21814 | TTCATTCATTCATTCACTCC | 60 | 1219–1238 | intron 1 |
| 21815 | TATATCTGCTTGTTCATTCA | 61 | 1239–1258 | intron 1 |
| 21816 | CTGTCTCCATATCTTATTTA | 62 | 1259–1278 | intron 1 |
| 21817 | TCTCTTCTCACACCCCACAT | 63 | 1279–1298 | intron 1 |
| 21818 | CACTTGTTTCTTCCCCCATC | 64 | 1299–1318 | intron 1 |
| 21819 | CTCACCATCTTTATTCATAT | 65 | 1319–1338 | intron 1 |
| 21820 | ATATTTCCCGCTCTTTCTGT | 66 | 1339–1358 | intron 1 |
| 21821 | CATCTCTCTCCTTAGCTGTC | 67 | 1359–1378 | intron 1 |
| 21822 | TCTTCTCTCCTTATCTCCCC | 68 | 1379–1398 | intron 1 |
| 21823 | GTGTGCCAGACACCCTATCT | 69 | 1399–1418 | intron 1 |
| 21824 | TCTTTCCCTGAGTGTCTTCT | 70 | 1419–1438 | intron 1 |
| 21825 | ACCTTCCAGCATTCAACAGC | 71 | 1439–1458 | intron 1 |
| 21826 | CTCCATTCATCTGTGTATTC | 72 | 1459–1478 | intron 1 |
| 21827 | TGAGGTGTCTGGTTTTCTCT | 73 | 1479–1498 | intron 1 |
| 21828 | ACACATCCTCAGAGCTCTTA | 74 | 1871–1890 | intron 3 |
| 21829 | CTAGCCCTCCAAGTTCCAAG | 75 | 1891–1910 | intron 3 |
| 21830 | CGGGCTTCAATCCCCAAATC | 76 | 1911–1930 | intron 3 |
| 21831 | AAGTTCTGCCTACCATCAGC | 77 | 1931–1950 | intron 3 |
| 21832 | GTCCTTCTCACATTGTCTCC | 78 | 1951–1970 | intron 3 |
| 21833 | CCTTCCCTTGAGCTCAGCGA | 79 | 1971–1990 | intron 3 |
| 21834 | GGCCTGTGCTGTTCCTCQAC | 80 | 1991–2010 | intron 3 |
| 21835 | CGTTCTGAGTATCCCACTAA | 81 | 2011–2030 | intron 3 |
| 21836 | CACATCCCACCTGGCCATGA | 82 | 2031–2050 | intron 3 |
| 21837 | GTCCTCTCTGTCTGTCATCC | 83 | 2051–2070 | intron 3 |
| 21838 | CCACCCCACATCCGGTTCCT | 84 | 2071–2090 | intron 3 |
| 21839 | TCCTGGCCCTCGAGCTCTGC | 85 | 2091–2110 | intron 3 |
| 21840 | ATGTCGGTTCACTCTCCACA | 86 | 2111–2130 | intron 3 |
| 21841 | AGAGGAGAGTCAGTGTGGCC | 87 | 2131–2150 | intron 3 |

[1] All "C" residues are 5-methyl-cytosines; all linkages are phosphorothioate linkages.
[2] Co-ordinates from Genbank Accession No. X02910, locus name "HSTNFA", SEQ ID NO. 1.

TABLE 12

Dose Response of PMA-Induced neoHK Cells to TNF-α Antisense Phosphorothioate Oligodeoxynucleotides

| ISIS # | SEQ ID NO: | ASO Gene Target | Dose | % protein Expression | % protein Inhibition |
|---|---|---|---|---|---|
| induced | — | — | — | 100% | — |
| 14834 | 29 | STOP | 50 nM | 80% | 20% |
| " | " | " | 200 nM | 13% | 87% |
| 21812 | 58 | intron 1 | 50 nM | 110% | — |
| " | " | " | 200 nM | 193% | — |
| 21833 | 79 | intron 3 | 50 nM | 88% | 12% |
| " | " | " | 200 nM | 8% | 92% |
| 21834 | 80 | intron 3 | 50 nM | 70% | 30% |
| " | " | " | 200 nM | 18% | 82% |
| 21835 | 81 | intron 3 | 50 nM | 106% | — |
| " | " | " | 200 nM | 42% | 58% |
| 21836 | 82 | intron 3 | 50 nM | 71% | 29% |
| " | " | " | 200 nM | 12% | 88% |
| 21837 | 83 | intron 3 | 50 nM | 129% | — |
| " | " | " | 200 nM | 74% | 26% |
| 21838 | 84 | intron 3 | 50 nM | 85% | 15% |
| " | " | " | 200 nM | 41% | 59% |
| 21839 | 85 | intron 3 | 50 nM | 118% | — |
| " | " | " | 200 nM | 58% | 42% |
| 21840 | 86 | intron 3 | 50 nM | 120% | — |
| " | " | " | 200 nM | 96% | 4% |
| 21841 | 87 | intron 3 | 50 nM | 117% | — |
| " | " | " | 200 nM | 78% | 22% |

TABLE 13

Nucleotide Sequences of TNF-α Chimeric (deoxy gapped) 2'-O-methoxyethyl Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 21725 | AoGoCoGoCsTsGsAsGsTsCsGsGsTsCsAoCoCoCoT | 91 | 2501–2520 | exon 4 |
| 25655 | AsGsCsGsCsTsGsAsGsTsCsGsGsTsCsAsCsCsCsT | " | " | " |
| 25656 | AsGsCsGsCsTsGsAsGsTsCsGsGsTsCsAsCsCsCsT | " | " | " |
| 25660 | AoGoCoGoCsTsGsAsGsTsCsGsGsTsCsAsCoCoCoT | " | " | " |
| 21732 | GoGoToAoGsGsAsGsAsCsGsGsCsGsAsToGoCoGoG | 98 | 2361–2380 | exon 4 |
| 25657 | GsGsTsAsGsGsAsGsAsCsGsGsCsGsAsTsGsCsGsG | " | " | " |
| 25658 | GsGsTsAsGsGsAsGsAsCsGsGsCsGsAsTsGsCsGsG | " | " | " |
| 25661 | GoGoToAsGsGsAsGsAsCsGsGsCsGsAsTsGoCoGoG | " | " | " |

[1]Emboldened residues are 2'-methoxyethoxy residues (others are 2'-deoxy-). All 2'-methoxyethoxy cytidines and 2'-deoxycytidines are 5-methyl-cytidines; "s" linkages are phosphorothioate linkages, "o" linkages are phosphodiester linkages.
[2]Co-ordinates from Genbank Accession No. X02910, locus name "HSTNFA", SEQ ID NO. 1.

TABLE 14

Dose Response of 20 Hour PMA-Induced neoHK Cells to TNF-α Antisense Oligonucleotides (ASOs)

| ISIS # | SEQ ID NO: | ASO Gene Target | Dose | % protein Expression | % protein Inhibition |
|---|---|---|---|---|---|
| induced | — | — | — | 100% | — |
| 14834 | 29 | STOP | 75 nM | 91.2% | 8.8% |
| " | " | " | 150 nM | 42.0% | 58.0% |
| " | " | " | 300 nM | 16.9% | 83.1% |
| 21820 | 66 | intron 1 | 75 nM | 79.0% | 21.0% |
| " | " | " | 150 nM | 34.5% | 65.5% |
| " | " | " | 300 nM | 15.6% | 84.4% |
| 21823 | 69 | intron 1 | 75 nM | 79.5% | 20.5% |
| " | " | " | 150 nM | 31.8% | 68.2% |
| " | " | " | 300 nM | 16.2% | 83.8% |
| 21725 | 91 | exon 4 | 75 nM | 74.8% | 25.2% |
| " | " | " | 150 nM | 58.4% | 41.6% |
| " | " | " | 300 nM | 45.2% | 54.8% |
| 25655 | 91 | exon 4 | 75 nM | 112.0% | — |
| " | " | " | 150 nM | 55.0% | 45.0% |
| " | " | " | 300 nM | 39.3% | 60.7% |
| 25656 | 91 | exon 4 | 75 nM | 108.3% | — |
| " | " | " | 150 nM | 60.7% | 39.3% |
| " | " | " | 300 nM | 42.8% | 57.2% |
| 25660 | 91 | exon 4 | 75 nM | 93.2% | 6.8% |
| " | " | " | 150 nM | 72.8% | 27.2% |
| " | " | " | 300 nM | 50.3% | 49.7% |

TABLE 15

Dose Response of 20 Hour PMA-Induced neoHK Cells to TNF-α Antisense Oligonucleotides (ASOs)

| ISIS # | SEQ ID NO: | ASO Gene Target | Dose | % protein Expression | % protein Inhibition |
|---|---|---|---|---|---|
| induced | — | — | — | 100% | — |
| 14834 | 29 | STOP | 75 nM | 44.9% | 55.1% |

TABLE 15-continued

Dose Response of 20 Hour PMA-Induced neoHK Cells to TNF-α Antisense Oligonucleotides (ASOs)

| ISIS # | SEQ ID NO: | ASO Gene Target | Dose | % protein Expression | % protein Inhibition |
|---|---|---|---|---|---|
| " | " | " | 150 nM | 16.3% | 83.7% |
| " | " | " | 300 nM | 2.2% | 97.8% |
| 21834 | 80 | intron 3 | 75 nM | 102.9% | — |
| " | " | " | 150 nM | 24.5% | 75.5% |
| " | " | " | 300 nM | 19.1% | 80.9% |
| 21836 | 82 | intron 3 | 75 nM | 70.8% | 29.2% |
| " | " | " | 150 nM | 55.9% | 44.1% |
| " | " | " | 300 nM | 32.7% | 67.3% |
| 21732 | 98 | exon 4 | 75 nM | 42.4% | 57.6% |
| " | " | " | 150 nM | 34.9% | 65.1% |
| " | " | " | 300 nM | 15.4% | 84.6% |
| 25657 | 98 | exon 4 | 75 nM | 46.7% | 53.3% |
| " | " | " | 150 nM | 72.0% | 28.0% |
| " | " | " | 300 nM | 50.6% | 49.4% |
| 25658 | 98 | exon 4 | 75 nM | 83.7% | 16.3% |
| " | " | " | 150 nM | 56.6% | 43.4% |
| " | " | " | 300 nM | 36.9% | 63.1% |
| 25661 | 98 | exon 4 | 75 nM | 54.9% | 45.1% |
| " | " | " | 150 nM | 34.4% | 65.6% |
| " | " | " | 300 nM | 8.6% | 91.4% |

Example 7

Activity of Fully 2'-MOE Modified TNF-α Antisense Oligonucleotides

A series of antisense oligonucleotides were synthesized targeting the terminal twenty nucleotides of each exon at every exon-intron junction of the TNF-α gene. These oligonucleotides were synthesized as fully 2'-methoxyethoxy modified oligonucleotides. The oligonucleotide sequences are shown in Table 16. Oligonucleotide 12345 (SEQ ID NO. 106) is an antisense oligonucleotide targeted to the human intracellular adhesion molecule-1 (ICAM-1) and was used as an unrelated target control.

The oligonucleotides were screened at 50 nM and 200 nM for their ability to inhibit TNF-α mRNA levels, as described in Example 3. Results are shown in Table 17. Oligonucleotide 21794 (SEQ ID NO. 102) showed an effect at both doses, with greater than 75% inhibition at 200 nM.

TABLE 16

Nucleotide Sequences of Human TNF-α Uniform 2'-MOE Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION[3] |
|---|---|---|---|---|
| 21792 | AGGCACTCACCTCTTCCCTC | 100 | 0972–0991 | E1/I1 |
| 21793 | CCCTGGGGAACTGTTGGGGA | 101 | 1579–1598 | I1/E2 |
| 21794 | AGACACTTACTGACTGCCTG | 102 | 1625–1644 | E2/I2 |
| 21795 | GAAGATGATCCTGAAGAGGA | 103 | 1812–1831 | I2/E3 |
| 21796 | GAGCTCTTACCTACAACATG | 104 | 1860–1879 | E3/I3 |
| 21797 | TGAGGGTTTGCTGGAGGGAG | 105 | 2161–2180 | I3/E4 |
| 12345 | GATCGCGTCGGACTATGAAG | 106 | target control | |

[1]Emboldened residues are 2'-methoxyethoxy residues, 2'-methoxyethoxy cytosine residues are 5-methyl-cytosines; all linkages are phosphorothioate linkages.
[2]Co-ordinates from Genbank Accession No. X02910, locus name "HSTNFA", SEQ ID NO. 1.
[3]Each target region is an exon-intron junction and is represented in the form, for example, I1/E2, where I, followed by a number, refers to the intron number and E, followed by a number, refers to the exon number.

TABLE 17

Dose Response of neoHK Cells to TNF-α Antisense 2'-MOE Oligonucleotides

| ISIS # | SEQ ID NO: | ASO Gene Target | Dose | % mRNA Expression | % mRNA Inhibition |
|---|---|---|---|---|---|
| induced | — | — | — | 100% | — |
| 12345 | 106 | control | 50 nM | 121% | — |
| " | " | " | 200 nM | 134% | — |
| 13393 | 49 | control | 50 nM | 110% | — |
| " | " | " | 200 nM | 112% | — |
| 14834 | 29 | STOP | 50 nM | 92% | 8% |
| " | " | " | 200 nM | 17% | 83% |
| 21792 | 100 | E1/I1 | 50 nM | 105% | — |
| " | " | " | 200 nM | 148% | — |
| 21793 | 101 | I1/E2 | 50 nM | 106% | — |
| " | " | " | 200 nM | 172% | — |
| 21794 | 102 | E2/I2 | 50 nM | 75% | 25% |
| " | " | " | 200 nM | 23% | 77% |
| 21795 | 103 | I2/E3 | 50 nM | 79% | 21% |
| " | " | " | 200 nM | 125% | — |
| 21796 | 104 | E3/I3 | 50 nM | 56% | 44% |
| " | " | " | 200 nM | 150% | — |
| 21797 | 105 | I3/E4 | 50 nM | 90% | 10% |
| " | " | " | 200 nM | 128% | — |

Example 8

Mouse TNF-α Oligonucleotide Sequences

Antisense oligonucleotides were designed to target mouse TNF-α. Target sequence data are from the TNF-α cDNA sequence published by Semon, D. et al. (*Nucleic Acids Res.* 1987, 15, 9083–9084); Genbank accession number Y00467, provided herein as SEQ ID NO: 107. Oligonucleotides were synthesized primarily as phosphorothioate oligodeoxynucleotides. Oligonucleotide sequences are shown in Table 18. Oligonucleotide 3082 (SEQ ID NO. 141) is an antisense oligodeoxynucleotide targeted to the human intracellular adhesion molecule-1 (ICAM-1) and was used as an unrelated target control. Oligonucleotide 13108 (SEQ ID NO. 142) is an antisense oligodeoxynucleotide targeted to the herpes simplex virus type 1 and was used as an unrelated target control.

P388D1, mouse macrophage cells (obtained from American Type Culture Collection, Manassas, Va.) were cultured in RPMI 1640 medium with 15% fetal bovine serum (FBS) (Life Technologies, Rockville, Md.).

At assay time, cell were at approximately 90% confluency. The cells were incubated in the presence of OPTI-MEM® medium (Life Technologies, Rockville, Md.), and the oligonucleotide formulated in LIPOFECTIN® (Life Technologies), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. For an initial screen, the oligonucleotide concentration was 100 nM in 3 μg/ml LIPOFECTIN®. Treatment was for four hours. After treatment, the medium was removed and the cells were further incubated in RPMI medium with 15% FBS and induced with 10 ng/ml LPS. mRNA was analyzed 2 hours post-induction with PMA.

Total mRNA was isolated using the TOTALLY RNA™ kit (Ambion, Austin, Tex.), separated on a 1% agarose gel, transferred to HYBOND™-N+ membrane (Amersham, Arlington Heights, Ill.), a positively charged nylon membrane, and probed. A TNF-α probe consisted of the 502 bp EcoRI-HindIII fragment from BBG 56 (R&D Systems, Minneapolis, Minn.), a plasmid containing mouse TNF-α cDNA. A glyceraldehyde 3-phosphate dehydrogenase (G3PDH) probe consisted of the 1.06 kb HindIII fragment from pHcGAP (American Type Culture Collection, Manassas, Va.), a plasmid containing human G3PDH cDNA. The fragments were purified from low-melting temperature agarose, as described in Maniatis, T., et al., *Molecular Cloning: A Laboratory Manual*, 1989 and labeled with REDIVUE™ ³²P-dCTP (Amersham Pharmacia Biotech, Piscataway, N.J.) and PRIME-A-GENE® labelling kit (Promega, Madison, Wis.). mRNA was quantitated by a PhosphoImager (Molecular Dynamics, Sunnyvale, Calif.).

Secreted TNF-α protein levels were measured using a mouse TNF-α ELISA kit (R&D Systems, Minneapolis, Minn. or Genzyme, Cambridge, Mass.).

TABLE 18

Nucleotide Sequences of Mouse TNF-α phosphorothioate Oligodeoxynucleotides

| ISIS NO. | NUCLEOTIDE SEQUENCE1 (5'->3') | TARGET GENE SEQNUCLEOTIDE ID CO-NO: ORDINATES² | GENE TARGET REGION |
|---|---|---|---|
| 14846 | GAGCTTCTGCTGGCTG-GCTG | 108 4351–4370 | 5'-UTR |
| 14847 | CCTTGCTGTCCTCGCT-GAGG | 109 4371–4390 | 5'-UTR |
| 14848 | TCATGGTGTCTTTTCTG-GAG | 110 4511–4530 | AUG |
| 14849 | CTTTCTGTGCTCATGGT-GTC | 111 4521–4540 | AUG |
| 14850 | GCGGATCATGCTTTCT-GTGC | 112 4531–4550 | coding |
| 14851 | GGGAGGCCATTTGG-GAACTT | 113 5225–5244 | junction |
| 14852 | CGAATTTTGAGAAGAT-GATC | 114 5457–5476 | junction |
| 14846 | GAGCTTCTGCTGGCTG-GCTG | 108 4351–437C | 5'-UTR |

TABLE 18-continued

Nucleotide Sequences of Mouse TNF-α phosphorothioate Oligodeoxynucleotides

| ISIS NO. | NUCLEOTIDE SEQUENCE1 (5'->3') | TARGET GENE SEQNUCLEOTIDE ID CO-NO: ORDINATES² | GENE TARGET REGION |
|---|---|---|---|
| 14853 | CTCCTCCACTTGGTG-GTTTG | 115 5799–5818 | junction |
| 14854 | CCTGAGATCTTATC-CAGCCT | 116 6540–6559 | 3'-UTR |
| 14855 | CAATTACAGTCACG-GCTCCC | 117 6927–6946 | 3'-UTR |
| 15921 | CCCTTCATTCTCAAG-GCACA | 118 5521–5540 | junction |
| 15922 | CACCCCTCAACCCGC-CCCCC | 119 5551–5570 | intron |
| 15923 | AGAGCTCTGTCTTTTCT-CAG | 120 5581–5600 | intron |
| 15924 | CACTGCTCTGACTCT-CACGT | 121 5611–5630 | intron |
| 15925 | ATGAGGTCCCGGGTGGC-CCC | 122 5651–5670 | intron |
| 15926 | CACCCTCTGTCTTTCCA-CAT | 123 5681–5700 | intron |
| 15927 | CTCCACATCCTGAGCCT-CAG | 124 5731–5750 | intron |
| 15928 | ATTGAGTCAGTGTCAC-CCTC | 125 5761–5780 | intron |
| 15929 | GCTGGCTCAGCCACTC-CAGC | 126 5821–5840 | coding |
| 15930 | TCTTTGAGATCCATGC-CGTT | 127 5861–5880 | coding |
| 15931 | AACCCATCGGCTGGCAC-CAC | 128 5891–5910 | coding |
| 15932 | GTTTGAGCTCAGC-CCCCTCA | 129 6061–6080 | coding |
| 15933 | CTCCTCCCAGG-TATATGGGC | 130 6091–6110 | coding |
| 15934 | TGAGTTGGTCCCCCT-TCTCC | 131 6121–6140 | coding |
| 15935 | CAAAGTAGACCTGCCCG-GAC | 132 6181–6200 | coding |
| 15936 | ACACCCATTCCCTTCA-CAGA | 133 6211–6230 | STOP |
| 15937 | CATAATCCCCTTTCTAAGTT | 134 6321–6340 | 3'-UTR |
| 15938 | CACAGAGTTGGACTCT-GAGC | 135 6341–6360 | 3'-UTR |
| 15939 | CAGCATCTTGTGTTTCT-GAG | 136 6381–6400 | 3'-UTR |
| 15940 | CACAGTCCAGGTCACT-GTCC | 137 6401–6420 | 3'-UTR |
| 15941 | TGATGGTGGTGCAT-GAGAGG | 138 6423–6442 | 3'-UTR |
| 15942 | GTGAATTCGGAAAGC-CCATT | 139 6451–6470 | 3'-UTR |

TABLE 18-continued

Nucleotide Sequences of Mouse TNF-α phosphorothioate Oligodeoxynucleotides

| ISIS NO. | NUCLEOTIDE SEQUENCE1 (5'->3') | TARGET GENE SEQ ID NO: | NUCLEOTIDE CO-ORDINATES[2] | GENE TARGET REGION |
|---|---|---|---|---|
| 15943 | CCTGACCACTCTC-CCTTTGC | 140 | 6501–6520 | 3'-UTR |
| 3082 | TGCATCCCCCAGGCCACCAT | 141 | | target control |
| 13108 | GCCGAGGTCCATGTCG-TACGC | 142 | | target control |

[1]All "C" residues are 5-methyl-cytosines except underlined "C" residues are unmodified cytosines; all linkages are phosphorothioate linkages.
[2]Co-ordinates from Genbank Accession No. Y00467, locus name "MMTNFAB", SEQ ID NO. 107.

Results are shown in Table 19. Oligonucleotides 14853 (SEQ ID NO. 115), 14854 (SEQ ID NO. 116), 14855 (SEQ ID NO. 117), 15921 (SEQ ID NO. 118), 15923 (SEQ ID NO. 120), 15924 (SEQ ID NO. 121), 15925 (SEQ ID NO. 122), 15926 (SEQ ID NO. 123), 15929 (SEQ ID NO. 126), 15930 (SEQ ID NO. 127), 15931 (SEQ ID NO. 128), 15932 (SEQ ID NO. 129), 15934 (SEQ ID NO. 131), 15935 (SEQ ID NO. 132), 15936 (SEQ ID NO. 133), 15937 (SEQ ID NO. 134), 15939 (SEQ ID NO. 136), 15940 (SEQ ID NO. 137), 15942 (SEQ ID NO. 139), and 15943 (SEQ ID NO. 140) gave better than 50% inhibition. Oligonucleotides 15931 (SEQ ID NO. 128), 15932 (SEQ ID NO. 129), 15934 (SEQ ID NO. 131), and 15943 (SEQ ID NO. 140) gave 75% inhibition or better.

TABLE 19

Inhibition of Mouse TNF-α mRNA expression in P388D1 Cells by Phosphorothioate Oligodeoxynucleotides

| ISIS No: | SEQ ID NO: | GENE TARGET REGION | % mRNA EXPRESSION | % mRNA INHIBITION |
|---|---|---|---|---|
| induced | — | — | 100% | 0% |
| 3082 | 141 | control | 129% | — |
| 13664 | 42 | control | 85% | 15% |
| 14846 | 108 | 5'-UTR | 84% | 16% |
| 14847 | 109 | 5'-UTR | 88% | 12% |
| 14848 | 110 | AUG | 60% | 40% |
| 14849 | 111 | AUG | 75% | 25% |
| 14850 | 112 | coding | 67% | 33% |
| 14851 | 113 | junction | 62% | 38% |
| 14852 | 114 | junction | 69% | 31% |
| 14853 | 115 | junction | 49% | 51% |
| 14854 | 116 | 3'-UTR | 31% | 69% |
| 14855 | 117 | 3'-UTR | 39% | 61% |
| 15921 | 118 | junction | 42% | 58% |
| 15922 | 119 | intron | 64% | 36% |
| 15923 | 120 | intron | 31% | 69% |
| 15924 | 121 | intron | 29% | 71% |
| 15925 | 122 | intron | 30% | 70% |
| 15926 | 123 | intron | 29% | 71% |
| 15928 | 125 | intron | 59% | 41% |
| 15929 | 126 | coding | 38% | 62% |
| 15930 | 127 | coding | 43% | 57% |
| 15931 | 128 | coding | 23% | 77% |
| 15932 | 129 | coding | 25% | 75% |
| 15933 | 130 | coding | 52% | 48% |
| 15934 | 131 | coding | 21% | 79% |
| 15935 | 132 | coding | 39% | 61% |
| 15936 | 133 | STOP | 35% | 65% |
| 15937 | 134 | 3'-UTR | 45% | 55% |
| 15938 | 135 | 3'-UTR | 76% | 24% |
| 15939 | 136 | 3'-UTR | 33% | 67% |
| 15940 | 137 | 3'-UTR | 38% | 62% |
| 15941 | 138 | 3'-UTR | 54% | 46% |
| 15942 | 139 | 3'-UTR | 42% | 58% |
| 15943 | 140 | 3'-UTR | 25% | 75% |

Example 9

Dose Response of Antisense Phosphorothiaote Oligodeoxynucleotide Effects on Mouse TNF-α mRNA Levels in P388D1 Cells Four of the more active oligonucleotides from the initial screen were chosen for dose response assays. These include oligonucleotides 15924 (SEQ ID NO. 121), 15931 (SEQ ID NO. 128), 15934 (SEQ ID NO. 131) and 15943 (SEQ ID NO. 140). P388D1 cells were grown, treated and processed as described in Example 8. LIPOFECTIN® was added at a ratio of 3 µg/ml per 100 nM of oligonucleotide. The control included LIPOFECTIN® at a concentration of 6 µg/ml. Results are shown in Table 20. Each oligonucleotide tested showed a dose response effect with maximal inhibition about 70% or greater and $IC_{50}$ values less than 50 nM.

TABLE 20

Dose Response of LPS-Induced P388D1 Cells to TNF-α Antisense Phosphorothioate Oligodeoxynucleotides (ASOs)

| ISIS # | SEQ ID NO: | ASO Gene Target | Dose | % mRNA Expression | % mRNA Inhibition |
|---|---|---|---|---|---|
| induced | — | — | — | 100% | — |
| 13108 | 142 | control | 25 nM | 68% | 32% |
| " | " | " | 50 nM | 71% | 29% |
| " | " | " | 100 nM | 64% | 36% |
| " | " | " | 200 nM | 75% | 25% |
| 15924 | 121 | intron | 25 nM | 63% | 37% |
| " | " | " | 50 nM | 49% | 51% |
| " | " | " | 100 nM | 36% | 64% |
| " | " | " | 200 nM | 31% | 69% |
| 15931 | 128 | coding | 25 nM | 42% | 58% |
| " | " | " | 50 nM | 30% | 70% |
| " | " | " | 100 nM | 17% | 83% |
| " | " | " | 200 nM | 16% | 84% |
| 15934 | 131 | coding | 25 nM | 37% | 63% |
| " | " | " | 50 nM | 26% | 74% |
| " | " | " | 100 nM | 13% | 87% |
| " | " | " | 200 nM | 13% | 87% |
| 15943 | 140 | 3'-UTR | 25 nM | 38% | 62% |
| " | " | " | 50 nM | 38% | 62% |
| " | " | " | 100 nM | 16% | 84% |
| " | " | " | 200 nM | 16% | 84% |

Example 10

Design and Testing of 2'-O-methoxyethyl (Deoxy Gapped) TNF-α Antisense Oligonucleotides on TNF-α Levels in P388D1 Cells Oligonucleotides having SEQ ID NO: 128, SEQ ID NO: 131, and SEQ ID NO: 140 were synthesized as uniformly phosphorothioate oligodeoxynucleotides or mixed phosphorothioate/phosphodiester chimeric oligonucleotides having variable regions of 2'-O-methoxyethyl (2'-MOE) nucleotides and deoxynucleotides. The sequences and the oligonucleotide chemistries are shown in Table 21. All 2'-MOE cytosines were 5-methyl-cytosines.

Oligonucleotides were screened as described in Example 8. Results are shown in Table 22. All the oligonucleotides tested, except oligonucleotide 16817 (SEQ ID NO. 140) showed 44% or greater inhibition of TNF-α mRNA expression. Oligonucleotides 16805 (SEQ ID NO: 131), 16813 (SEQ ID NO: 140), and 16814 (SEQ ID NO: 140) showed greater than 70% inhibition.

TABLE 21

Nucleotide Sequences of Mouse 2'-O-methoxyethyl (deoxy gapped) TNF-αOligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 15931 | AsAsCsCsAsTsCsGsGsCsTsGsGsCsAsCsAsC | 128 | 5891–5910 | coding |
| 16797 | AoAoCoCsAsTsCsGsGsCsTsGsGsCsAsCoCoAoC | " | 5891–5910 | coding |
| 16798 | AsAsCsC sCsAsTsCsGsGsCsTsGsG-sCsAsCsCsAsC | " | 5891–5910 | coding |
| 16799 | AoAoCoCoCsAsTsCsGsGsCsTsGsGsGsCsAoCoCoAoC | " | 5891–5910 | coding |
| 16800 | AsAsCsCsAsTsCsGsGsCsTsGsGsCsAsCsCsAsC | " | 5891–5910 | coding |
| 16801 | AoAoCoCoAoToCoGsGsCsTsGsGsCsAsCsCsAsC | " | 5891–5910 | coding |
| 16802 | AsAsCsCsAsTsCsGsGsCsTsGsGsCsAsCsAsC | " | 5891–5910 | coding |
| 16803 | AsAsCsCsAsTsCsGsGsCsToGoGoCoAoCoAoC | " | 5891–5910 | coding |
| 16804 | AsAsCsCsAsTsCsGsGsCsTsGsGsCsAsCsCsAsC | " | 5891–5910 | coding |
| 15934 | TsGsAsGsTsTsGsGsTsCsQsCsCsCsTsTsCsTsCsC | 131 | 6121–6140 | coding |
| 16805 | ToGoAoGsTsTsGsGsTsCsCsCsCsCsTsTsCoToCoC | " | 6121–6140 | coding |
| 16806 | TsGsAsGsTsTsGsGsTsCsCsCsCsCsTsTsCsTsCsC | " | 6121–6140 | coding |
| 16807 | ToGoAoGoTsTsGsGsTsCsCsCsCsCsTsToCoToCoC | " | 6121–6140 | coding |
| 16808 | TsGsAsGsTsTsGsGsTsCsCsCsCsCsTsTsCsTsCsC | " | 6121–6140 | coding |
| 16809 | ToGoAoGoToGoGoTsCsCsCsCsCsTsTsCsTsCsC | " | 6121–6140 | coding |
| 16810 | TsGsAsGsTsTsGsGsTsCsCsCsCsCsTsTsCsTsCsC | " | 6121–6140 | coding |
| 16811 | TsGsAsGsTsTsGsGsTsCsCsCoCoCoToToCoToCoC | " | 6121–6140 | coding |
| 16812 | TsGsAsGsTsTsGsGsTsCsCsCsCsCsTsTsCsTsCsC | " | 6121–6140 | coding |
| 15943 | CsCsTsGsAsCsCsAsCsTsCsTsCsCsCsTsTsGsC | 140 | 6501–6520 | 3'-UTR |
| 16813 | CoCoToGsAsCsCsAsCsTsCsTsCsCsCsTsTsToGoC | " | 6501–6520 | 3'-UTR |
| 16814 | CsCsTsGsAsCsCsAsCsTsCsTsCsCsCsTsTsTsGsC | " | 6501–6520 | 3'-UTR |
| 16815 | CoCoToGoAsCsCsAsCsTsCsTsCsCsCsToToGoC | " | 6501–6520 | 3'-UTR |
| 16816 | CsCsTsGsAsCsCsAsCsTsCsTsCsCsCsTsTsGsC | " | 6501–6520 | 3'-UTR |
| 16817 | CoCoToGoAoCoCoAoCsTsCsTsCsCsCsTsTsTsGsC | " | 6501–6520 | 3'-UTR |
| 16818 | CsCsTsGsAsCsCsAsCsTsCsTsCsCsCsTsTsTsGsC | " | 6501–6520 | 3'-UTR |
| 16819 | CsCsTsGsAsCsCsAsCsTsCsToCoCoCoToToGoC | " | 6501–6520 | 3'-UTR |
| 16820 | CsCsTsGsAsCsCsAsCsTsCsTsCsCsCsTsTsGsC | " | 6501–6520 | 3'-UTR |

[1]Emboldened residues are 2'-methoxyethoxy residues (others are 2'-deoxy-). All 2'-methoxyethoxy cytidines are 5-methyl-cytidines; "s" linkages are phosphorothioate linkages, "o" linkages are phosphodiester linkages,"o" linkages are phosphodiester linkages.
[2]Co-ordinates from Genbank Accession No. Y00467, locus name "MMTNFAB", SEQ ID NO. 107.

TABLE 22

Inhibition of mouse TNF-α mRNA expression in P388D1 Cells by 2'-O-methoxyethyl (deoxy gapped) Oligonucleotides

| ISIS No: | SEQ ID NO: | GENE TARGET REGION | % mRNA EXPRESSION | % mRNA INHIBITION |
|---|---|---|---|---|
| induced | — | 13 | 100% | 0% |
| 13108 | 142 | control | 87% | 13% |
| 15934 | 131 | coding | 28% | 72% |
| 16797 | 128 | coding | 33% | 67% |
| 16798 | " | coding | 34% | 66% |
| 16799 | " | coding | 56% | 44% |
| 16800 | " | coding | 35% | 65% |
| 16801 | " | coding | 34% | 66% |
| 16802 | " | coding | 38% | 62% |
| 16803 | " | coding | 35% | 65% |
| 16804 | " | coding | 39% | 61% |
| 16805 | 131 | coding | 29% | 71% |
| 16806 | " | coding | 31% | 69% |
| 16807 | " | coding | 46% | 54% |
| 16808 | " | coding | 43% | 57% |
| 16809 | " | coding | 33% | 67% |
| 16810 | " | coding | 37% | 63% |
| 16811 | " | coding | 40% | 60% |
| 16812 | " | coding | 31% | 69% |
| 16813 | 140 | 3'-UTR | 28% | 72% |
| 16814 | " | 3'-UTR | 28% | 72% |
| 16815 | " | 3'-UTR | 46% | 54% |
| 16816 | " | 3'-UTR | 49% | 51% |
| 16817 | " | 3'-UTR | 172% | — |
| 16818 | " | 3'-UTR | 34% | 66% |
| 16819 | " | 3'-UTR | 51% | 49% |
| 16820 | " | 3'-UTR | 44% | 56% |

Example 11

Effect of TNF-α Antisense Oligonucleotides in a Murine Model for Non-Insulin-dependent Diabetes Mellitus The db/db mouse model, a standard model for non-insulin-dependent diabetes mellitus (NIDDM; Hotamisligil, G. S., et al., Science, 1993, 259, 87–90), was used to assess the activity of TNF-α antisense oligonucleotides on blood glucose levels and TNF-α mRNA levels in whole mice. These mice have elevated blood glucose levels and TNF-α mRNA levels compared to wild type mice. Female db/db mice and wild-type littermates were purchased from Jackson Laboratories (Bar Harbor, Me.). The effect on oligonucleotide 15931 (SEQ ID NO. 128) on blood glucose levels was determined. For determination of TNF-α mRNA levels, oligonucleotide 15931 (SEQ ID NO. 128), a uniformly modified phosphorothioate oligodeoxynucleotide, was compared to oligonucleotide 25302 (SEQ ID NO. 128), a mixed phosphorothioate/phosphodiester chimeric oligonucleotide having regions of 2'-O-methoxyethyl (2'-MOE) nucleotides and deoxynucleotides. The sequences and chemistries are shown in Table 23. Oligonucleotide 18154 (SEQ ID NO. 143) is an antisense mixed phosphorothioate/phosphodiester chimeric oligonucleotide, having regions of 2'-O-methoxyethyl (2'-MOE) nucleotides and deoxynucleotides, targeted to the human vascular cell adhesion molecule-1 (VCAM-1) and was used as an unrelated target control.

TABLE 23

Nucleotide Sequence of TNF-α Antisense Oligonucleotide

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 15931 | AACCCATCGGCTGGCACCAC | 128 | 5891–5910 | coding |
| 25302 | AACCCATCGGCTGGCACCAC | 128 | 5891–5910 | coding |
| 18154 | TCAAGCAGTGCCACCGATCC | 143 | target control | |

[1]All 2'-methoxyethyl cytosines and 2'-deoxy cytosines residues are 5-methyl-cytosines; all linkages are phosphorothioate linkages.
[2]Co-ordinates from Genbank Accession No. Y00467, locus name "MNTNFAB", SEQ ID NO. 107.

db/db mice, six to ten weeks old, were dosed intraperitoneally with oligonucleotide every other day for 2 weeks at 10 mg/kg. The mice were fasted for seven hours prior to administration of the oligonucleotide. The mice were bled via retro orbital sinus every other day, and glucose measurements were performed on the blood. Results are shown in Table 24. Oligonucleotide 15931 (SEQ ID NO. 128) was able to reduce blood glucose levels in db/db mice to levels comparable with wild type mice. Food intake between wild type mice, treated and untreated, did not differ. Food intake between db/db mice, treated and untreated, although higher than wild type mice, did not differ significantly.

Samples of the fat (adipose) tissue from the inguinal fat pads were taken for RNA extraction. RNA was extracted according to Current Protocols in Molecular Biology, 1997, Ausubel, F., et al. ed., John Wiley & Sons. RNA was purified using the RNA clean up procedure of the RNEASY® Mini kit (Qiagen, Valencia, Calif.). TNF-α mRNA levels were measured using the RIBOQUANT® kit (PharMingen, San Diego, Calif.) with 15 µg of RNA per lane. The probe used was from the mCK-3b Multi-Probe Template set (PharMingen, San Diego, Calif.) labeled with [$\alpha^{32}$P]UTP (Amersham Pharmacia Biotech, Piscataway, N.J.). Results are shown in Table 25. Both oligonucleotide 15931 (SEQ ID NO. 128) and 25302 (SEQ ID NO. 128) were able to reduce TNF-α levels in fat, with 25302 (SEQ ID NO. 128) reducing TNF-α to nearly wild-type levels.

TABLE 24

Level of Blood Glucose in Normal and db/db Mice After Treatment with TNF-α Antisense Oligonucleotides

| Mouse Strain | ISIS # | SEQ ID NO: | ASO Gene Target | Time (days) | blood glucose (mg/dL) |
|---|---|---|---|---|---|
| wild type | — | — | — | 1 | 140 |
| " | 15931 | 128 | coding | " | 138 |
| db/db | — | — | — | 1 | 260 |
| " | 15931 | 128 | coding | " | 254 |
| wild type | — | — | — | 9 | 175 |
| " | 15931 | 128 | coding | " | 163 |
| db/db | — | — | — | 9 | 252 |
| " | 15931 | 128 | coding | " | 128 |

TABLE 25

Level of TNF-α mRNA in Fat of db/db Mice After
Treatment with TNF-α Antisense Oligonucleotides

| ISIS No: | SEQ ID NO: | GENE TARGET REGION | % mRNA EXPRESSION |
|---|---|---|---|
| wt saline | — | — | 100% |
| db/db saline | — | — | 362% |
| 18154 | 142 | control | 130% |
| 15931 | 128 | coding | 210% |
| 25302 | 128 | coding | 417% |

Example 12

Effect of TNF-α Antisense Oligonucleotides in a Murine Model for Rheumatoid Arthritis Collagen-induced arthritis (CIA) was used as a murine model for arthritis (Mussener, A., et al., *Clin. Exp. Immunol.*, 1997, 107, 485–493). Female DBA/1LacJ mice (Jackson Laboratories, Bar Harbor, Me.) between the ages of 6 and 8 weeks were used to assess the activity of TNF-α antisense oligonucleotides.

On day 0, the mice were immunized at the base of the tail with 100 µg of bovine type II collagen which is emulsified in Complete Freund's Adjuvant (CFA). On day 7, a second booster dose of collagen was administered by the same route. On day 14, the mice were injected subcutaneously with 100 µg of LPS. Oligonucleotide was administered intraperitoneally daily (10 mg/kg bolus) starting on day −3 (three days before day 0) and continuing for the duration of the study.

Weights were recorded weekly. Mice were inspected daily for the onset of CIA. Paw widths are rear ankle widths of affected and unaffected joints were measured three times a week using a constant tension caliper. Limbs were clinically evaluated and graded on a scale from 0–4 (with 4 being the highest).

Oligonucleotide 25302 (SEQ ID NO. 128) was compared to a saline control. The antisense TNF-α oligonucleotide reduced the incidence of CIA from 70% for the saline control to 40% for the oligonucleotide. The severity of the disease (based on the mean score of the limbs) was also reduced from 3.2 for the saline control to 2.1 for the oligonucleotide.

Example 13

Effect of TNF-α Antisense Oligonucleotides in a Murine Model for Contact Sensitivity Contact sensitivity is a type of immune response resulting from contact of the surface of the skin with a sensitizing chemical. A murine model for contact sensitivity is widely used to develop therapies for chronic inflammation, autoimmune disorder, and organ transplant rejection (Goebeler, M., et al., *Int Arch. Allergy Appl. Immunol.*, 1990, 93, 294–299). One example of such a disease is atopic dermatitis. Female Balb/c mice between the ages of 8 and 12 weeks are used to assess the activity of TNF-α antisense oligonucleotides in a contact sensitivity model.

Balb/c mice receive injections of oligonucleotide drug in saline via i.v. injection into the tail vein. The abdomen of the mice is shaved using an Oster hair clipper. The animals are anesthesized using isoflurane, and 25 µl of 0.2% 2,4-dinitrofluorobenzene (DNFB) in 4:1 acetone:olive oil is applied to the shaved abdomen two days in a row. After five days, 10 ml of 0.2% DNFB in the same vehicle is applied to the right ear. After each exposure, the mouse is suspended in air for two minutes to allow the DNFB to absorb into the skin. 24 and 48 hours after application of DNFB to the ear, the ear thickness is measured using a micrometer. Inflammation (dermatitis) is indicated by a ranked thickening of the ear. Thickness of the treated ear is compared to untreated (contralateral) ear thickness.

Example 14

Effect of TNF-α Antisense Oligonucleotides in a Murine Model for Crohn's Disease C3H/HeJ, SJL/JK and IL10−/− mice are used in a TNBS (2,4,5,-trinitrobenzene sulfonic acid) induced colitis model for Crohn's disease (Neurath, M. F., et al., *J. Exp. Med.*, 1995, 182, 1281–1290). Mice between the ages of 6 weeks and 3 months are used to assess the activity of TNF-α antisense oligonucleotides.

C3H/HeJ, SJL/JK and IL10−/− mice are fasted overnight prior to administration of TNBS. A thin, flexible polyethylene tube is slowly inserted into the colon of the mice so that the tip rests approximately 4 cm proximal to the anus. 0.5 mg of the TNBS in 50% ethanol is slowly injected from the catheter fitted onto a 1 ml syringe. Animals are held inverted in a vertical position for approximately 30 seconds. TNF-α antisense oligonucleotides are administered either at the first sign of symptoms or simultaneously with induction of disease.

Animals, in most cases, are dosed every day. Administration is by i.v., i.p., s.q., minipumps or intracolonic injection. Experimental tissues are collected at the end of the treatment regimen for histochemical evaluation.

Example 15

Effect of TNF-α Antisense Oligonucleotides in a Murine Model for Multiple Sclerosis Experimental autoimmune encephalomyelitis (EAE) is a commonly accepted murine model for multiple sclerosis (Myers, K. J., et al., *J. Neuroimmunol.*, 1992, 41, 1–8). SJL/H, PL/J, (SJLxPL/J)F1, (SJLxBalb/c)F1 and Balb/c female mice between the ages of 6 and 12 weeks are used to test the activity of TNF-α antisense oligonucleotides.

The mice are immunized in the two rear foot pads and base of the tail with an emulsion consisting of encephalitogenic protein or peptide (according to Myers, K. J., et al., *J. of Immunol.*, 1993, 151, 2252–2260) in Complete Freund's Adjuvant supplemented with heat killed Mycobacterium tuberculosis. Two days later, the mice receive an intravenous injection of 500 ng Bordatella pertussis toxin and additional adjuvant.

Alternatively, the disease may also be induced by the adoptive transfer of T-cells. T-cells are obtained from the draining of the lymph nodes of mice immunized with encephalitogenic protein or peptide in CFA. The T cells are grown in tissue culture for several days and then injected intravenously into naive syngeneic recipients.

Mice are monitored and scored daily on a 0–5 scale for signals of the disease, including loss of tail muscle tone, wobbly gait, and various degrees of paralysis.

Example 16

Effect of TNF-α Antisense Oligonucleotides in a Murine Model for Pancreatitis

Swiss Webster, C57BL/56, C57BL/6 lpr and gld male mice are used in an experimental pancreatitis model (Niederau, C., et al., *Gastroenterology*, 1985, 88, 1192–1204). Mice between the ages of 4 and 10 weeks are used to assess the activity of TNF-α antisense oligonucleotides.

Caerulin (5–200 μg/kg) is administered i.p. every hour for one to six hours. At varying time intervals, the mice are given i.p. injection of avertin and bled by cardiac puncture. The pancreas and spleen are evaluated for histopathology and increased levels of IL-1β, IL-6, and TNF-α. The blood is analyzed for increased levels of serum amylase and lipase. TNF-α antisense oligonucleotides are administered by intraperitoneal injection at 4 hours pre-caerulin injections.

Example 17

Effect of TNF-α Antisense Oligonucleotides in a Murine Model for Hepatitis

Concanavalin A-induced hepatitis is used as a murine model for hepatitis (Mizuhara, H., et al., *J. Exp. Med.*, 1994, 179, 1529–1537). It has been shown that this type of liver injury is mediated by Fas (Seino, K., et al., *Gastroenterology* 1997, 113, 1315–1322). Certain types of viral hepatitis, including Hepatitis C, are also mediated by Fas (*J. Gastroenterology and Hepatology*, 1997, 12, S223–S226). Female Balb/c and C57BL/6 mice between the ages of 6 weeks and 3 months are used to assess the activity of TNF-α antisense oligonucleotides.

Mice are intravenenously injected with oligonucleotide. The pretreated mice are then intravenously injected with 0.3 mg concanavalin A (Con A) to induce liver injury. Within 24 hours following Con A injection, the livers are removed from the animals and analyzed for cell death (apoptosis) by in vitro methods. In some experiments, blood is collected from the retro-orbital vein.

Example 18

Effect of Antisense Oligonucleotide Targeted to TNF-α on Survival in Murine Heterotopic Heart Transplant Model To determine the therapeutic effects of TNF-α antisense oligonucleotides in preventing allograft rejection, murine TNF-α-specific oligonucleotides are tested for activity in a murine vascularized heterotopic heart transplant model. Hearts from Balb/c mice are transplanted into the abdominal cavity of C3H mice as primary vascularized grafts essentially as described by Isobe et al., *Circulation* 1991, 84, 1246–1255. Oligonucleotide is administered by continuous intravenous administration via a 7-day Alzet pump. The mean survival time for untreated mice is usually approximately 9–10 days. Treatment of the mice for 7 days with TNF-α antisense oligonucleotides is expected to increase the mean survival time.

Example 19

Optimization of Human TNF-α Antisense Oligonucleotide

Additional antisense oligonucleotides targeted to intron 1 of human TNF-α were designed. These are shown in Table 26. Oligonucleotides are screened by RT-PCR as described in Example 5 hereinabove.

TABLE 26

Nucleotide Sequences of Human TNF-αIntron 1 Antisense Oligonucleotides

| ISIS NO. | NUCLEOTIDE SEQUENCE[1] (5' -> 3') | SEQ ID NO | TARGET GENE NUCLEOTIDE CO-NUCLEOTIDE | GENE TARGET REGION |
|---|---|---|---|---|
| 100181 | AGTGTCTTCTGTGTGCCAGA | 144 | 1409–1428 | intron 1 |
| 100201 | AGTGTCTTCTGTGTGCCAGA | " | " | intron 1 |
| 100230 | AGTGTCTTCTGTGTGCCAGA | " | " | intron 1 |
| 100250 | AGTGTCTTCTGTGTGCCAGA | " | " | intron 1 |
| 100182 | GTGTCTTCTGTGTGCCAGAC | 145 | 1408–1427 | intron 1 |
| 100202 | GTGTCTTCTGTGTGCCAGAC | " | " | intron 1 |
| 100231 | GTGTCTTCTGTGTGCCAGAC | " | " | intron 1 |
| 100251 | GTGTCTTCTGTGTGCCAGAC | " | " | intron 1 |
| 100183 | TGTCTTCTGTGTGCCAGACA | 146 | 1407–1426 | intron 1 |
| 100203 | TGTCTTCTGTGTGCCAGACA | " | " | intron 1 |
| 100232 | TGTCTTCTGTGTGCCAGACA | " | " | intron 1 |
| 100252 | TGTCTTCTGTGTGCCAGACA | " | " | intron 1 |
| 100184 | GTCTTCTGTGTGCCAGACAC | 147 | 1406–1425 | intron 1 |
| 100204 | GTCTTCTGTGTGCCAGACAC | " | " | intron 1 |
| 100233 | GTCTTCTGTGTGCCAGACAC | " | " | intron 1 |
| 100253 | GTCTTCTGTGTGCCAGACAC | " | " | intron 1 |
| 100185 | TCTTCTGTGTGCCAGACACC | 148 | 1405–1424 | intron 1 |
| 100205 | TCTTCTGTGTGCCAGACACC | " | " | intron 1 |
| 100234 | TCTTCTGTGTGCCAGACACC | " | " | intron 1 |
| 100254 | TCTTCTGTGTGCCAGACACC | " | " | intron 1 |
| 100186 | CTTCTGTGTGCCAGACACCC | 149 | 1404–1423 | intron 1 |
| 100206 | CTTCTGTGTGCCAGACACCC | " | " | intron 1 |
| 100235 | CTTCTGTGTGCCAGACACCC | " | " | intron 1 |
| 100255 | CTTCTGTGTGCCAGACACCC | " | " | intron 1 |
| 100187 | TTCTGTGTGCCAGACACCCT | 150 | 1403–1422 | intron 1 |
| 100207 | TTCTGTGTGCCAGACACCCT | " | " | intron 1 |
| 100236 | TTCTGTGTGCCAGACACCCT | " | " | intron 1 |
| 100256 | TTCTGTGTGCCAGACACCCT | " | " | intron 1 |
| 100188 | TCTGTGTGCCAGACACCCTA | 151 | 1402–1421 | intron 1 |
| 100208 | TCTGTGTGCCAGACACCCTA | " | " | intron 1 |
| 100237 | TCTGTGTGCCAGACACCCTA | " | " | intron 1 |
| 100257 | TCTGTGTGCCAGACACCCTA | " | " | intron 1 |
| 100189 | CTGTGTGCCAGACACCCTAT | 152 | 1401–1420 | intron 1 |
| 100209 | CTGTGTGCCAGACACCCTAT | " | " | intron 1 |
| 100238 | CTGTGTGCCAGACACCCTAT | " | " | intron 1 |
| 100258 | CTGTGTGCCAGACACCCTAT | " | " | intron 1 |

TABLE 26-continued

Nucleotide Sequences of Human TNF-αIntron 1 Antisense Oligonucleotides

| ISIS NO. | NUCLEOTIDE SEQUENCE[1] (5' -> 3') | SEQ ID NO | TARGET GENE NUCLEOTIDE CO-ORDINATES[2] | GENE TARGET REGION |
|---|---|---|---|---|
| 100190 | TGTGTGCCAGACACCCTATC | 153 | 1400–1419 | intron 1 |
| 100210 | TGTGTGCCAGACACCCTATC | " | " | intron 1 |
| 100239 | TGTGTGCCAGACACCCTATC | " | " | intron 1 |
| 100259 | TGTGTGCCAGACACCCTATC | " | " | intron 1 |
| 100191 | TGTGCCAGACACCCTATCTT | 154 | 1398–1417 | intron 1 |
| 100211 | TGTGCCAGACACCCTATCTT | " | " | intron 1 |
| 100240 | TGTGCCAGACACCCTATCTT | " | " | intron 1 |
| 100260 | TGTGCCAGACACCCTATCTT | " | intron 1 |   |
| 100192 | GTGCCAGACACCCTATCTTC | 155 | 1397–1416 | intron 1 |
| 100212 | GTGCCAGACACCCTATCTTC | " | " | intron 1 |
| 100241 | GTGCCAGACACCCTATCTTC | " | " | intron 1 |
| 100261 | GTGCCAGACACCCTATCTTC | " | " | intron 1 |
| 100193 | TGCCAGACACCCTATCTTCT | 156 | 1396–1415 | intron 1 |
| 100213 | TGCCAGACACCCTATCTTCT | " | " | intron 1 |
| 100242 | TGCCAGACACCCTATCTTCT | " | " | intron 1 |
| 100262 | TGCCAGACACCCTATCTTCT | " | " | intron 1 |
| 100194 | GCCAGACACCCTATCTTCTT | 157 | 1395–1414 | intron 1 |
| 100214 | GCCAGACACCCTATCTTCTT | " | " | intron 1 |
| 100243 | GCCAGACACCCTATCTTCTT | " | " | intron 1 |
| 100263 | GCCAGACACCCTATCTTCTT | " | " | intron 1 |
| 100195 | CCAGACACCCTATCTTCTTC | 158 | 1394–1413 | intron 1 |
| 100215 | CCAGACACCCTATCTTCTTC | " | " | intron 1 |
| 100244 | CCAGACACCCTATCTTCTTC | " | " | intron 1 |
| 100264 | CCAGACACCCTATCTTCTTC | " | " | intron 1 |
| 100196 | CAGACACCCTATCTTCTTCT | 159 | 1393–1412 | intron 1 |
| 100216 | CAGACACCCTATCTTCTTCT | " | " | intron 1 |
| 100245 | CAGACACCCTATCTTCTTCT | " | " | intron 1 |
| 100265 | CAGACACCCTATCTTCTTCT | " | " | intron 1 |
| 100197 | AGACACCCTATCTTCTTCTC | 160 | 1392–1411 | intron 1 |
| 100217 | AGACACCCTATCTTCTTCTC | " | " | intron 1 |
| 100246 | AGACACCCTATCTTCTTCTC | " | " | intron 1 |
| 100266 | AGACACCCTATCTTCTTCTC | " | " | intron 1 |
| 100198 | GACACCCTATCTTCTTCTCT | 161 | 1391–1410 | intron 1 |
| 100218 | GACACCCTATCTTCTTCTCT | " | " | intron 1 |
| 100247 | GACACCCTATCTTCTTCTCT | " | " | intron 1 |
| 100267 | GACACCCTATCTTCTTCTCT | " | " | intron 1 |
| 100199 | ACACCCTATCTTCTTCTCTC | 162 | 1390–1409 | intron 1 |
| 100219 | ACACCCTATCTTCTTCTCTC | " | " | intron 1 |
| 100248 | ACACCCTATCTTCTTCTCTC | " | " | intron 1 |
| 100268 | ACACCCTATCTTCTTCTCTC | " | " | intron 1 |
| 100200 | CACCCTATCTTCTTCTCTCC | 163 | 1389–1408 | intron 1 |
| 100220 | CACCCTATCTTCTTCTCTCC | " | " | intron 1 |
| 100249 | CACCCTATCTTCTTCTCTCC | " | " | intron 1 |
| 100269 | CACCCTATCTTCTTCTCTCC | " | " | intron 1 |
| 100270 | GTCTTCTGTGTGCCAGAC | 164 | 1408–1425 | intron 1 |
| 100271 | TCTTCTGTGTGCCAGACA | 165 | 1407–1424 | intron 1 |
| 100272 | CTTCTGTGTGCCAGACAC | 166 | 1406–1423 | intron 1 |
| 100273 | TTCTGTGTGCCAGACACC | 167 | 1405–1422 | intron 1 |
| 100274 | TCTGTGTGCCAGACACCC | 168 | 1404–1421 | intron 1 |
| 100275 | CTGTGTGCCAGACACCCT | 169 | 1403–1420 | intron 1 |
| 100276 | TGTGTGCCAGACACCCTA | 170 | 1402–1419 | intron 1 |
| 100277 | GTGTGCCAGACACCCTAT | 171 | 1401–1418 | intron 1 |
| 100278 | TGTGCCAGACACCCTATC | 172 | 1400–1417 | intron 1 |
| 100279 | TGCCAGACACCCTATCTT | 173 | 1398–1415 | intron 1 |
| 100280 | GCCAGACACCCTATCTTC | 174 | 1397–1414 | intron 1 |
| 100281 | CCAGACACCCTATCTTCT | 175 | 1396–1413 | intron 1 |
| 100282 | CAGACACCCTATCTTCTT | 176 | 1395–1412 | intron 1 |
| 100283 | AGACACCCTATCTTCTTC | 177 | 1394–1411 | intron 1 |
| 100284 | GACACCCTATCTTCTTCT | 178 | 1393–1410 | intron 1 |
| 100285 | ACACCCTATCTTCTTCTC | 179 | 1392–1409 | intron 1 |

[1]Emboldened residues are 2'-methoxyethoxy residue (others are 2'-deoxy-). All 2'methoxyethyl cytosines and 2'-deoxy cytosines residues are 5-methyl-cytosines; all linkages are phosphorothioate linkages
[2]Co-ordinates from Genbank Accession No. X02910, locus name "HSTNEA", SEQ ID NO. 1.

Example 20

Design of Antisense Oligonucleotides Targeting Human TNF-α Intron 2

Additional antisense oligonucleotides targeted to intron 2 and coding regions of human TNF-α were designed. These are shown in Table 27. Oligonucleotides are screened by RT-PCR as described in Example 5 hereinabove.

TABLE 27

Nucleotide Sequences of Human TNF-αIntron 2 Antisense Oligonucleotides

| ISIS NO. | NUCLEOTIDE SEQUENCE[1] (5' -> 3') | SEQ ID NO | TARGET GENE NUCLEOTIDE CO-NUCLEOTIDE | GENE TARGET REGION |
|---|---|---|---|---|
| 100549 | AGAGGTTTGGAGACACTTAC | 180 | 1635–1654 | intron 2 |
| 100566 | AGAGGTTTGGAGACACTTAC | " | " | intron 2 |
| 100550 | GAATTAGGAAAGAGGTTTGG | 181 | 1645–1664 | intron 2 |
| 100567 | GAATTAGGAAAGAGGTTTGG | " | " | intron 2 |
| 100551 | CCCAAACCCAGAATTAGGAA | 182 | 1655–1674 | intron 2 |
| 100568 | CCCAAACCCAGAATTAGGAA | " | " | intron 2 |
| 100552 | TACCCCCAAACCCAAACCCA | 183 | 1665–1684 | intron 2 |
| 100569 | TACCCCCAAACCCAAACCCA | " | " | intron 2 |
| 100553 | GTACTAACCCTACCCCCAAA | 184 | 1675–1694 | intron 2 |
| 100570 | GTACTAACCCTACCCCCAAA | " | " | intron 2 |
| 100554 | TTCCATACCGGTACTAACCC | 185 | 1685–1704 | intron 2 |
| 100571 | TTCCATACCGGTACTAACCC | " | " | intron 2 |
| 100555 | CCCCCACTGCTTCCATACCG | 186 | 1695–1714 | intron 2 |
| 100572 | CCCCCACTGCTTCCATACCG | " | " | intron 2 |
| 100556 | CTTTAAATTTCCCCCACTGC | 187 | 1705–1724 | intron 2 |
| 100573 | CTTTAAATTTCCCCCACTGC | " | " | intron 2 |
| 100557 | AAGACCAAAACTTTAAATTT | 188 | 1715–1734 | intron 2 |
| 100571 | AAGACCAAAACTTTAAATTT | " | " | intron 2 |
| 100558 | ATCCTCCCCCAAGACCAAAA | 189 | 1725–1744 | intron 2 |
| 100640 | ATCCTCCCCCAAGACCAAAA | " | " | intron 2 |
| 100559 | ACCTCCATCCATCCTCCCCC | 190 | 1735–1754 | intron 2 |
| 100641 | ACCTCCATCCATCCTCCCCC | " | " | intron 2 |
| 100560 | CCCTACTTTCACCTCCATCC | 191 | 1745–1764 | intron 2 |
| 100642 | CCCTACTTTCACCTCCATCC | " | " | intron 2 |
| 100561 | GAAAATACCCCCCTACTTTC | 192 | 1755–1774 | intron 2 |
| 100643 | GAAAATACCCCCCTACTTTC | " | " | intron 2 |
| 100562 | AAACTTCCTAGAAAATACCC | 193 | 1765–1784 | intron 2 |
| 100644 | AAACTTCCTAGAAAATACCC | " | " | intron 2 |
| 100563 | TGAGACCCTTAAACTTCCTA | 194 | 1775–1794 | intron 2 |
| 100645 | TGAGACCCTTAAACTTCCTA | " | " | intron 2 |
| 100564 | AAGAAAAAGCTGAGACCCTT | 195 | 1785–1804 | intron 2 |
| 100646 | AAGAAAAAGCTGAGACCCTT | " | " | intron 2 |
| 100565 | GGAGAGAGAAAAGAAAAAGC | 196 | 1795–1814 | intron 2 |
| 100647 | GGAGAGAGAAAAGAAAAAGC | " | " | intron 2 |
| 100575 | TGAGCCAGAAGAGGTTGAGG | 197 | 2665–2684 | coding |
| 100576 | ATTCTCTTTTGAGCCAGAA | 198 | 2675–2694 | coding |
| 100577 | TAAGCCCCCAATTCTCTTTT | 199 | 2685–2704 | coding |
| 100578 | GTTCCGACCCTAAGCCCCCA | 200 | 2695–2714 | coding |
| 100579 | CTAAGCTTGGGTTCCGACCC | 201 | 2705–2724 | coding |
| 100580 | GCTTAAAGTTCTAAGCTTGG | 202 | 2715–2734 | coding |
| 100581 | TGGTCTTGTTGCTTAAAGTT | 203 | 2725–2744 | coding |
| 100582 | TTCGAAGTGGTGGTCTTGTT | 204 | 2735–2754 | coding |
| 100583 | AATCCCAGGTTTCGAAGTGG | 205 | 2745–2764 | coding |
| 100584 | CACATTCCTGAATCCCAGGT | 206 | 2755–2774 | coding |
| 100585 | GTGCAGGCCACACATTCCTG | 207 | 2765–2784 | coding |
| 100586 | GCACTTCACTGTGCAGGCCA | 208 | 2775–2794 | coding |
| 100587 | GTGGTTGCCAGCACTTCACT | 209 | 2785–2804 | coding |
| 100588 | TGAATTCTTAGTGGTTGCCA | 210 | 2795–2814 | coding |
| 100589 | GGCCCCAGTTTGAATTCTTA | 211 | 2805–2824 | coding |
| 100590 | GAGTTCTGGAGGCCCCAGTT | 212 | 2815–2834 | coding |
| 100591 | AGGCCCCAGTGAGTTCTGGA | 32 | 2825–2844 | coding |
| 100592 | TCAAAGCTGTAGGCCCCAGT | 214 | 2835–2854 | coding |
| 100593 | ATGTCAGGGATCAAAGCTGT | 215 | 2845–2864 | coding |
| 100594 | CAGATTCCAGATGTCAGGGA | 216 | 2855–2874 | coding |
| 100595 | CCCTGGTCTCCAGATTCCAG | 217 | 2865–2884 | coding |
| 100596 | ACCAAAGGCTCCCTGGTCTC | 218 | 2875–2894 | coding |

TABLE 27-continued

Nucleotide Sequences of Human TNF-αIntron 2 Antisense Oligonucleotides

| ISIS NO. | NUCLEOTIDE SEQUENCE[1] (5' -> 3') | SEQ ID NO | TARGET GENE NUCLEOTIDE CO-NUCLEOTIDE | GENE TARGET REGION |
|---|---|---|---|---|
| 100597 | TCTGGCCAGAACCAAAGGCT | 219 | 2885–2904 | coding |
| 100598 | CCTGCAGCATTCTGGCCAGA | 220 | 2895–2914 | coding |
| 100599 | CTTCTCAAGTCCTGCAGCAT | 221 | 2905–2924 | coding |
| 100600 | TAGGTGAGGTCTTCTCAAGT | 222 | 2915–2934 | coding |
| 100601 | TGTCAATTTCTAGGTGAGGT | 223 | 2925–2944 | coding |
| 100602 | GGTCCACTTGTGTCAATTTC | 224 | 2935–2954 | coding |
| 100603 | GAAGGCCTAAGGTCCACTTG | 225 | 2945–2964 | coding |
| 100604 | CTGGAGAGAGGAAGGCCTAA | 226 | 2955–2974 | coding |
| 100605 | CTGGAAACATCTGGAGAGAG | 227 | 2965–2984 | coding |
| 100606 | TCAAGGAAGTCTGGAAACAT | 228 | 2975–2994 | coding |
| 100607 | GCTCCGTGTCTCAAGGAAGT | 229 | 2985–3004 | coding |
| 100608 | ATAAATACATTCATCTGTAA | 230 | 3085–3104 | coding |
| 100609 | GGTCTCCCAAATAAATACAT | 231 | 3095–3114 | coding |
| 100610 | AGGATACCCCGGTCTCCCAA | 232 | 3105–3124 | coding |
| 100611 | TGGGTCCCCCAGGATACCCC | 35 | 3115–3134 | coding |
| 100612 | GCTCCTACATTGGGTCCCCC | 234 | 3125–3144 | coding |
| 100613 | AGCCAAGGCAGCTCCTACAT | 235 | 3135–3154 | coding |
| 100614 | AACATGTCTGAGCCAAGGCA | 236 | 3145–3164 | coding |
| 100615 | TTTCACGGAAAACATGTCTG | 237 | 3155–3174 | coding |
| 100616 | TCAGCTCCGTTTTCACGGAA | 238 | 3165–3184 | coding |
| 100617 | AGCCTATTGTTCAGCTCCGT | 239 | 3175–3194 | coding |
| 100618 | ACATGGAACAGCCTATTGT | 240 | 3185–3204 | coding |
| 100619 | ATCAAAAGAAGGCACAGAGG | 241 | 3215–3234 | coding |
| 100620 | GTTTAGACAACTTAATCAGA | 242 | 3255–3274 | coding |
| 100621 | AATCAGCATTGTTTAGACAA | 243 | 3265–3284 | coding |
| 100622 | TTGGTCACCAAATCAGCATT | 244 | 3275–3294 | coding |
| 100623 | TGAGTGACAGTTGGTCACCA | 245 | 3285–3304 | coding |
| 100624 | GGCTCAGCAATGAGTGACAG | 246 | 3295–3314 | coding |
| 100625 | ATTACAGACACAACTCCCCT | 247 | 3325–3344 | coding |
| 100626 | TAGTAGGGCGATTACAGACA | 248 | 3335–3354 | coding |
| 100627 | CGCCACTGAATAGTAGGGCG | 249 | 3345–3364 | coding |
| 100628 | CTTTATTTCTCGCCACTGAA | 250 | 3355–3374 | coding |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. X02910, locus name "HSTNFA", SEQ ID NO.1.

Several of these oligonucleotides were chosen for dose response studies. Cells were grown and treated as described in Example 3. Results are shown in Table 28. Each oligonucleotide tested showed a dose response curve with maximum inhibition greater than 75%.

TABLE 28

Dose Response of PMA-Induced neoHK Cells to TNF-α Antisense Oligonucleotides (ASOs)

| ISIS # | SEQ ID NO: | ASO Gene Target | Dose | % protein Expression | % protein Inhibition |
|---|---|---|---|---|---|
| induced | — | — | — | 100% | — |
| 100235 | 149 | intron 1 | 75 nM | 77% | 23% |
| " | " | " | 150 nM | 25% | 75% |
| " | " | " | 300 nM | 6% | 94% |
| 100243 | 157 | intron 1 | 75 nM | 68% | 32% |
| " | " | " | 150 nM | 15% | 85% |
| " | " | " | 300 nM | 6% | 94% |
| 100263 | 157 | intron 1 | 75 nM | 79% | 21% |
| " | " | " | 150 nM | 30% | 70% |
| " | " | " | 300 nM | 23% | 77% |

Example 21

Optimization of Human TNF-α Antisense Oligonucleotide Chemistry

Analogs of oligonucleotides 21820 (SEQ ID NO. 66) and 21823 (SEQ ID NO. 69) were designed and synthesized to find an optimum gap size. The sequences and chemistries are shown in Table 29.

Dose response experiments were performed as described in Example 3. Results are shown in Table 30.

TABLE 29

Nucleotide Sequences of TNF-αChimeric Backbone (deoxy gapped) Oligonucleotides

| ISIS NO. | NUCLEOTIDE SEQUENCE[1] (5' -> 3') | SEQ ID NO | TARGET GENE NUCLEOTIDE CO-NUCLEOTIDE | GENE TARGET REGION |
|---|---|---|---|---|
| 21820 | ATATTTCCCGCTCTTTCTGT | 66 | 1339–1358 | intron 1 |
| 28086 | ATATTTCCCGCTCTTTCTGT | " | " | " |
| 28087 | ATATTTCCCGCTCTTTCTGT | " | " | " |
| 21823 | GTGTGCCAGACACCCTATCT | 69 | 1399–1418 | intron 1 |
| 28088 | GTGTGCCAGACACCCTATCT | " | " | " |
| 28089 | GTGTGCCAGACACCCTATCT | " | " | " |

[1]Emboldened residues are 2'-methoxyethoxy residues (others are 2'-deoxy-). All 2'-methoxyethoxy cytidines and 2'-deoxycytidines are 5-methyl-cytidines; all linkages are phosphorothioate linkages.
[2]Co-ordinates from Genbank Accession No. X02910, locus name "HSTNFA ", SEQ ID NO.1.

TABLE 30

Dose Response of 20 Hour PMA-Induced neoHK Cells to TNF-α Chimeric (deoxy gapped) Antisense Oligonucleotides (ASOs)

| ISIS # | SEQ ID NO: | ASO Gene Target | Dose | % protein Expression | % protein Inhibition |
|---|---|---|---|---|---|
| induced | — | — | — | 100% | — |
| 13393 | 49 | control | 75 nM | 150.0% | — |
| " | " | " | 150 nM | 135.0% | — |
| " | " | " | 300 nM | 90.0% | 10.0% |
| 21820 | 66 | intron 1 | 75 nM | 65.0% | 35.0% |
| " | " | " | 150 nM | 28.0% | 72.0% |
| " | " | " | 300 nM | 9.7% | 90.3% |
| 28086 | 66 | intron 1 | 75 nM | 110.0% | — |
| " | " | " | 150 nM | 83.0% | 17.0% |
| " | " | " | 300 nM | 61.0% | 39.0% |
| 28087 | 66 | intron 1 | 75 nM | 127.0% | — |
| " | " | " | 150 nM | 143.0% | — |
| " | " | " | 300 nM | 147.0% | — |
| 21823 | 69 | intron 1 | 75 nM | 35.0% | 65.0% |
| " | " | " | 150 nM | 30.0% | 70.0% |
| " | " | " | 300 nM | 6.4% | 93.6% |
| 28088 | 69 | intron 1 | 75 nM | 56.0% | 44.0% |
| " | " | " | 150 nM | 26.0% | 74.0% |
| " | " | " | 300 nM | 11.0% | 89.0% |
| 28089 | 69 | intron 1 | 75 nM | 76.0% | 24.0% |
| " | " | " | 150 nM | 53.0% | 47.0% |
| " | " | " | 300 nM | 23.0% | 77.0% |

Example 22

Screening of Additional TNF-α Chimeric (Deoxy Gapped) Antisense Oligonucleotides Additional oligonucleotides targeting the major regions of TNF-α were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 31.

Oligonucleotides were screened as described in Example 5. Results are shown in Table 32.

TABLE 31

Nucleotide Sequence of Additional Human TNF-α Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104649 | CTGAGGGAGCGTCTGCTGGC | 251 | 0616–0635 | 5'-UTR |
| 104650 | CCTTGCTGAGGGAGCGTCTG | 252 | 0621–0640 | 5'-UTR |
| 104651 | CTGGTCCTCTGCTGTCCTTG | 253 | 0636–0655 | 5'-UTR |
| 104652 | CCTCTGCTGTCCTTGCTGAG | 254 | 0631–0650 | 5'-UTR |
| 104653 | TTCTCTCCCTCTTAGCTGGT | 255 | 0651–0670 | 5'-UTR |
| 104654 | TCCCTCTTAGCTGGTCCTCT | 256 | 0646–0665 | 5'-UTR |
| 104655 | TCTGAGGGTTGTTTTCAGGG | 257 | 0686–0705 | 5'-UTR |
| 104656 | CTGTAGTTGCTTCTCTCCCT | 258 | 0661–0680 | 5'-UTR |
| 104657 | ACCTGCCTGGCAGCTTGTCA | 259 | 0718–0737 | 5'-UTR |
| 104658 | GGATGTGGCGTCTGAGGGTT | 260 | 0696–0715 | 5'-UTR |
| 104659 | TGTGAGAGGAAGAGAACCTG | 261 | 0733–0752 | 5'-UTR |
| 104660 | GAGGAAGAGAACCTGCCTGG | 262 | 0728–0747 | 5'-UTR |
| 104661 | AGCCGTGGGTCAGTATGTGA | 263 | 0748–0767 | 5'-UTR |
| 104662 | TGGGTCAGTATGTGAGAGGA | 264 | 0743–0762 | 5'-UTR |
| 104663 | GAGAGGGTGAAGCCGTGGGT | 265 | 0758–0777 | 5'-UTR |
| 104664 | TCATGGTGTCCTTTCCAGGG | 266 | 0780–0799 | AUG |

TABLE 31-continued

Nucleotide Sequence of Additional Human TNF-α
Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104665 | CTTTCAGTGCTCATGGTGTC | 267 | 0790–0809 | AUG |
| 104666 | TCATGCTTTCAGTGCTCATG | 268 | 0795–0814 | AUG |
| 104667 | ACGTCCCGGATCATGCTTTC | 269 | 0805–0824 | coding |
| 104668 | GCTCCACGTCCCGGATCATG | 270 | 0810–0829 | coding |
| 104669 | TCCTCGGCCAGCTCCACGTC | 271 | 0820–0839 | coding |
| 104670 | GCGCCTCCTCGGCCAGCTCC | 272 | 0825–0844 | coding |
| 104671 | AGGAACAAGCACCGCCTGGA | 273 | 0874–0893 | coding |
| 104672 | CAAGCACCGCCTGGAGCCCT | 274 | 0869–0888 | coding |
| 104673 | AAGGAGAAGAGGCTGAGGAA | 275 | 0889–0908 | coding |
| 104674 | GAAGAGGCTGAGGAACAAGC | 276 | 0884–0903 | coding |
| 104675 | CCTGCCACGATCAGGAAGGA | 277 | 0904–0923 | coding |
| 104676 | CACGATCAGGAAGGAGAAGA | 278 | 0899–0918 | coding |
| 104677 | AAGAGCGTGGTGGCGCCTGC | 279 | 0919–0938 | coding |
| 104678 | CGTGGTGGCGCCTGCCACGA | 280 | 0914–0933 | coding |
| 104679 | AAGTGCAGCAGGCAGAAGAG | 281 | 0934–0953 | coding |
| 104680 | CAGCAGGCAGAAGAGCGTGG | 282 | 0929–0948 | coding |
| 104681 | GATCACTCCAAAGTGCAGCA | 283 | 0944–0963 | coding |
| 104682 | GGGCCGATCACTCCAAAGTG | 284 | 0949–0968 | coding |
| 104683 | GGGCCAGAGGGCTGATTAGA | 285 | 1606–1625 | coding |
| 104684 | AGAGGGCTGATTAGAGAGAG | 286 | 1601–1620 | coding |
| 104685 | GCTACAGGCTTGTCACTCGG | 287 | 1839–1858 | coding |
| 104686 | CTGACTGCCTGGGCCAGAGG | 288 | 1616–1635 | E2/I2[3] |
| 104687 | TACAACATGGGCTACAGGCT | 289 | 1849–1868 | coding |
| 104688 | AGCCACTGGAGCTGCCCCTC | 290 | 2185–2204 | coding |
| 104689 | CTGGAGCTGCCCCTCAGCTT | 291 | 2180–2199 | coding |
| 104690 | TTGGCCCGGCGGTTCAGCCA | 292 | 2200–2219 | coding |
| 104691 | TTGGCCAGGAGGGCATTGGC | 293 | 2215–2234 | coding |
| 104692 | CCGGCGGTTCAGCCACTGGA | 294 | 2195–2214 | coding |
| 104693 | CTCAGCTCCACGCCATTGGC | 295 | 2230–2249 | coding |
| 104694 | CAGGAGGGCATTGGCCCGGC | 296 | 2210–2229 | coding |
| 104695 | CTCCACGCCATTGGCCAGGA | 297 | 2225–2244 | coding |
| 104696 | ACCAGCTGGTTATCTCTCAG | 298 | 2245–2264 | coding |
| 104697 | CTGGTTATCTCTCAGCTCCA | 299 | 2240–2259 | coding |
| 104698 | CCCTCTGATGGCACCACCAG | 300 | 2260–2279 | coding |
| 104699 | TGATGGCACCACCAGCTGGT | 301 | 2255–2274 | coding |
| 104700 | TAGATGAGGTACAGGCCCTC | 302 | 2275–2294 | coding |

TABLE 31-continued

Nucleotide Sequence of Additional Human TNF-α
Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104701 | AAGAGGACCTGGGAGTAGAT | 303 | 2290–2309 | coding |
| 104702 | GAGGTACAGGCCCTCTGATG | 304 | 2270–2289 | coding |
| 104703 | CAGCCTTGGCCCTTGAAGAG | 305 | 2305–2324 | coding |
| 104704 | GACCTGGGAGTAGATGAGGT | 306 | 2285–2304 | coding |
| 104705 | TTGGCCCTTGAAGAGGACCT | 307 | 2300–2319 | coding |
| 104706 | TGGTGTGGGTGAGGAGCACA | 308 | 2337–2356 | coding |
| 104707 | CGGCGATGCGGCTGATGGTG | 309 | 2352–2371 | coding |
| 104708 | TGGGTGAGGAGCACATGGGT | 310 | 2332–2351 | coding |
| 104709 | TGGTCTGGTAGGAGACGGCG | 311 | 2367–2386 | coding |
| 104710 | ATGCGGCTGATGGTGTGGGT | 312 | 2347–2366 | coding |
| 104711 | AGAGGAGGTTGACCTTGGTC | 313 | 2382–2401 | coding |
| 104712 | TGGTAGGAGACGGCGATGCG | 314 | 2362–2381 | coding |
| 104713 | AGGTTGACCTTGGTCTGGTA | 315 | 2377–2396 | coding |
| 104714 | GGCTCTTGATGGCAGAGAGG | 316 | 2397–2416 | coding |
| 104715 | TCATACCAGGGCTTGGCCTC | 317 | 2446–2465 | coding |
| 104716 | TTGATGGCAGAGAGGAGGTT | 318 | 2392–2411 | coding |
| 104717 | CCCAGATAGATGGGCTCATA | 93 | 2461–2480 | coding |
| 104718 | CCAGGGCTTGGCCTCAGCCC | 94 | 2441–2460 | coding |
| 104719 | AGCTGGAAGACCCCTCCCAG | 319 | 2476–2495 | coding |
| 104720 | ATAGATGGGCTCATACCAGG | 320 | 2456–2475 | coding |
| 104721 | CGGTCACCCTTCTCCAGCTG | 321 | 2491–2510 | coding |
| 104722 | GAAGACCCCTCCCAGATAGA | 322 | 2471–2490 | coding |
| 104723 | ATCTCAGCGCTGAGTCGGTC | 26 | 2506–2525 | coding |
| 104724 | ACCCTTCTCCAGCTGGAAGA | 323 | 2486–2505 | coding |
| 104725 | TAGTCGGGCCGATTGATCTC | 90 | 2521–2540 | coding |
| 104726 | AGCGCTGAGTCGGTCACCCT | 91 | 2501–2520 | coding |
| 104727 | TCGGCAAAGTCGAGATAGTC | 324 | 2536–2554 | coding |
| 104728 | GGGCCGATTGATCTCAGCGC | 325 | 2516–2535 | coding |
| 104729 | TAGACCTGCCCAGACTCGGC | 326 | 2551–2570 | coding |
| 104730 | AAAGTCGAGATAGTCGGGCC | 327 | 2531–2550 | coding |
| 104731 | GCAATGATCCCAAAGTAGAC | 328 | 2566–2585 | coding |
| 104732 | CTGCCCAGACTCGGCAAAGT | 329 | 2546–2565 | coding |
| 104733 | CGTCCTCCTCACAGGGCAAT | 330 | 2581–2600 | stop |
| 104734 | GATCCCAAAGTAGACCTGCC | 88 | 2561–2580 | coding |
| 104735 | GGAAGGTTGGATGTTCGTCC | 331 | 2596–2615 | 3'-UTR |
| 104736 | TCCTCACAGGGCAATGATCC | 332 | 2576–2595 | stop |
| 104737 | GTTGAGGGTGTCTGAAGGAG | 333 | 2652–2671 | 3'-UTR |

TABLE 31-continued

Nucleotide Sequence of Additional Human TNF-α
Chimeric (deoxy gapped) Antisense Oligonucleotides

| ISIS NO. | NUCLEOTIDE SEQUENCE[1]<br>(5'->3') | SEQ ID NO: | TARGET GENE NUCLEOTIDE<br>CO-ORDINATES[2] | GENE TARGET<br>REGION |
|---|---|---|---|---|
| 104738 | GTTGGATGTTCGTCCTCCTC | 334 | 2591–2610 | stop |
| 104739 | TTTGAGCCAGAAGAGGTTGA | 335 | 2667–2686 | 3'-UTR |
| 104740 | GAGGCGTTTGGGAAGGTTGG | 336 | 2606–2625 | 3'-UTR |
| 104741 | GCCCCCAATTCTCTTTTTGA | 337 | 2682–2701 | 3'-UTR |
| 104742 | GCCAGAAGAGGTTGAGGGTG | 338 | 2662–2681 | 3'-UTR |
| 104743 | GGGTTCCGACCCTAAGCCCC | 339 | 2697–2716 | 3'-UTR |
| 104744 | CAATTCTCTTTTTGAGCCAG | 340 | 2677–2696 | 3'-UTR |
| 104745 | TAAAGTTCTAAGCTTGGGTT | 341 | 2712–2731 | 3'-UTR |
| 104746 | CCGACCCTAAGCCCCCAATT | 342 | 2692–2711 | 3'-UTR |
| 104747 | GGTGGTCTTGTTGCTTAAAG | 343 | 2727–2746 | 3'-UTR |
| 104748 | TTCTAAGCTTGGGTTCCGAC | 344 | 2707–2726 | 3'-UTR |
| 104749 | CCCAGGTTTCGAAGTGGTGG | 345 | 2742–2761 | 3'-UTR |
| 104750 | TCTTGTTGCTTAAAGTTCTA | 346 | 2722–2741 | 3'-UTR |
| 104751 | CACACATTCCTGAATCCCAG | 347 | 2757–2776 | 3'-UTR |
| 104752 | GTTTCGAAGTGGTGGTCTTG | 348 | 2737–2756 | 3'-UTR |
| 104753 | CTTCACTGTGCAGGCCACAC | 349 | 2772–2791 | 3'-UTR |
| 104754 | ATTCCTGAATCCCAGGTTTC | 350 | 2752–2771 | 3'-UTR |
| 104755 | TAGTGGTTGCCAGCACTTCA | 351 | 2787–2806 | 3'-UTR |
| 104756 | CCCAGTTTGAATTCTTAGTG | 352 | 2802–2821 | 3'-UTR |
| 104757 | CTGTGCAGGCCACACATTCC | 353 | 2767–2786 | 3'-UTR |
| 104758 | GTGAGTTCTGGAGGCCCCAG | 354 | 2817–2836 | 3'-UTR |
| 104759 | GTTGCCAGCACTTCACTGTG | 355 | 2782–2801 | 3'-UTR |
| 104760 | TTTGAATTCTTAGTGGTTGC | 356 | 2797–2816 | 3'-UTR |
| 104761 | AAGCTGTAGGCCCCAGTGAG | 357 | 2832–2851 | 3'-UTR |
| 104762 | TTCTGGAGGCCCCAGTTTGA | 358 | 2812–2831 | 3'-UTR |
| 104763 | AGATGTCAGGGATCAAAGCT | 359 | 2847–2866 | 3'-UTR |
| 104764 | TGGTCTCCAGATTCCAGATG | 360 | 2862–2881 | 3'-UTR |
| 104765 | GTAGGCCCCAGTGAGTTCTG | 361 | 2827–2846 | 3'-UTR |
| 104766 | GAACCAAAGGCTCCCTGGTC | 362 | 2877–2896 | 3'-UTR |
| 104767 | TCAGGGATCAAAGCTGTAGG | 363 | 2842–2861 | 3'-UTR |
| 104768 | TCCAGATTCCAGATGTCAGG | 364 | 2857–2876 | 3'-UTR |
| 104769 | GCAGCATTCTGGCCAGAACC | 365 | 2892–2911 | 3'-UTR |
| 104770 | GTCTTCTCAAGTCCTGCAGC | 366 | 2907–2926 | 3'-UTR |
| 104771 | AAAGGCTCCCTGGTCTCCAG | 367 | 2872–2891 | 3'-UTR |
| 104772 | CAATTTCTAGGTGAGGTCTT | 368 | 2922–2941 | 3'-UTR |
| 104773 | ATTCTGGCCAGAACCAAAGG | 369 | 2887–2906 | 3'-UTR |

TABLE 31-continued

Nucleotide Sequence of Additional Human TNF-α
Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104774 | CTCAAGTCCTGCAGCATTCT | 34 | 2902–2921 | 3'-UTR |
| 104775 | AAGGTCCACTTGTGTCAATT | 370 | 2937–2956 | 3'-UTR |
| 104776 | GAGAGAGGAAGGCCTAAGGT | 371 | 2952–2971 | 3'-UTR |
| 104777 | TCTAGGTGAGGTCTTCTCAA | 372 | 2917–2936 | 3'-UTR |
| 104778 | CCACTTGTGTCAATTTCTAG | 373 | 2932–2951 | 3'-UTR |
| 104779 | GTCTGGAAACATCTGGAGAG | 374 | 2967–2986 | 3'-UTR |
| 104780 | CCGTGTCTCAAGGAAGTCTG | 375 | 2982–3001 | 3'-UTR |
| 104781 | AGGAAGGCCTAAGGTCCACT | 376 | 2947–2966 | 3'-UTR |
| 104782 | GAGGGAGCTGGCTCCATGGG | 377 | 3014–3033 | 3'-UTR |
| 104783 | GAAACATCTGGAGAGAGGAA | 378 | 2962–2981 | 3'-UTR |
| 104784 | GTGCAAACATAAATAGAGGG | 379 | 3029–3048 | 3'-UTR |
| 104785 | TCTCAAGGAAGTCTGGAAAC | 380 | 2977–2996 | 3'-UTR |
| 104786 | AATAAATAATCACAAGTGCA | 381 | 3044–3063 | 3'-UTR |
| 104787 | GGGCTGGGCTCCGTGTCTCA | 382 | 2992–3011 | 3'-UTR |
| 104788 | TACCCCGGTCTCCCAAATAA | 383 | 3101–3120 | 3'-UTR |
| 104789 | AACATAAATAGAGGGAGCTG | 384 | 3024–3043 | 3'-UTR |
| 104790 | TTGGGTCCCCCAGGATACCC | 385 | 3116–3135 | 3'-UTR |
| 104791 | ATAATCACAAGTGCAAACAT | 386 | 3039–3058 | 3'-UTR |
| 104792 | AAGGCAGCTCCTACATTGGG | 387 | 3131–3150 | 3'-UTR |
| 104793 | CGGTCTCCCAAATAAATACA | 388 | 3096–3115 | 3'-UTR |
| 104794 | AAACATGTCTGAGCCAAGGC | 389 | 3146–3165 | 3'-UTR |
| 104795 | TCCCCCAGGATACCCCGGTC | 390 | 3111–3130 | 3'-UTR |
| 104796 | AGCTCCTACATTGGGTCCCC | 391 | 3126–3145 | 3'-UTR |
| 104797 | CTCCGTTTTCACGGAAAACA | 37 | 3161–3180 | 3'-UTR |
| 104798 | TGTCTGAGCCAAGGCAGCTC | 392 | 3141–3160 | 3'-UTR |
| 104799 | CAGCCTATTGTTCAGCTCCG | 393 | 3176–3195 | 3'-UTR |
| 104800 | AGAAGGCACAGAGGCCAGGG | 394 | 3209–3228 | 3'-UTR |
| 104801 | TTTTCACGGAAAACATGTCT | 395 | 3156–3175 | 3'-UTR |
| 104802 | TATTGTTCAGCTCCGTTTTC | 396 | 3171–3190 | 3'-UTR |
| 104803 | AAAACATAATCAAAGAAG | 397 | 3224–3243 | 3'-UTR |
| 104804 | CAGATAAATATTTTAAAAA | 398 | 3239–3258 | 3'-UTR |
| 104805 | TACATGGGAACAGCCTATTG | 399 | 3186–3205 | 3'-UTR |
| 104806 | TTTAGACAACTTAATCAGAT | 400 | 3254–3273 | 3'-UTR |
| 104807 | CATAATCAAAGAAGGCACA | 401 | 3219–3238 | 3'-UTR |
| 104808 | ACCAAATCAGCATTGTTTAG | 402 | 3269–3288 | 3'-UTR |
| 104809 | AAATATTTTAAAAACATAA | 403 | 3234–3253 | 3'-UTR |
| 104810 | GAGTGACAGTTGGTCACCAA | 404 | 3284–3303 | 3'-UTR |

TABLE 31-continued

Nucleotide Sequence of Additional Human TNF-α
Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104811 | ACAACTTAATCAGATAAATA | 405 | 3249–3268 | 3'-UTR |
| 104812 | CAGAGGCTCAGCAATGAGTG | 406 | 3299–3318 | 3'-UTR |
| 104813 | ATCAGCATTGTTTAGACAAC | 407 | 3264–3283 | 3'-UTR |
| 104814 | AGGGCGATTACAGACACAAC | 408 | 3331–3350 | 3'-UTR |
| 104815 | ACAGTTGGTCACCAAATCAG | 409 | 3279–3298 | 3'-UTR |
| 104816 | TCGCCACTGAATAGTAGGGC | 410 | 3346–3365 | 3'-UTR |
| 104817 | GCTCAGCAATGAGTGACAGT | 411 | 3294–3313 | 3'-UTR |
| 104818 | AGCAAACTTTATTTCTCGCC | 412 | 3361–3380 | 3'-UTR |
| 104819 | GATTACAGACACAACTCCCC | 413 | 3326–3345 | 3'-UTR |
| 104820 | ACTGAATAGTAGGGCGATTA | 414 | 3341–3360 | 3'-UTR |
| 104821 | ACTTTATTTCTCGCCACTGA | 415 | 3356–3375 | 3'-UTR |
| 104822 | GCTGTCCTTGCTGAGGGAGC | 416 | 0626–0645 | 5'-UTR |
| 104823 | CTTAGCTGGTCCTCTGCTGT | 417 | 0641–0660 | 5'-UTR |
| 104824 | GTTGCTTCTCTCCCTCTTAG | 418 | 0656–0675 | 5'-UTR |
| 104825 | TGGCGTCTGAGGGTTGTTTT | 419 | 0691–0710 | 5'-UTR |
| 104826 | AGAGAACCTGCCTGGCAGCT | 420 | 0723–0742 | 5'-UTR |
| 104827 | CAGTATGTGAGAGGAAGAGA | 421 | 0738–0757 | 5'-UTR |
| 104828 | GGTGAAGCCGTGGGTCAGTA | 422 | 0753–0772 | 5'-UTR |
| 104829 | AGTGCTCATGGTGTCCTTTC | 423 | 0785–0804 | AUG |
| 104830 | CCGGATCATGCTTTCAGTGC | 424 | 0800–0819 | coding |
| 104831 | GGCCAGCTCCACGTCCCGGA | 425 | 0815–0834 | coding |
| 104832 | GGCCCCCCTGTCTTCTTGGG | 426 | 0847–0866 | coding |
| 104833 | GGCTGAGGAACAAGCACCGC | 427 | 0879–0898 | coding |
| 104834 | TCAGGAAGGAGAAGAGGCTG | 428 | 0894–0913 | coding |
| 104835 | TGGCGCCTGCCACGATCAGG | 429 | 0909–0918 | coding |
| 104836 | GGCAGAAGAGCGTGGTGGCG | 430 | 0924–0943 | coding |
| 104837 | CTCCAAAGTGCAGCAGGCAG | 431 | 0939–0958 | coding |
| 104838 | GCTGATTAGAGAGAGGTCCC | 432 | 1596–1615 | coding |
| 104839 | TGCCTGGGCCAGAGGGCTGA | 433 | 1611–1630 | coding |
| 104840 | GCTGCCCCTCAGCTTGAGGG | 434 | 2175–2194 | coding |
| 104841 | GGTTCAGCCACTGGAGCTGC | 435 | 2190–2209 | coding |
| 104842 | GGGCATTGGCCCGGCGGTTC | 436 | 2205–2224 | coding |
| 104843 | CGCCATTGGCCAGGAGGGCA | 437 | 2220–2239 | coding |
| 104844 | TATCTCTCAGCTCCACGCCA | 438 | 2235–2254 | coding |
| 104845 | GCACCACCAGCTGGTTATCT | 439 | 2250–2269 | coding |
| 104846 | ACAGGCCCTCTGATGGCACC | 440 | 2265–2284 | coding |

TABLE 31-continued

Nucleotide Sequence of Additional Human TNF-α
Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104847 | GGGAGTAGATGAGGTACAGG | 441 | 2280–2299 | coding |
| 104848 | CCTTGAAGAGGACCTGGGAG | 442 | 2295–2314 | coding |
| 104849 | GAGGAGCACATGGGTGGAGG | 443 | 2327–2346 | coding |
| 104850 | GCTGATGGTGTGGGTGAGGA | 444 | 2342–2361 | coding |
| 104851 | GGAGACGGCGATGCGGCTGA | 445 | 2357–2376 | coding |
| 104852 | GACCTTGGTCTGGTAGGAGA | 446 | 2372–2391 | coding |
| 104853 | GGCAGAGAGGAGGTTGACCT | 447 | 2387–2406 | coding |
| 104854 | GCTTGGCCTCAGCCCCCTCT | 23 | 2436–2455 | coding |
| 104855 | TGGGCTCATACCAGGGCTTG | 448 | 2451–2470 | coding |
| 104856 | CCCCTCCCAGATAGATGGGC | 449 | 2466–2485 | coding |
| 104857 | TCTCCAGCTGGAAGACCCCT | 92 | 2481–2500 | coding |
| 104858 | TGAGTCGGTCACCCTTCTCC | 450 | 2496–2515 | coding |
| 104859 | GATTGATCTCAGCGCTGAGT | 451 | 2511–2530 | coding |
| 104860 | CGAGATAGTCGGGCCGATTG | 452 | 2526–2545 | coding |
| 104861 | CAGACTCGGCAAAGTCGAGA | 89 | 2541–2560 | coding |
| 104862 | CAAAGTAGACCTGCCCAGAC | 453 | 2556–2575 | coding |
| 104863 | ACAGGGCAATGATCCCAAAG | 454 | 2571–2590 | stop |
| 104864 | ATGTTCGTCCTCCTCACAGG | 455 | 2586–2605 | stop |
| 104865 | GTTTGGGAAGGTTGGATGTT | 456 | 2601–2620 | 3'-UTR |
| 104866 | AAGAGGTTGAGGGTGTCTGA | 457 | 2657–2676 | 3'-UTR |
| 104867 | CTCTTTTTGAGCCAGAAGAG | 458 | 2672–2691 | 3'-UTR |
| 104868 | CCTAAGCCCCCAATTCTCTT | 459 | 2687–2706 | 3'-UTR |
| 104869 | AGCTTGGGTTCCGACCCTAA | 460 | 2702–2721 | 3'-UTR |
| 104870 | TTGCTTAAAGTTCTAAGCTT | 461 | 2717–2736 | 3'-UTR |
| 104871 | GAAGTGGTGGTCTTGTTGCT | 462 | 2732–2751 | 3'-UTR |
| 104872 | TGAATCCCAGGTTTCGAAGT | 463 | 2747–2766 | 3'-UTR |
| 104873 | CAGGCCACACATTCCTGAAT | 464 | 2762–2781 | 3'-UTR |
| 104874 | CAGCACTTCACTGTGCAGGC | 465 | 2777–2796 | 3'-UTR |
| 104875 | ATTCTTAGTGGTTGCCAGCA | 466 | 2792–2811 | 3'-UTR |
| 104876 | GAGGCCCCAGTTTGAATTCT | 467 | 2807–2826 | 3'-UTR |
| 104877 | CCCCAGTGAGTTCTGGAGGC | 468 | 2822–2841 | 3'-UTR |
| 104878 | GATCAAAGCTGTAGGCCCCA | 469 | 2837–2856 | 3'-UTR |
| 104879 | ATTCCAGATGTCAGGGATCA | 470 | 2852–2871 | 3'-UTR |
| 104880 | CTCCCTGGTCTCCAGATTCC | 471 | 2867–2886 | 3'-UTR |
| 104881 | GGCCAGAACCAAAGGCTCCC | 472 | 2882–2901 | 3'-UTR |
| 104882 | GTCCTGCAGCATTCTGGCCA | 473 | 2897–2916 | 3'-UTR |
| 104883 | GTGAGGTCTTCTCAAGTCCT | 474 | 2912–2931 | 3'-UTR |

TABLE 31-continued

Nucleotide Sequence of Additional Human TNF-α
Chimeric (deoxy gapped) Antisense Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 104884 | TGTGTCAATTTCTAGGTGAG | 475 | 2927–2946 | 3'-UTR |
| 104885 | GGCCTAAGGTCCACTTGTGT | 476 | 2942–2961 | 3'-UTR |
| 104886 | ATCTGGAGAGAGGAAGGCCT | 477 | 2957–2976 | 3'-UTR |
| 104887 | AGGAAGTCTGGAAACATCTG | 478 | 2972–2991 | 3'-UTR |
| 104888 | GGGCTCCGTGTCTCAAGGAA | 479 | 2987–3006 | 3'-UTR |
| 104889 | AAATAGAGGGAGCTGGCTCC | 480 | 3019–3038 | 3'-UTR |
| 104890 | CACAAGTGCAAACATAAAATA | 481 | 3034–3053 | 3'-UTR |
| 104891 | TCCCAAATAAATACATTCAT | 482 | 3091–3110 | 3'-UTR |
| 104892 | CAGGATACCCCGGTCTCCCA | 483 | 3106–3125 | 3'-UTR |
| 104893 | CTACATTGGGTCCCCCAGGA | 484 | 3121–3140 | 3'-UTR |
| 104894 | GAGCCAAGGCAGCTCCTACA | 485 | 3136–3155 | 3'-UTR |
| 104895 | ACGGAAAACATGTCTGAGCC | 486 | 3151–3170 | 3'-UTR |
| 104896 | TTCAGCTCCGTTTTCACGGA | 487 | 3166–3185 | 3'-UTR |
| 104897 | GGGAACAGCCTATTGTTCAG | 488 | 3181–3200 | 3'-UTR |
| 104898 | TCAAAAGAAGGCACAGAGGC | 489 | 3214–3233 | 3'-UTR |
| 104899 | TTTTAAAAAACATAATCAAA | 490 | 3229–3248 | 3'-UTR |
| 104900 | TTAATCAGATAAATATTTTA | 491 | 3244–3263 | 3'-UTR |
| 104901 | CATTGTTTAGACAACTTAAT | 492 | 3259–3278 | 3'-UTR |
| 104902 | TGGTCACCAAATCAGCATTG | 493 | 3274–3293 | 3'-UTR |
| 104903 | GCAATGAGTGACAGTTGGTC | 494 | 3289–3308 | 3'-UTR |
| 104904 | GGGAGCAGAGGCTCAGCAAT | 495 | 3304–3323 | 3'-UTR |
| 104905 | ATAGTAGGGCGATTACAGAC | 496 | 3336–3355 | 3'-UTR |
| 104906 | ATTTCTCGCCACTGAATAGT | 497 | 3351–3370 | 3'-UTR |

[1] Emboldened residues are 2'-O-methoxyethyl residues (others are 2'-deoxy-).
All 2'-O-methoxyethyl cytosines and 2'-deoxy cytosines residues are
5-methyl-cytosines; all linkages are phosphorothioate linkages.
[2] Co-ordinates from Genbank Accession No. X02910, locus name "HSTNFA", SEQ ID NO. 1.
[3] This target region is an exon-intron junction and is represented in the
form, for example, I1/E2, where I, followed by a number, refers to the
intron number and E, followed by a number, refers to the exon number.

TABLE 32

Inhibition of Human TNF-α mRNA Expression by Chimeric
(deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 0.0% | — |
| induced | — | — | 100.0% | 0.0% |
| 28089 | 69 | intron 1 | 42.3% | 57.7% |
| 104649 | 251 | 5'-UTR | 165.6% | — |
| 104650 | 252 | 5'-UTR | 75.8% | 24.2% |
| 104651 | 253 | 5'-UTR | 58.2% | 41.8% |
| 104652 | 254 | 5'-UTR | 114.5% | — |
| 104653 | 255 | 5'-UTR | 84.9% | 15.1% |
| 104654 | 256 | 5'-UTR | 80.8% | 19.2% |
| 104655 | 257 | 5'-UTR | 94.3% | 5.7% |
| 104656 | 258 | 5'-UTR | 78.4% | 21.6% |
| 104657 | 259 | 5'-UTR | 87.4% | 12.6% |

TABLE 32-continued

Inhibition of Human TNF-α mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 104658 | 260 | 5'-UTR | 213.4% | — |
| 104659 | 261 | 5'-UTR | 96.3% | 3.7% |
| 104660 | 262 | 5'-UTR | 153.1% | — |
| 104661 | 263 | 5'-UTR | 90.0% | 10.0% |
| 104662 | 264 | 5'-UTR | 33.3% | 66.7% |
| 104663 | 265 | 5'-UTR | 144.2% | — |
| 104664 | 266 | AUG | 76.3% | 23.7% |
| 104665 | 267 | AUG | 185.3% | — |
| 104666 | 268 | AUG | 67.4% | 32.6% |
| 104667 | 269 | coding | 94.3% | 5.7% |
| 104668 | 270 | coding | 63.1% | 36.9% |
| 104669 | 271 | coding | 50.8% | 49.2% |
| 104670 | 272 | coding | 43.7% | 56.3% |
| 104671 | 273 | coding | 52.2% | 47.8% |
| 104672 | 274 | coding | 51.8% | 48.2% |
| 104673 | 275 | coding | 102.3% | — |
| 104674 | 276 | coding | 135.4% | — |
| 104675 | 277 | coding | 83.1% | 16.9% |
| 104676 | 278 | coding | 87.5% | 12.5% |
| 104677 | 279 | coding | 53.6% | 46.4% |
| 104678 | 280 | coding | 75.2% | 24.8% |
| 104679 | 281 | coding | 114.0% | — |
| 104680 | 282 | coding | 142.5% | — |
| 104681 | 283 | coding | 58.5% | 41.5% |
| 104682 | 284 | coding | 101.9% | — |
| 104683 | 285 | coding | 77.1% | 22.9% |
| 104684 | 286 | coding | 61.0% | 39.0% |
| 104685 | 287 | coding | 65.9% | 34.1% |
| 104686 | 288 | E2/I2 | 59.2% | 40.8% |
| 104687 | 289 | coding | 77.0% | 23.0% |
| 104688 | 290 | coding | 40.1% | 59.9 |
| 104689 | 291 | coding | 78.6% | 21.4% |
| 104690 | 292 | coding | 90.9% | 9.1% |
| 104691 | 293 | coding | 107.6% | — |
| 104692 | 294 | coding | 63.4% | 36.6% |
| 104693 | 295 | coding | 74.1% | 25.9% |
| 104694 | 296 | coding | 108.3% | — |
| 104695 | 297 | coding | 48.2% | 51.8% |
| 104696 | 298 | coding | 120.3% | — |
| 104697 | 299 | coding | 45.0% | 55.0% |
| 104698 | 300 | coding | 77.1% | 22.9% |
| 104699 | 301 | coding | 143.7% | — |
| 104700 | 302 | coding | 96.1% | 3.9% |
| 104701 | 303 | coding | 106.8% | — |
| 104702 | 304 | coding | 157.4% | — |
| 104703 | 305 | coding | 84.3% | 15.7% |
| 104704 | 306 | coding | 182.8% | — |
| 104705 | 307 | coding | 125.1% | — |
| 104706 | 308 | coding | 81.8% | 18.2% |
| 104707 | 309 | coding | 104.8% | — |
| 104708 | 310 | coding | 163.0% | — |
| 104709 | 311 | coding | 95.0% | 5.0% |
| 104710 | 312 | coding | 182.1% | — |
| 104711 | 313 | coding | 82.1% | 17.9% |
| 104712 | 314 | coding | 118.1% | — |
| 104713 | 315 | coding | 31.1% | 68.9% |
| 104714 | 316 | coding | 90.5% | 9.5% |
| 104715 | 317 | coding | 96.7% | 3.3% |
| 104716 | 318 | coding | 180.7% | — |
| 104717 | 93 | coding | 71.6% | 28.4% |
| 104718 | 94 | coding | 187.0% | — |
| 104719 | 319 | coding | 88.8% | 11.2% |
| 104720 | 320 | coding | 166.5% | — |
| 104721 | 321 | coding | 65.0% | 35.0% |
| 104722 | 322 | coding | 59.6% | 40.4% |
| 104723 | 26 | coding | 90.1% | 9.9% |
| 104724 | 323 | coding | 88.7% | 11.3% |
| 104725 | 90 | coding | 94.7% | 5.3% |
| 104726 | 91 | coding | 84.1% | 15.9% |
| 104727 | 324 | coding | 125.3% | — |
| 104728 | 325 | coding | 221.7% | — |
| 104729 | 326 | coding | 102.4% | — |
| 104730 | 327 | coding | 151.6% | — |
| 104731 | 328 | coding | 102.2% | — |
| 104732 | 329 | coding | 53.2% | 46.8% |
| 104733 | 330 | stop | 57.0% | 43.0% |
| 104734 | 88 | coding | 119.2% | — |
| 104735 | 331 | 3'-UTR | 71.2% | 28.8% |
| 104736 | 332 | stop | 79.0% | 21.0% |
| 104737 | 333 | 3'-UTR | 87.4% | 12.6% |
| 104738 | 334 | stop | 36.8% | 63.2% |
| 104739 | 335 | 3'-UTR | 106.0% | — |
| 104740 | 336 | 3'-UTR | 130.9% | — |
| 104741 | 337 | 3'-UTR | 79.2% | 20.8% |
| 104742 | 338 | 3'-UTR | 159.0% | — |
| 104743 | 339 | 3'-UTR | 96.1% | 3.9% |
| 104744 | 340 | 3'-UTR | 129.9% | — |
| 104745 | 341 | 3'-UTR | 80.2% | 19.8% |
| 104746 | 342 | 3'-UTR | 168.8% | — |
| 104747 | 343 | 3'-UTR | 89.2% | 10.8% |
| 104748 | 344 | 3'-UTR | 103.4% | — |
| 104749 | 345 | 3'-UTR | 89.0% | 11.0% |
| 104750 | 346 | 3'-UTR | 160.0% | — |
| 104751 | 347 | 3'-UTR | 60.1% | 39.9% |
| 104752 | 348 | 3'-UTR | 72.4% | 27.6% |
| 104753 | 349 | 3'-UTR | 70.0% | 30.0% |
| 104754 | 350 | 3'-UTR | 115.6% | — |
| 104755 | 351 | 3'-UTR | 71.7% | 28.3% |
| 104756 | 352 | 3'-UTR | 91.5% | 8.5% |
| 104757 | 353 | 3'-UTR | 85.6% | 14.4% |
| 104758 | 354 | 3'-UTR | 97.6% | 2.4% |
| 104759 | 355 | 3'-UTR | 68.6% | 31.4% |
| 104760 | 356 | 3'-UTR | 182.4% | — |
| 104761 | 357 | 3'-UTR | 110.9% | — |
| 104762 | 358 | 3'-UTR | 161.4% | — |
| 104763 | 359 | 3'-UTR | 102.0% | — |
| 104764 | 360 | 3'-UTR | 113.5% | — |
| 104765 | 361 | 3'-UTR | 154.8% | — |
| 104766 | 362 | 3'-UTR | 126.4% | — |
| 104767 | 363 | 3'-UTR | 116.1% | — |
| 104768 | 364 | 3'-UTR | 177.7% | — |
| 104769 | 365 | 3'-UTR | 89.8% | 10.2% |
| 104770 | 366 | 3'-UTR | 94.3% | 5.7% |
| 104771 | 367 | 3'-UTR | 191.2% | — |
| 104772 | 368 | 3'-UTR | 80.3% | 19.7% |
| 104773 | 369 | 3'-UTR | 133.9% | — |
| 104774 | 34 | 3'-UTR | 94.8% | 5.2% |
| 104775 | 370 | 3'-UTR | 80.6% | 19.4% |
| 104776 | 371 | 3'-UTR | 90.1% | 9.9% |
| 104777 | 372 | 3'-UTR | 84.7% | 15.3% |
| 104778 | 373 | 3'-UTR | 121.3% | — |
| 104779 | 374 | 3'-UTR | 97.8% | 2.2% |
| 104780 | 375 | 3'-UTR | 67.6% | 32.4% |
| 104781 | 376 | 3'-UTR | 141.5% | — |
| 104782 | 377 | 3'-UTR | 96.5% | 3.5% |
| 104783 | 378 | 3'-UTR | 153.2% | — |
| 104784 | 379 | 3'-UTR | 85.4% | 14.6% |
| 104785 | 380 | 3'-UTR | 163.9% | — |
| 104786 | 381 | 3'-UTR | 82.9% | 17.1% |
| 104787 | 382 | 3'-UTR | 89.7% | 10.3% |
| 104788 | 383 | 3'-UTR | 103.9% | — |
| 104789 | 384 | 3'-UTR | 75.8% | 24.2% |
| 104790 | 385 | 3'-UTR | 106.3% | — |
| 104791 | 386 | 3'-UTR | 165.3% | — |
| 104792 | 387 | 3'-UTR | 71.8% | 28.2% |
| 104793 | 388 | 3'-UTR | 101.9% | — |
| 104794 | 389 | 3'-UTR | 70.7% | 29.3% |
| 104795 | 390 | 3'-UTR | 68.8% | 31.2% |
| 104796 | 391 | 3'-UTR | 93.4% | 6.6% |
| 104797 | 37 | 3'-UTR | 131.7% | — |
| 104798 | 392 | 3'-UTR | 89.4% | 10.6% |
| 104799 | 393 | 3'-UTR | 89.6% | 10.4% |
| 104800 | 394 | 3'-UTR | 89.0% | 11.0% |
| 104801 | 395 | 3'-UTR | 196.8% | — |

TABLE 32-continued

Inhibition of Human TNF-α mRNA Expression by Chimeric
(deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 104802 | 396 | 3'-UTR | 189.3% | — |
| 104803 | 397 | 3'-UTR | 119.7% | — |
| 104804 | 398 | 3'-UTR | 102.4% | — |
| 104805 | 399 | 3'-UTR | 90.6% | 9.4% |
| 104806 | 400 | 3'-UTR | 89.1% | 10.9% |
| 104807 | 401 | 3'-UTR | 152.6% | — |
| 104808 | 402 | 3'-UTR | 96.8% | 3.2% |
| 104809 | 403 | 3'-UTR | 178.8% | — |
| 104810 | 404 | 3'-UTR | 94.9% | 5.1% |
| 104811 | 405 | 3'-UTR | 234.4% | — |
| 104812 | 406 | 3'-UTR | 114.3% | — |
| 104813 | 407 | 3'-UTR | 153.7% | — |
| 104814 | 408 | 3'-UTR | 86.3% | 13.7% |
| 104815 | 409 | 3'-UTR | 153.9% | — |
| 104816 | 410 | 3'-UTR | 79.9% | 20.1% |
| 104817 | 411 | 3'-UTR | 196.5% | — |
| 104818 | 412 | 3'-UTR | 94.3% | 5.7% |
| 104819 | 413 | 3'-UTR | 143.3% | — |
| 104820 | 414 | 3'-UTR | 123.8% | — |
| 104821 | 415 | 3'-UTR | 129.2% | — |
| 104822 | 416 | 5'-UTR | 76.6% | 23.4% |
| 104823 | 417 | 5'-UTR | 63.9% | 36.1% |
| 104824 | 418 | 5'-UTR | 22.0% | 78.0% |
| 104825 | 419 | 5'-UTR | 109.4% | — |
| 104826 | 420 | 5'-UTR | 45.2% | 54.8% |
| 104827 | 421 | 5'-UTR | 68.9% | 31.1% |
| 104828 | 422 | 5'-UTR | 70.9% | 29.1% |
| 104829 | 423 | AUG | 46.6% | 53.4% |
| 104830 | 424 | coding | 55.0% | 45.0% |
| 104831 | 425 | coding | 49.5% | 50.5% |
| 104832 | 426 | coding | 106.0% | — |
| 104833 | 427 | coding | 23.7% | 76.3% |
| 104834 | 428 | coding | 91.8% | 8.2% |
| 104835 | 429 | coding | 72.3% | 27.7% |
| 104836 | 430 | coding | 63.4% | 36.6% |
| 104837 | 431 | coding | 31.0% | 69.0% |
| 104838 | 432 | coding | 18.0% | 82.0% |
| 104839 | 433 | coding | 67.9% | 32.1% |
| 104840 | 434 | coding | 93.8% | 6.2% |
| 104841 | 435 | coding | 43.0% | 57.0% |
| 104842 | 436 | coding | 73.2% | 26.8% |
| 104843 | 437 | coding | 48.1% | 51.9% |
| 104844 | 438 | coding | 39.2% | 60.8% |
| 104845 | 439 | coding | 37.6% | 62.4% |
| 104846 | 440 | coding | 81.7% | 18.3% |
| 104847 | 441 | coding | 50.8% | 49.2% |
| 104848 | 442 | coding | 56.7% | 43.3% |
| 104849 | 443 | coding | 51.8% | 48.2% |
| 104850 | 444 | coding | 91.8% | 8.2% |
| 104851 | 445 | coding | 93.9% | 6.1% |
| 104852 | 446 | coding | 100.9% | — |
| 104853 | 447 | coding | 67.7% | 32.3% |
| 104854 | 23 | coding | 11.0% | 89.0% |
| 104855 | 448 | coding | 62.5% | 37.5% |
| 104856 | 449 | coding | 67.8% | 32.2% |
| 104857 | 92 | coding | 28.1% | 71.9% |
| 104858 | 450 | coding | 76.2% | 23.8% |
| 104859 | 451 | coding | 52.3% | 47.7% |
| 104860 | 452 | coding | 93.6% | 6.4% |
| 104861 | 89 | coding | 79.3% | 20.7% |
| 104862 | 453 | coding | 63.1% | 36.9% |
| 104863 | 454 | stop | 64.5% | 35.5% |
| 104864 | 455 | stop | 43.2% | 56.8% |
| 104865 | 456 | 3'-UTR | 83.1% | 16.9% |
| 104866 | 457 | 3'-UTR | 49.4% | 50.6% |
| 104867 | 458 | 3'-UTR | 49.5% | 50.5% |
| 104868 | 459 | 3'-UTR | 89.6% | 10.4% |
| 104869 | 460 | 3'-UTR | 21.4% | 78.6% |
| 104870 | 461 | 3'-UTR | 118.0% | — |
| 104871 | 462 | 3'-UTR | 55.8% | 44.2% |
| 104872 | 463 | 3'-UTR | 49.0% | 51.0% |
| 104873 | 464 | 3'-UTR | 92.6% | 7.4% |
| 104874 | 465 | 3'-UTR | 33.4% | 66.6% |
| 104875 | 466 | 3'-UTR | 36.2% | 63.8% |
| 104876 | 467 | 3'-UTR | 73.4% | 26.6% |
| 104877 | 468 | 3'-UTR | 40.9% | 59.1% |
| 104878 | 469 | 3'-UTR | 78.7% | 21.3% |
| 104879 | 470 | 3'-UTR | 75.4% | 24.6% |
| 104880 | 471 | 3'-UTR | 50.2% | 49.8% |
| 104881 | 472 | 3'-UTR | 47.0% | 53.0% |
| 104882 | 473 | 3'-UTR | 82.7% | 17.3% |
| 104883 | 474 | 3'-UTR | 46.4% | 53.6% |
| 104884 | 475 | 3'-UTR | 46.1% | 53.9% |
| 104885 | 476 | 3'-UTR | 156.9% | — |
| 104886 | 477 | 3'-UTR | 102.4% | — |
| 104887 | 478 | 3'-UTR | 59.1% | 40.9% |
| 104888 | 479 | 3'-UTR | 64.7% | 35.3% |
| 104889 | 480 | 3'-UTR | 83.7% | 16.3% |
| 104890 | 481 | 3'-UTR | 52.9% | 47.1% |
| 104891 | 482 | 3'-UTR | 87.9% | 12.1% |
| 104892 | 483 | 3'-UTR | 39.8% | 60.2% |
| 104893 | 484 | 3'-UTR | 71.1% | 28.9% |
| 104894 | 485 | 3'-UTR | 34.0% | 66.0% |
| 104895 | 486 | 3'-UTR | 129.8% | — |
| 104896 | 487 | 3'-UTR | 57.6% | 42.4% |
| 104897 | 488 | 3'-UTR | 49.6% | 50.4% |
| 104898 | 489 | 3'-UTR | 71.7% | 28.3% |
| 104899 | 490 | 3'-UTR | 101.5% | — |
| 104900 | 491 | 3'-UTR | 142.1% | — |
| 104901 | 492 | 3'-UTR | 55.9% | 44.1% |
| 104902 | 493 | 3'-UTR | 85.3% | 14.7% |
| 104903 | 494 | 3'-UTR | 46.0% | 54.0% |
| 104904 | 495 | 3'-UTR | 59.9% | 40.1% |
| 104905 | 496 | 3'-UTR | 47.2% | 52.8% |
| 104906 | 497 | 3'-UTR | 56.3% | 43.7% |

Oligonucleotides 104662 (SEQ ID NO: 264), 104669 (SEQ ID NO: 271), 104670 (SEQ ID NO: 272), 104688 (SEQ ID NO: 290), 104695 (SEQ ID NO: 297), 104697 (SEQ ID NO: 299), 104713 (SEQ ID NO: 315), 104738 (SEQ ID NO:334), 104824 (SEQ ID NO: 418), 104826 (SEQ ID NO: 420), 104829 (SEQ ID NO: 423), 104831 (SEQ ID NO: 425), 104833 (SEQ ID NO: 427), 104837 (SEQ ID NO: 431), 104838 (SEQ ID NO: 432), 104841 (SEQ ID NO: 435), 104843 (SEQ ID NO: 437), 104844 (SEQ ID NO: 438), 104845 (SEQ ID NO: 439), 104847 (SEQ ID NO: 441), 104854 (SEQ ID NO: 23), 104857 (SEQ ID NO: 92), 104864 (SEQ ID NO: 455), 104866 (SEQ ID NO: 457), 104867 (SEQ ID NO: 458), 104869 (SEQ ID NO: 460), 104872 (SEQ ID NO: 463), 104874 (SEQ ID NO: 465), 104875 (SEQ ID NO: 466), 104877 (SEQ ID NO: 468), 104880 (SEQ ID NO: 471), 104881 (SEQ ID NO: 472), 104883 (SEQ ID NO: 474), 104884 (SEQ ID NO: 475), 104892 (SEQ ID NO: 483), 104894 (SEQ ID NO: 485), 104897 (SEQ ID NO: 488), 104903 (SEQ ID NO: 494) and 104905 (SEQ ID NO: 496) gave approximately 50% or greater reduction in TNF-α mRNA expression in this assay. Oligonucleotides 104713 (SEQ ID NO: 315), 104824 (SEQ ID NO: 418), 104833 (SEQ ID NO: 427), 104837 (SEQ ID NO: 431), 104838 (SEQ ID NO: 432), 104854 (SEQ ID NO: 23), 104857 (SEQ ID NO: 92), and 104869 (SEQ ID NO: 460) gave approximately 70% or greater reduction in TNF-α mRNA expression in this assay.

Example 23
Dose Response of Chimeric (Deoxy Gapped) Antisense Phosphorothioate Oligodeoxynucleotide Effects on TNF-α mRNA and Protein Levels Several oligonucleotides from the initial screen were chosen for dose response assays. NeoHk cells were grown, treated and processed as described in Example 3. LIPOFECTIN® was added at a ratio of 3 µg/ml per 100 nM of oligonucleotide. The control included LIPOFECTIN® at a concentration of 9 µg/ml.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of $8 \times 10^5$ cells were employed for each treatment by combining 50 µl of cell suspension in OPTIMEM™, 1% FBS with oligonucleotide at the indicated concentrations to reach a final volume of 100 µl with OPTIMEM™, 1% FBS. Cells were then transferred to a 1 mm electroporation cuvette and electroporated using an Electrocell Manipulator 600 instrument (Biotechnologies and Experimental Research, Inc.) employing 90 V, 1000 µF, at 13Ω. Electroporated cells were then transferred to 24 well plates. 400 µl of RPMI 1640, 10% FCS was added to the cells and the cells were allowed to recover for 6 hrs. Cells were then induced with LPS at a final concentration of 100 ng/ml for 2 hours. RNA was isolated and processed as described in Example 3.

Results with NeoHK cells are shown in Table 33 for mRNA, and Table 34 for protein. Results with THP-1 cells are shown in Table 35.

Most of the oligonucleotides tested showed dose response effects with a maximum inhibition of mRNA greater than 70% and a maximum inhibition of protein greater than 85%.

TABLE 33

Dose Response of NeoHK Cells to TNF-α Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| induced | — | — | — | 100% | — |
| 16798 | 128 | coding | 30 nM | 87% | 13% |
| " | " | " | 100 nM | 129% | — |
| " | " | " | 300 nM | 156% | — |
| 21823 | 69 | intron 1 | 30 nM | 82% | 18% |
| " | " | " | 100 nM | 90% | 10% |
| " | " | " | 300 nM | 59% | 41% |
| 28088 | 68 | intron 1 | 30 nM | 68% | 32% |
| " | " | " | 100 nM | 43% | 57% |
| " | " | " | 300 nM | 42% | 58% |
| 28089 | 69 | intron 1 | 30 nM | 59% | 41% |
| " | " | " | 100 nM | 44% | 56% |
| " | " | " | 300 nM | 38% | 62% |
| 104697 | 299 | coding | 30 nM | 60% | 40% |
| " | " | " | 100 nM | 45% | 55% |
| " | " | " | 300 nM | 27% | 73% |
| 104777 | 372 | 3"-UTR | 30 nM | 66% | 34% |
| " | " | " | 100 nM | 55% | 45% |
| " | " | " | 300 nM | 43% | 57% |

TABLE 34

Dose Response of NeoHK Cells to TNF-α Chimeric (deoxy gapped) Antisense Oligonucleotides

| ISIS # | SEQ ID NO: | ASO Gene Target | Dose | % Protein Expression | % Protein Inhibition |
|---|---|---|---|---|---|
| induced | — | — | — | 100.0% | — |
| 16798 | 128 | coding | 30 nM | 115.0% | — |
| " | " | " | 100 nM | 136.0% | — |
| " | " | " | 300 nM | 183.0% | — |
| 28089 | 69 | intron 1 | 30 nM | 87.3% | 12.7% |
| " | " | " | 100 nM | 47.4% | 52.6% |
| " | " | " | 300 nM | 22.8% | 77.2% |

TABLE 34-continued

Dose Response of NeoHK Cells to TNF-α Chimeric (deoxy gapped) Antisense Oligonucleotides

| ISIS # | SEQ ID NO: | ASO Gene Target | Dose | % Protein Expression | % Protein Inhibition |
|---|---|---|---|---|---|
| 104681 | 283 | coding | 30 nM | 91.3% | 8.7% |
| " | " | " | 100 nM | 62.0% | 38.0% |
| " | " | " | 300 nM | 28.5% | 71.5% |
| 104697 | 299 | coding | 30 nM | 87.1% | 12.9% |
| " | " | " | 100 nM | 59.6% | 40.4% |
| " | " | " | 300 nM | 29.1% | 70.9% |
| 104838 | 432 | coding | 30 nM | 91.9% | 8.1% |
| " | " | " | 100 nM | 56.9% | 43.1% |
| " | " | " | 300 nM | 14.8% | 85.2% |
| 104854 | 23 | coding | 30 nM | 64.4% | 35.6% |
| " | " | " | 100 nM | 42.3% | 57.7% |
| " | " | " | 300 nM | 96.1% | 3.9% |
| 104869 | 460 | 3'-UTR | 30 nM | 88.9% | 11.1% |
| " | " | " | 100 nM | 56.8% | 43.2% |
| " | " | " | 300 nM | 42.3% | 57.7% |

TABLE 35

Dose Response of LPS-Induced THP-1 Cells to Chimeric (deoxy gapped) TNF-α Antisense Phosphorothioate Oligodeoxynucleotides (ASOs)

| ISIS # | SEQ ID NO: | ASO Gene Target | Dose | % mRNA Expression | % mRNA Inhibition |
|---|---|---|---|---|---|
| induced | — | — | — | 100% | — |
| 16798 | 128 | coding | 1 µM | 102% | — |
| " | " | " | 3 µM | 87% | 13% |
| " | " | " | 10 µM | 113% | — |
| " | " | " | 30 µM | 134% | — |
| 28089 | 69 | intron 1 | 1 µM | 39% | 61% |
| " | " | " | 3 µM | 79% | 21% |
| " | " | " | 10 µM | 91% | 9% |
| " | " | " | 30 µM | 63% | 37% |
| 104697 | 299 | coding | 1 µM | 99% | 1% |
| " | " | " | 3 µM | 96% | 4% |
| " | " | " | 10 µM | 92% | 8% |
| " | " | " | 30 µM | 52% | 48% |
| 104838 | 432 | coding | 1 µM | 31% | 69% |
| " | " | " | 3 µM | 20% | 80% |
| " | " | " | 10 µM | 15% | 85% |
| " | " | " | 30 µM | 7% | 93% |
| 104854 | 23 | coding | 1 µM | 110% | — |
| " | " | " | 3 µM | 90% | 10% |
| " | " | " | 10 µM | 95% | 5% |
| " | " | " | 30 µM | 61% | 39% |

Example 24

Further Optimization of Human TNF-α Antisense Oligonucleotide Chemistry

Additional analogs of TNF-α oligonucleotides were designed and synthesized to find an optimum gap size. The sequences and chemistries are shown in Table 36.

Dose response experiments are performed as described in Example 3.

TABLE 29

Nucleotide Sequences of TNF-αChimeric Backbone (deoxy gapped) Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 110554 | GCTGATTAGAGAGAGGTCCC | 432 | 104838 | analog |
| 110555 | GCTGATTAGAGAGAGGTCCC | " | " | " |
| 110556 | GCTGATTAGAGAGAGGTCCC | " | " | " |
| 110557 | GCTGATTAGAGAGAGGTCCC | " | " | " |
| 110583 | GCTGATTAGAGAGAGGTCCC | " | " | " |
| 110558 | CTGATTAGAGAGAGGTCCC | 498 | 1596–1614 | coding |
| 110559 | CTGATTAGAGAGAGGTCCC | " | " | " |
| 110560 | CTGATTAGAGAGAGGTCCC | " | " | " |
| 110561 | CTGATTAGAGAGAGGTCCC | " | " | " |
| 110562 | CTGATTAGAGAGAGGTCCC | " | " | " |
| 110563 | CTGATTAGAGAGAGGTCCC | " | " | " |
| 110564 | CTGATTAGAGAGAGGTCCC | " | " | " |
| 110565 | CTGATTAGAGAGAGGTCCC | " | " | " |
| 110566 | CTGATTAGAGAGAGGTCCC | " | " | " |
| 110567 | CTGATTAGAGAGAGGTCCC | " | " | " |
| 110584 | CTGATTAGAGAGAGGTCCC | " | " | " |
| 108371 | CTGATTAGAGAGAGGTCC | 499 | 1597–1614 | coding |
| 110568 | CTGATTAGAGAGAGGTCC | " | " | " |
| 110569 | CTGATTAGAGAGAGGTCC | " | " | " |
| 110570 | CTGATTAGAGAGAGGTCC | " | " | " |
| 110585 | CTGATTAGAGAGAGGTCC | " | " | " |
| 110571 | CTGGTTATCTCTCAGCTCCA | 299 | 104697 | analog |
| 110572 | CTGGTTATCTCTCAGCTCCA | " | " | " |
| 110573 | CTGGTTATCTCTAGCTCCA | " | " | " |
| 110586 | CTGGTTATCTCTCAGCTCCA | " | " | " |
| 110574 | GATCACTCCAAAGTGCAGCA | 283 | 104681 | analog |
| 110575 | GATCACTCCAAAGTGCAGCA | " | " | " |
| 110576 | GATCACTCCAAAGTGCAGCA | " | " | " |
| 110587 | GATCACTCCAAAGTGCAGCA | " | " | " |
| 110577 | AGCTTGGGTTCCGACCCTAA | 460 | 104689 | analog |
| 110578 | AGCTTGGGTTCCGACCCTAA | " | " | " |
| 110579 | AGCTTGGGGTTCCGACCCTAA | " | " | " |
| 110588 | AGCTTGGGTTCCGACCCTAA | " | " | " |
| 110580 | AGGTTGACCTTGGTCTGGTA | 315 | 104713 | analog |
| 110581 | AGGTTGACCTTGGTCTGGTA | " | " | " |
| 110582 | AGGTTGACCTTGGTTCTGGTA | " | " | " |
| 110589 | AGGTTGACCTTGGTCTGGTA | " | " | " |
| 110637 | GTGTGCCAGACACCCTATCT | 69 | 21823 | analog |
| 110651 | GTGTGCCAGACACCCTATCT | " | " | " |
| 110665 | GTGTGCCAGACACCCTATCT | " | " | " |
| 110679 | GTGTGCCAGACACCCTATCT | " | " | " |
| 110693 | GTGTGCCAGACACCCTATCT | " | " | " |
| 110707 | GTGTGCCAGACACCCTATCT | " | " | " |
| 110590 | TGAGTGTCTTCTGTGTGCCA | 500 | 1411–1430 | intron 1 |
| 110597 | TGAGTGTCTTCTGTGTGCCA | " | " | intron 1 |
| 110604 | TGAGTGTCTTCTGTGTGCCA | " | " | intron 1 |
| 110611 | TGAGTGTCTTCTGTGTGCCA | " | " | intron 1 |
| 110618 | TGAGTGTCTTCTGTGTGCCA | " | " | intron 1 |
| 110625 | TGAGTGTCTTCTGTGTGCCA | " | " | intron 1 |
| 110591 | GAGTGTCTTCTGTGTGCCAG | 501 | 1410–1429 | intron 1 |
| 110598 | GAGTGTCTTCTGTGTGCCAG | " | " | intron 1 |
| 110605 | GAGTGTCTTCTGTGTGCCAG | " | " | intron 1 |
| 110612 | GAGTGTCTTCTGTGTGCCAG | " | " | intron 1 |
| 110619 | GAGTGTCTTCTGTGTGCCAG | " | " | intron 1 |
| 110626 | GAGTGTCTTCTGTGTGCCAG | " | " | intron 1 |
| 110592 | AGTGTCTTCTGTGTGCCAGA | 144 | 100181 | analog |
| 110599 | AGTGTCTTCTGTGTGCCAGA | " | " | " |
| 110606 | AGTGTCTTCTGTGTGCCAGA | " | " | " |
| 110613 | AGTGTCTTCTGTGTGCCAGA | " | " | " |
| 110620 | AGTGTCTTCTGTGTGCCAGA | " | " | " |
| 110627 | AGTGTCTTCTGTGTGCCAGA | " | " | " |
| 110593 | GTGTCTTCTGTGTGCCAGAC | 145 | 100182 | analog |
| 110600 | GTGTCTTCTGTGTGCCAGAC | " | " | " |
| 110607 | GTGTCTTCTGTGTGCCAGAC | " | " | " |
| 110614 | GTGTCTTCTGTGTGCCAGAC | " | " | " |
| 110621 | GTGTCTTCTGTGTGCCAGAC | " | " | " |

TABLE 29-continued

Nucleotide Sequences of TNF-α Chimeric Backbone (deoxy gapped) Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 110628 | GTGTCTTCTGTGTGCCAGAC | " | " | |
| 110594 | TGTCTTCTGTGTGCCAGACA | 146 | 100183 | analog |
| 110601 | TGTCTTCTGTGTGCCAGACA | " | " | |
| 110608 | TGTCTTCTGTGTGCCAGACA | " | " | |
| 110615 | TGTCTTCTGTGTGCCAGACA | " | " | |
| 110622 | TGTCTTCTGTGTGCCAGACA | " | " | |
| 110629 | TGTCTTCTGTGTGCCAGACA | " | " | |
| 110595 | GTCTTCTGTGTGCCAGACAC | 147 | 100184 | analog |
| 110602 | GTCTTCTGTGTGCCAGACAC | " | " | |
| 110609 | GTCTTCTGTGTGCCAGACAC | " | " | |
| 110616 | GTCTTCTGTGTGCCAGACAC | " | " | |
| 110623 | GTCTTCTGTGTGCCAGACAC | " | " | |
| 110630 | GTCTTCTGTGTGCCAGACAC | " | " | |
| 110596 | TCTTCTGTGTGCCAGACACC | 148 | 100185 | analog |
| 110603 | TCTTCTGTGTGCCAGACACC | " | " | |
| 110610 | TCTTCTGTGTGCCAGACACC | " | " | |
| 110617 | TCTTCTGTGTGCCAGACACC | " | " | |
| 110624 | TCTTCTGTGTGCCAGACACC | " | " | |
| 110631 | TCTTCTGTGTGCCAGACACC | " | " | |
| 110632 | CTTCTGTGTGCCAGACACCC | 149 | 100186 | analog |
| 110646 | CTTCTGTGTGCCAGACACCC | " | " | |
| 110660 | CTTCTGTGTGCCAGACACCC | " | " | |
| 110674 | CTTCTGTGTGCCAGACACCC | " | " | |
| 110688 | CTTCTGTGTGCCAGACACCC | " | " | |
| 110702 | CTTCTGTGTGCCAGACACCC | " | " | |
| 110633 | TTCTGTGTGCCAGACACCCT | 150 | 100187 | analog |
| 110647 | TTCTGTGTGCCAGACACCCT | " | " | |
| 110661 | TTCTGTGTGCCAGACACCCT | " | " | |
| 110675 | TTCTGTGTGCCAGACACCCT | " | " | |
| 110689 | TTCTGTGTGCCAGACACCCT | " | " | |
| 110703 | TTCTGTGTGCCAGACACCCT | " | " | |
| 110634 | TCTGTGTGCCAGACACCCTA | 151 | 100188 | analog |
| 110648 | TCTGTGTGCCAGACACCCTA | " | " | |
| 110662 | TCTGTGTGCCAGACACCCTA | " | " | |
| 110676 | TCTGTGTGCCAGACACCCTA | " | " | |
| 110690 | TCTGTGTGCCAGACACCCTA | " | " | |
| 110704 | TCTGTGTGCCAGACACCCTA | " | " | |
| 110635 | CTGTGTGCCAGACACCCTAT | 152 | 100189 | analog |
| 110649 | CTGTGTGCCAGACACCCTAT | " | " | |
| 110663 | CTGTGTGCCAGACACCCTAT | " | " | |
| 110677 | CTGTGTGCCAGACACCCTAT | " | " | |
| 110691 | CTGTGTGCCAGACACCCTAT | " | " | |
| 110705 | CTGTGTGCCAGACACCCTAT | " | " | |
| 110636 | TGTGTGCCAGACACCCTATC | 153 | 100190 | analog |
| 110650 | TGTGTGCCAGACACCCTATC | " | " | |
| 110664 | TGTGTGCCAGACACCCTATC | " | " | |
| 110678 | TGTGTGCCAGACACCCTATC | " | " | |
| 110692 | TGTGTGCCAGACACCCTATC | " | " | |
| 110706 | TGTGTGCCAGACACCCTATC | " | " | |
| 110638 | TGTGCCAGACACCCTATCTT | 154 | 100191 | analog |
| 110652 | TGTGCCAGACACCCTATCTT | " | " | |
| 110666 | TGTGCCAGACACCCTATCTT | " | " | |
| 110680 | TGTGCCAGACACCCTATCTT | " | " | |
| 110694 | TGTGCCAGACACCCTATCTT | " | " | |
| 110708 | TGTGCCAGACACCCTATCTT | " | " | |
| 110639 | GTGCCAGACACCCTATCTTC | 155 | 100192 | analog |
| 110653 | GTGCCAGACACCCTATCTTC | " | " | |
| 110667 | GTGCCAGACACCCTATCTTC | " | " | |
| 110681 | GTGCCAGACACCCTATCTTC | " | " | |
| 110695 | GTGCCAGACACCCTATCTTC | " | " | |
| 110709 | GTGCCAGACACCCTATCTTC | " | " | |
| 110640 | TGCCAGACACCCTATCTTCT | 156 | 100193 | analog |
| 110654 | TGCCAGACACCCTATCTTCT | " | " | |
| 110668 | TGCCAGACACCCTATCTTCT | " | " | |
| 110682 | TGCCAGACACCCTATCTTCT | " | " | |
| 110696 | TGCCAGACACCCTATCTTCT | " | " | |
| 110710 | TGCCAGACACCCTATCTTCT | " | " | |
| 110641 | GCCAGACACCCTATCTTCTT | 157 | 100194 | analog |
| 110655 | GCCAGACACCCTATCTTCTT | " | " | |
| 110669 | GCCAGACACCCTATCTTCTT | " | " | |
| 110683 | GCCAGACACCCTATCTTCTT | " | " | |
| 110697 | GCCAGACACCCTATCTTCTT | " | " | |

TABLE 29-continued

Nucleotide Sequences of TNF-αChimeric Backbone (deoxy gapped) Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 110711 | GCCAGACACCTATCTTCTT | " | " | |
| 110642 | CCAGACACCCTATCTTCTTC | 158 | 100195 | analog |
| 110656 | CCAGACACCCTATCTTCTTC | " | " | |
| 110670 | CCAGACACCCTATCTTCTTC | " | " | |
| 110684 | CCAGACACCCTATCTTCTTC | " | " | |
| 110698 | CCAGACACCCTATCTTCTTC | " | " | |
| 110712 | CCAGACACCCTATCTTCTTC | " | " | |
| 110643 | CAGACACCCTATCTTCTTCT | 159 | 100196 | analog |
| 110657 | CAGACACCCTATCTTCTTCT | " | " | |
| 110671 | CAGACACCCTATCTTCTTCT | " | " | |
| 110685 | CAGACACCCTATCTTCTTCT | " | " | |
| 110699 | CAGACACCCTATCTTCTTCT | " | " | |
| 110713 | CAGACACCCTATCTTCTTCT | " | " | |
| 110644 | AGACACCCTATCTTCTTCTC | 160 | 100197 | analog |
| 110658 | AGACACCCTATCTTCTTCTC | " | " | |
| 110672 | AGACACCCTATCTTCTTCTC | " | " | |
| 110686 | AGACACCCTATCTTCTTCTC | " | " | |
| 110700 | AGACACCCTATCTTCTTCTC | " | " | |
| 110714 | AGACACCCTATCTTCTTCTC | " | " | |
| 110645 | GACACCCTATCTTCTTCTCT | 161 | 100198 | analog |
| 110659 | GACACCCTATCTTCTTCTCT | " | " | |
| 110673 | GACACCCTATCTTCTTCTCT | " | " | |
| 110687 | GACACCCTATCTTCTTCTCT | " | " | |
| 110701 | GACACCCTATCTTCTTCTCT | " | " | |
| 110715 | GACACCCTATCTTCTTCTCT | " | " | |

[1]Emboldened residues are 2'-methoxyethoxy residues (others are 2'-deoxy-). All 2'-methoxyethoxy cytidines and 2'-deoxycytidines are 5-methyl-cytidines; all linkages are phosphorothioate linkages.
[2]Co-ordinates from Genbank Accession No. X02910, locus name "HSTNFA", SEQ ID NO. 1.

Example 25

Effect of TNF-α Antisense Oligonucleotides in TNF-α Transgenic Mouse Models

The effect of TNF-α antisense oligonucleotides is studied in transgenic mouse models of human diseases. Such experiments can be performed through contract laboratories (e.g. The Laboratory of Molecular Genetics at The Hellenic Pasteur Institute, Athens, Greece) where such transgenic mouse models are available. Such models are available for testing human oligonucleotides in arthritis (Keffer, J., et al., *EMBO J.*, 1991, 10, 4025–4031) and multiple sclerosis (Akassoglou, K., et al., *J. Immunol.*, 1997, 158, 438–445) models. A model for inflammatory bowel disease is available for testing mouse oligonucleotides (Kontoyiannis, D., et al., *Immunity*, 1999, 10, 387–398).

Briefly, litters of the appropriate transgenic mouse strain are collected and weighed individually. Twice weekly from birth, oligonucleotide in saline is administered intraperitoneally or intravenously. Injections continue for 7 weeks. Each week the animals are scored for manifestations of the appropriate disease. After the final treatment, the mice are sacrificed and histopathology is performed for indicators of disease as indicated in the references cited for each model.

What is claimed is:

1. An oligonucleotide up to 30 nucleotides in length complementary to a nucleic acid molecule encoding human tumor necrosis factor-α, wherein said oligonucleotide inhibits the expression of said human tumor necrosis factor-α and comprises at least an 8 nucleobase portion of SEQ ID NO: 24, SEQ ID NO: 27, SEQ ID NO: 28, SEQ ID NO: 29, SEQ ID NO: 30, SEQ ID NO: 34, SEQ ID NO: 39, SEQ ID NO: 88, SEQ ID NO: 90, SEQ ID NO: 91, SEQ ID NO: 92, SEQ ID NO: 93, SEQ ID NO: 97, SEQ ID NO: 98, SEQ ID NO: 149, SEQ ID NO: 157, SEQ ID NO: 264, SEQ ID NO: 271, SEQ ID NO: 272, SEQ ID NO: 290, SEQ ID NO: 297, SEQ ID NO: 299, SEQ ID NO: 315, SEQ ID NO: 334, SEQ ID NO: 418, SEQ ID NO: 423, SEQ ID NO: 425, SEQ ID NO: 427, SEQ ID NO: 431, SEQ ID NO: 432, SEQ ID NO: 435, SEQ ID NO: 437, SEQ ID NO: 438, SEQ ID NO: 439, SEQ ID NO: 441, SEQ ID NO: 455, SEQ ID NO: 457, SEQ ID NO: 458, SEQ ID NO: 460, SEQ ID NO: 463, SEQ ID NO: 465, SEQ ID NO: 466, SEQ ID NO: 468, SEQ ID NO: 472, SEQ ID NO: 474, SEQ ID NO: 475, SEQ ID NO: 483, SEQ ID NO: 485, SEQ ID NO: 494 or SEQ ID NO: 496.

2. The oligonucleotide of claim 1 which contains at least one phosphorothioate intersugar linkage.

3. The oligonucleotide of claim 1 which has at least one 2'-O-methoxyethyl modification.

4. The oligonucleotide of claim 1 which contains at least one 5-methyl cytidine.

5. The oligonucleotide of claim 3 in which every 2'-O-methoxyethyl modified cytidine residue is a 5-methyl cytidine.

6. The oligonucleotide of claim 4 in which every cytidine residue is a 5-methyl cytidine.

7. The oligonucleotide of claim 1 which contains at least one methylene(methylimino) intersugar linkage.

8. A composition comprising the oligonucleotide of claim 1 and a pharmaceutically acceptable carrier or diluent.

9. The composition of claim 8 wherein said pharmaceutically acceptable carrier or diluent comprises a lipid or liposome.

10. A method of inhibiting the expression of human tumor necrosis factor-α in cells or tissue comprising contacting said cells or tissue in vitro with the oligonucleotide of claim 1 whereby the expression of human tumor necrosis factor-α in cells or tissue is inhibited.

11. A method of reducing an inflammatory response of human cells comprising contacting said human cells in vitro with the oligonucleotide of claim 1 whereby the expression of human tumor necrosis factor-α in cells or tissue is inhibited.

12. A method of inhibiting the expression of human tumor necrosis factor-α in adipose tissue comprising contacting said adipose tissue with an antisense compound comprising an antisense oligonucleotide of claim 1 whereby the expression of human tumor necrosis factor-α in adipose tissue is inhibited.

13. A method of inhibiting the function of human tumor necrosis factor-α in adipose tissue comprising contacting said adipose tissue with an antisense compound comprising an antisense oligonucleotide of claim 1 whereby the expression of human tumor necrosis factor-α in cells or tissue is inhibited.

14. An oligonucleotide complementary to a nucleic acid molecule encoding human TNF-alpha wherein said oligonucleotide inhibits the expression of said TNF-alpha and consists of SEQ ID NO: 432.

* * * * *

SEQUENCE LISTING

<160> NUMBER OF SEQ ID NOS: 501

<210> SEQ ID NO: 1
<211> LENGTH: 3634
<212> TYPE: DNA
<213> ORGANISM: Homo sapiens
<220> FEATURE:
<221> NAME/KEY: CDS
<222> LOCATION: (796..981,1589..1634,1822..1869,2171..2592)
<220> FEATURE:
<221> NAME/KEY: exon
<222> LOCATION: (615)..(981)
<220> FEATURE:
<221> NAME/KEY: intron
<222> LOCATION: (982)..(1588)
<220> FEATURE:
<221> NAME/KEY: exon
<222> LOCATION: (1589)..(1634)
<220> FEATURE:

```
<221> NAME/KEY: intron
<222> LOCATION: (1635)..(1821)
<220> FEATURE:
<221> NAME/KEY: exon
<222> LOCATION: (1822)..(1869)
<220> FEATURE:
<221> NAME/KEY: intron
<222> LOCATION: (1870)..(2070)
<220> FEATURE:
<221> NAME/KEY: exon
<222> LOCATION: (2171)..(3381)
<300> PUBLICATION INFORMATION:
<301> AUTHORS: Nedwin, G.E.
      Naylor, S.L.
      Sakaguchi, A.Y.
      Smith, D.
      Jarrett-Nedwin, J.
      Pennica, D.
      Goeddel, D.V.
      Gray, P.W.
<302> TITLE: Human lymphotoxin and tumor necrosis factor genes:
<302> TITLE: structure, homology and chromosomal localization
<303> JOURNAL: Nucleic Acids Res.
<304> VOLUME: 13
<305> ISSUE: 17
<306> PAGES: 6361-6373
<307> DATE: 1985-09-11
<308> DATABASE ACCESSION NUMBER: X02910 Genbank
<309> DATABASE ENTRY DATE: 1997-02-17

<400> SEQUENCE: 1
```

| | |
|---|---|
| gaattccggg tgatttcact cccggctgtc caggcttgtc ctgctacccc acccagcctt | 60 |
| tcctgaggcc tcaagcctgc caccaagccc ccagctcctt ctccccgcag acccaaaca | 120 |
| caggcctcag gactcaacac agcttttccc tccaacccgt tttctctccc tcaacggact | 180 |
| cagctttctg aagcccctcc cagttctagt tctatctttt tcctgcatcc tgtctggaag | 240 |
| ttagaaggaa acagaccaca gacctggtcc ccaaaagaaa tggaggcaat aggttttgag | 300 |
| gggcatgggg acgggttca gcctccaggg tcctacacac aaatcagtca gtggcccaga | 360 |
| agacccccct cggaatcgga gcagggagga tggggagtgt gaggggtatc cttgatgctt | 420 |
| gtgtgtcccc aactttccaa atccccgccc cgcgatgga gaagaaaccg agacagaagg | 480 |
| tgcagggccc actaccgctt cctccagatg agctcatggg tttctccacc aaggaagttt | 540 |
| tccgctggtt gaatgattct ttccccgccc tcctctcgcc caggacat ataaaggcag | 600 |
| ttgttggcac acccagccag cagacgctcc ctcagcaagg acagcagagg accagctaag | 660 |
| agggagagaa gcaactacag accccccctg aaaacaaccc tcagacgcca catcccctga | 720 |
| caagctgcca ggcaggttct cttcctctca catactgacc cacggcttca cctctctcc | 780 |
| cctggaaagg acacc atg agc act gaa agc atg atc cgg gac gtg gag ctg | 831 |
|                 Met Ser Thr Glu Ser Met Ile Arg Asp Val Glu Leu | |
|                   1               5                  10 | |
| gcc gag gag gcg ctc ccc aag aag aca ggg ggg ccc cag ggc tcc agg | 879 |
| Ala Glu Glu Ala Leu Pro Lys Lys Thr Gly Gly Pro Gln Gly Ser Arg | |
|            15                  20                  25 | |
| cgg tgc ttg ttc ctc agc ctc ttc tcc ttc ctg atc gtg gca ggc gcc | 927 |
| Arg Cys Leu Phe Leu Ser Leu Phe Ser Phe Leu Ile Val Ala Gly Ala | |
|        30                  35                  40 | |
| acc acg ctc ttc tgc ctg ctg cac ttt gga gtg atc ggc ccc cag agg | 975 |
| Thr Thr Leu Phe Cys Leu Leu His Phe Gly Val Ile Gly Pro Gln Arg | |
|    45                  50                  55                  60 | |
| gaa gag gtgagtgcct ggccagcctt catccactct cccacccaag gggaaatgag | 1031 |
| Glu Glu | |
| agacgcaaga gagggagaga gatgggatgg gtgaaagatg tgcgctgata gggagggatg | 1091 |

```
                                                 -continued agagagaaaa aaacatggag aaagacgggg atgcagaaag agatgtggca agagatgggg     1151
aagagagaga gagaaagatg gagagacagg atgtctggca catggaaggt gctcactaag     1211
tgtgtatgga gtgaatgaat gaatgaatga atgaacaagc agatatataa ataagatatg     1271
gagacagatg tggggtgtga aagagagat  gggggaagaa acaagtgata tgaataaaga     1331
tggtgagaca gaaagagcgg gaaatatgac agctaaggag agagatgggg gagataagga     1391
gagaagaaga tagggtgtct ggcacacaga agacactcag ggaaagagct gttgaatgct     1451
ggaaggtgaa tacacagatg aatggagaga gaaaaccaga cacctcaggg ctaagagcgc     1511
aggccagaca ggcagccagc tgttcctcct ttaagggtga ctccctcgat gttaaccatt     1571
ctccttctcc ccaacag ttc ccc agg gac ctc tct cta atc agc cct ctg       1621
                   Phe Pro Arg Asp Leu Ser Leu Ile Ser Pro Leu
                                65                      70 gcc cag gca gtc agtaagtgtc tccaaacctc tttcctaatt ctgggtttgg          1673
Ala Gln Ala Val
        75 gtttggggt agggttagta ccggtatgga agcagtgggg gaaatttaaa gttttggtct     1733
tgggggagga tggatggagg tgaaagtagg ggggtatttt ctaggaagtt taagggtctc    1793 agcttttct tttctctctc ctcttca gga tca tct tct cga acc ccg agt gac     1847
                              Arg Ser Ser Ser Arg Thr Pro Ser Asp
                                                80              85 aag cct gta gcc cat gtt gta ggtaagagct ctgaggatgt gtcttggaac         1898
Lys Pro Val Ala His Val Val
                 90 ttggagggct aggatttggg gattgaagcc cggctgatgg taggcagaac ttggagacaa    1958 tgtgagaagg actcgctgag ctcaaggaa gggtggagga acagcacagg ccttagtggg    2018 atactcagaa cgtcatggcc aggtgggatg tgggatgaca gacagagagg acaggaaccg    2078 gatgtggggt gggcagagct cgagggccag gatgtggaga gtgaaccgac atggccacac    2138 tgactctcct ctccctctct ccctccctcc a gca aac cct caa gct gag ggg       2190
                                   Ala Asn Pro Gln Ala Glu Gly
                                                95              100 cag ctc cag tgg ctg aac cgc cgg gcc aat gcc ctc ctg gcc aat ggc      2238
Gln Leu Gln Trp Leu Asn Arg Arg Ala Asn Ala Leu Leu Ala Asn Gly
                 105                     110                 115 gtg gag ctg aga gat aac cag ctg gtg gtg cca tca gag ggc ctg tac      2286
Val Glu Leu Arg Asp Asn Gln Leu Val Val Pro Ser Glu Gly Leu Tyr
             120                     125                 130 ctc atc tac tcc cag gtc ctc ttc aag ggc caa ggc tgc ccc tcc acc      2334
Leu Ile Tyr Ser Gln Val Leu Phe Lys Gly Gln Gly Cys Pro Ser Thr
         135                     140                 145 cat gtg ctc ctc acc cac acc atc agc cgc atc gcc gtc tcc tac cag      2382
His Val Leu Leu Thr His Thr Ile Ser Arg Ile Ala Val Ser Tyr Gln
     150                     155                 160 acc aag gtc aac ctc ctc tct gcc atc aag agc ccc tgc cag agg gag      2430
Thr Lys Val Asn Leu Leu Ser Ala Ile Lys Ser Pro Cys Gln Arg Glu
165                     170                 175                 180 acc cca gag ggg gct gag gcc aag ccc tgg tat gag ccc atc tat ctg      2478
Thr Pro Glu Gly Ala Glu Ala Lys Pro Trp Tyr Glu Pro Ile Tyr Leu
             185                     190                 195 gga ggg gtc ttc cag ctg gag aag ggt gac cga ctc agc gct gag atc      2526
Gly Gly Val Phe Gln Leu Glu Lys Gly Asp Arg Leu Ser Ala Glu Ile
         200                     205                 210 aat cgg ccc gac tat ctc gac ttt gcc gag tct ggg cag gtc tac ttt      2574
Asn Arg Pro Asp Tyr Leu Asp Phe Ala Glu Ser Gly Gln Val Tyr Phe
     215                     220                 225
```

-continued

```
ggg atc att gcc ctg tga ggaggacgaa catccaacct tcccaaacgc      2622
Gly Ile Ile Ala Leu
    230 ctcccctgcc ccaatccctt tattacccc tccttcagac accctcaacc tcttctggct  2682 caaaaagaga attgggggct tagggtcgga acccaagctt agaactttaa gcaacaagac  2742 caccacttcg aaacctggga ttcaggaatg tgtggcctgc acagtgaagt gctggcaacc  2802 actaagaatt caaactgggg cctccagaac tcactgggc ctacagcttt gatccctgac   2862 atctggaatc tggagaccag ggagcctttg gttctggcca gaatgctgca ggacttgaga  2922 agacctcacc tagaaattga cacaagtgga ccttaggcct tcctctctcc agatgtttcc  2982 agacttcctt gagacacgga gcccagccct ccccatggag ccagctccct ctatttatgt  3042 ttgcacttgt gattatttat tatttattta ttatttattt atttacagat gaatgtattt  3102 atttgggaga ccggggtatc ctgggggacc caatgtagga gctgccttgg ctcagacatg  3162 ttttccgtga aaacggagct gaacaatagg ctgttcccat gtagccccct ggcctctgtg  3222 ccttcttttg attatgtttt ttaaaatatt tatctgatta agttgtctaa acaatgctga  3282 tttggtgacc aactgtcact cattgctgag cctctgctcc ccaggggagt tgtgtctgta  3342 atcgccctac tattcagtgg cgagaaataa agtttgctta gaaaagaaac atggtctcct  3402 tcttggaatt aattctgcat ctgcctcttc ttgtgggtgg gaagaagctc cctaagtcct  3462 ctctccacag gctttaagat ccctcggacc cagtcccatc cttagactcc tagggccctg  3522 gagaccctac ataaacaaag cccaacagaa tattcccat cccccaggaa acaagagcct   3582 gaacctaatt acctctccct cagggcatgg gaatttccaa ctctgggaat tc          3634
```

<210> SEQ ID NO: 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
catgctttca gtgctcat                                               18

<210> SEQ ID NO: 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tgagggagcg tctgctggct                                             20

<210> SEQ ID NO: 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gtgctcatgg tgtcctttcc                                             20

<210> SEQ ID NO: 5
<211> LENGTH: 20
<212> TYPE: DNA

```
<213> ORGANISM: Artificial Sequence
<220> FEATURE:
<223> OTHER INFORMATION: Synthetic

<400> SEQUENCE: 5
taatcacaag tgcaaacata                                                  20

<210> SEQ ID NO: 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
taccccggtc tcccaaataa                                                  20

<210> SEQ ID NO: 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
agcaccgcct ggagccct                                                    18

<210> SEQ ID NO: 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gctgaggaac aagcaccgcc                                                  20

<210> SEQ ID NO: 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
aggcagaaga gcgtggtggc                                                  20

<210> SEQ ID NO: 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
aaagtgcagc aggcagaaga                                                  20

<210> SEQ ID NO: 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
ttagagagag gtccctgg                                                    18
```

<210> SEQ ID NO: 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
tgactgcctg ggccagag                                            18

<210> SEQ ID NO: 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
gggttcgaga agatgatc                                            18

<210> SEQ ID NO: 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gggctacagg cttgtcactc                                          20

<210> SEQ ID NO: 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
cccctcagct tgagggtttg                                          20

<210> SEQ ID NO: 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ccattggcca ggagggcatt                                          20

<210> SEQ ID NO: 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
accaccagct ggttatctct                                          20

<210> SEQ ID NO: 18
<211> LENGTH: 20
<212> TYPE: DNA
<213> ORGANISM: Artificial Sequence
<220> FEATURE:

```
<223> OTHER INFORMATION: Synthetic

<400> SEQUENCE: 18
ctgggagtag atgaggtaca                                              20

<210> SEQ ID NO: 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
cccttgaaga ggacctggga                                              20

<210> SEQ ID NO: 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ggtgtgggtg aggagcacat                                              20

<210> SEQ ID NO: 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gtctggtagg agacggcgat                                              20

<210> SEQ ID NO: 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gcagagagga ggttgacctt                                              20

<210> SEQ ID NO: 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gcttggcctc agccccctct                                              20

<210> SEQ ID NO: 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cctcccagat agatgggctc                                              20
```

```
<210> SEQ ID NO: 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cccttctcca gctggaagac                                                   20

<210> SEQ ID NO: 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
atctcagcgc tgagtcggtc                                                   20

<210> SEQ ID NO: 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
tcgagatagt cgggccgatt                                                   20

<210> SEQ ID NO: 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
aagtagacct gcccagactc                                                   20

<210> SEQ ID NO: 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ggatgttcgt cctcctcaca                                                   20

<210> SEQ ID NO: 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
accctaagcc cccaattctc                                                   20

<210> SEQ ID NO: 31
<211> LENGTH: 20
<212> TYPE: DNA
<213> ORGANISM: Artificial Sequence
<220> FEATURE:
<223> OTHER INFORMATION: Synthetic
```

<400> SEQUENCE: 31
ccacacattc ctgaatccca                                                20

<210> SEQ ID NO: 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
aggccccagt gagttctgga                                                20

<210> SEQ ID NO: 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gtctccagat tccagatgtc                                                20

<210> SEQ ID NO: 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ctcaagtcct gcagcattct                                                20

<210> SEQ ID NO: 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tgggtccccc aggataccccc                                               20

<210> SEQ ID NO: 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
acggaaaaca tgtctgagcc                                                20

<210> SEQ ID NO: 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ctccgttttc acggaaaaca                                                20

<210> SEQ ID NO: 38
<211> LENGTH: 20

```
<212> TYPE: DNA
<213> ORGANISM: Artificial Sequence
<220> FEATURE:
<223> OTHER INFORMATION: Synthetic

<400> SEQUENCE: 38
gcctattgtt cagctccgtt                                         20

<210> SEQ ID NO: 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
ggtcaccaaa tcagcattgt t                                       21

<210> SEQ ID NO: 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
gaggctcagc aatgagtgac                                         20

<210> SEQ ID NO: 41
<211> LENGTH: 20
<212> TYPE: DNA
<213> ORGANISM: Artificial Sequence
<220> FEATURE:
<223> OTHER INFORMATION: control sequence

<400> SEQUENCE: 41
gcccaagctg gcatccgtca                                         20

<210> SEQ ID NO: 42
<211> LENGTH: 21
<212> TYPE: DNA
<213> ORGANISM: Artificial Sequence
<220> FEATURE:
<223> OTHER INFORMATION: control seqeuence

<400> SEQUENCE: 42
gccgaggtcc atgtcgtacg c                                       21

<210> SEQ ID NO: 43
<211> LENGTH: 18
<212> TYPE: DNA
<213> ORGANISM: Artificial Sequence
<220> FEATURE:
<223> OTHER INFORMATION: PCR primer

<400> SEQUENCE: 43
caggcggtgc ttgttcct                                           18

<210> SEQ ID NO: 44
<211> LENGTH: 22
<212> TYPE: DNA
<213> ORGANISM: Artificial Sequence
<220> FEATURE:
<223> OTHER INFORMATION: PCR primer

<400> SEQUENCE: 44
```
gccagagggc tgattagaga ga    22

<210> SEQ ID NO: 45
<211> LENGTH: 25
<212> TYPE: DNA
<213> ORGANISM: Artificial Sequence
<220> FEATURE:
<223> OTHER INFORMATION: PCR probe

<400> SEQUENCE: 45
cttctccttc ctgatcgtgg caggc    25

<210> SEQ ID NO: 46
<211> LENGTH: 19
<212> TYPE: DNA
<213> ORGANISM: Artificial Sequence
<220> FEATURE:
<223> OTHER INFORMATION: PCR primer

<400> SEQUENCE: 46
gaaggtgaag gtcggagtc    19

<210> SEQ ID NO: 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
gaagatggtg atgggatttc    20

<210> SEQ ID NO: 48
<211> LENGTH: 20
<212> TYPE: DNA
<213> ORGANISM: Artificial Sequence
<220> FEATURE:
<223> OTHER INFORMATION: PCR probe

<400> SEQUENCE: 48
caagcttccc gttctcagcc    20

<210> SEQ ID NO: 49
<211> LENGTH: 20
<212> TYPE: DNA
<213> ORGANISM: Artificial Sequence
<220> FEATURE:
<223> OTHER INFORMATION: control sequence

<400> SEQUENCE: 49
tctgagtagc agaggagctc    20

<210> SEQ ID NO: 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tgcgtctctc atttcccctt    20

<210> SEQ ID NO: 51
<211> LENGTH: 20
<212> TYPE: DNA
<213> ORGANISM: Artificial Sequence

```
<220> FEATURE:
<223> OTHER INFORMATION: Synthetic

<400> SEQUENCE: 51
tcccatctct ctccctctct                                          20

<210> SEQ ID NO: 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
cagcgcacat ctttcaccca                                          20

<210> SEQ ID NO: 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
tctctctcat ccctccctat                                          20

<210> SEQ ID NO: 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
cgtctttctc catgtttttt                                          20

<210> SEQ ID NO: 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
cacatctctt tctgcatccc                                          20

<210> SEQ ID NO: 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ctctcttccc catctcttgc                                          20

<210> SEQ ID NO: 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
gtctctccat ctttccttct                                          20
```

```
<210> SEQ ID NO: 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
ttccatgtgc cagacatcct                                              20

<210> SEQ ID NO: 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
atacacactt agtgagcacc                                              20

<210> SEQ ID NO: 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
ttcattcatt cattcactcc                                              20

<210> SEQ ID NO: 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
tatatctgct tgttcattca                                              20

<210> SEQ ID NO: 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
ctgtctccat atcttattta                                              20

<210> SEQ ID NO: 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
tctcttctca caccccacat                                              20

<210> SEQ ID NO: 64
<211> LENGTH: 20
<212> TYPE: DNA
<213> ORGANISM: Artificial Sequence
<220> FEATURE:
<223> OTHER INFORMATION: Synthetic
```

-continued

<400> SEQUENCE: 64
cacttgtttc ttcccccatc                                               20

<210> SEQ ID NO: 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
ctcaccatct ttattcatat                                               20

<210> SEQ ID NO: 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
atatttcccg ctctttctgt                                               20

<210> SEQ ID NO: 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
catctctctc cttagctgtc                                               20

<210> SEQ ID NO: 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
tcttctctcc ttatctcccc                                               20

<210> SEQ ID NO: 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
gtgtgccaga caccctatct                                               20

<210> SEQ ID NO: 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
tctttccctg agtgtcttct                                               20

<210> SEQ ID NO: 71
<211> LENGTH: 20

```
<212> TYPE: DNA
<213> ORGANISM: Artificial Sequence
<220> FEATURE:
<223> OTHER INFORMATION: Synthetic

<400> SEQUENCE: 71
accttccagc attcaacagc                                               20

<210> SEQ ID NO: 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
ctccattcat ctgtgtattc                                               20

<210> SEQ ID NO: 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
tgaggtgtct ggttttctct                                               20

<210> SEQ ID NO: 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
acacatcctc agagctctta                                               20

<210> SEQ ID NO: 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
ctagccctcc aagttccaag                                               20

<210> SEQ ID NO: 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
cgggcttcaa tccccaaatc                                               20

<210> SEQ ID NO: 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
```
aagttctgcc taccatcagc                                              20

<210> SEQ ID NO: 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gtccttctca cattgtctcc                                              20

<210> SEQ ID NO: 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
ccttcccttg agctcagcga                                              20

<210> SEQ ID NO: 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
ggcctgtgct gttcctccac                                              20

<210> SEQ ID NO: 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
cgttctgagt atcccactaa                                              20

<210> SEQ ID NO: 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
cacatcccac ctggccatga                                              20

<210> SEQ ID NO: 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
gtcctctctg tctgtcatcc                                              20

<210> SEQ ID NO: 84
<211> LENGTH: 20
<212> TYPE: DNA
<213> ORGANISM: Artificial Sequence

```
<220> FEATURE:
<223> OTHER INFORMATION: Synthetic

<400> SEQUENCE: 84
ccaccccaca tccggttcct

<210> SEQ ID NO: 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
tcctggccct cgagctctgc

<210> SEQ ID NO: 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
atgtcggttc actctccaca

<210> SEQ ID NO: 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
agaggagagt cagtgtggcc

<210> SEQ ID NO: 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
gatcccaaag tagacctgcc

<210> SEQ ID NO: 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
cagactcggc aaagtcgaga

<210> SEQ ID NO: 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
tagtcgggcc gattgatctc
```

<210> SEQ ID NO: 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
agcgctgagt cggtcaccct

<210> SEQ ID NO: 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
tctccagctg gaagacccct

<210> SEQ ID NO: 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
cccagataga tgggctcata

<210> SEQ ID NO: 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
ccagggcttg gcctcagccc

<210> SEQ ID NO: 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
cctctggggt ctccctctgg

<210> SEQ ID NO: 96
<211> LENGTH: 20
<212> TYPE: DNA
<213> ORGANISM: Artificial Sequence
<220> FEATURE:
<223> OTHER INFORMATION: Synthetic

<400> SEQUENCE: 96 cagggctct tgatggcaga

<210> SEQ ID NO: 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
gaggaggttg accttggtct

<210> SEQ ID NO: 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
ggtaggagac ggcgatgcgg

<210> SEQ ID NO: 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
ctgatggtgt gggtgaggag

<210> SEQ ID NO :100
<211> LENGTH: 20
<212> TYPE: DNA
<213> ORGANISM: Artificial Sequence
<220> FEATURE:
<223> OTHER INFORMATION: Synthetic

<400> SEQUENCE: 100
aggcactcac ctcttccctc

<210> SEQ ID NO :101
<211> LENGTH: 20
<212> TYPE: DNA
<213> ORGANISM: Artificial Sequence
<220> FEATURE:
<223> OTHER INFORMATION: Synthetic

<400> SEQUENCE: 101
ccctggggaa ctgttgggga

<210> SEQ ID NO :102
<211> LENGTH: 20
<212> TYPE: DNA
<213> ORGANISM: Artificial Sequence
<220> FEATURE:
<223> OTHER INFORMATION: Synthetic

<400> SEQUENCE: 102
agacacttac tgactgcctg

<210> SEQ ID NO :103
<211> LENGTH: 20
<212> TYPE: DNA
<213> ORGANISM: Artificial Sequence
<220> FEATURE:
<223> OTHER INFORMATION: Synthetic

<400> SEQUENCE: 103
gaagatgatc ctgaagagga

<210> SEQ ID NO :104

```
<211> LENGTH: 20
<212> TYPE: DNA
<213> ORGANISM: Artificial Sequence
<220> FEATURE:
<223> OTHER INFORMATION: Synthetic

<400> SEQUENCE: 104
gagctcttac ctacaacatg

<210> SEQ ID NO :105
<211> LENGTH: 20
<212> TYPE: DNA
<213> ORGANISM: Artificial Sequence
<220> FEATURE:
<223> OTHER INFORMATION: Synthetic

<400> SEQUENCE: 105
tgagggtttg ctggagggag                                                       20

<210> SEQ ID NO :106
<211> LENGTH: 20
<212> TYPE: DNA
<213> ORGANISM: Artificial Sequence
<220> FEATURE:
<223> OTHER INFORMATION: control sequence

<400> SEQUENCE: 106
gatcgcgtcg gactatgaag                                                       20

<210> SEQ ID NO: 107
<211> LENGTH: 7208
<212> TYPE: DNA
<213> ORGANISM: Mus musculus
<220> FEATURE:
<221> NAME/KEY: CDS
<222> LOCATION: (4527..4712,5225..5279,5457..5504,5799..6217)
<220> FEATURE:
<221> NAME/KEY: exon
<222> LOCATION: (4371)..(4712)
<220> FEATURE:
<221> NAME/KEY: intron
<222> LOCATION: (4713)..(5224)
<220> FEATURE:
<221> NAME/KEY: exon
<222> LOCATION: (5225)..(5279)
<220> FEATURE:
<221> NAME/KEY: intron
<222> LOCATION: (5280)..(5456)
<220> FEATURE:
<221> NAME/KEY: exon
<222> LOCATION: (5457)..(5504)
<220> FEATURE:
<221> NAME/KEY: intron
<222> LOCATION: (5505)..(5798)
<220> FEATURE:
<221> NAME/KEY: exon
<222> LOCATION: (5799)..(>6972)
<300> PUBLICATION INFORMATION:
<301> AUTHORS: Semon, D.
       Kawashima, E.
       Jongeneel, C.V.
       Shakhov, A.N.
       Nedospasov, S.A.
<302> TITLE: Nucleotide sequence of the murine TNF locus, including the
<302> TITLE: TNF-alpha (tumor necrosis factor) and TNF-beta
       (lymphotoxin)
<302> TITLE: genes
<303> JOURNAL: Nucleic Acids Res.
<304> VOLUME: 15
<305> ISSUE: 21
<306> PAGES: 9083-9084
<307> DATE: 1987-11-11
<308> DATABASE ACCESSION NUMBER: Y00467 Genbank
```

<309> DATABASE ENTRY DATE: 1993-05-11

<400> SEQUENCE: 107

| | | | | | |
|---|---|---|---|---|---:|
| gaattctgaa | gctccctctg | tacagagcat | tggaagcctg | gggtgtacat | ttggggttac | 60 |
| atgatcttgg | ggttctaaga | gaataccccc | aaatcatctt | ccagacctgg | aacattctag | 120 |
| gacagggttc | tcaaccttcc | taactccatg | acccttaat | acagttcctc | atgttgtggt | 180 |
| gaccccaacc | atacaattat | tttcgttgct | atttcataac | tgtaatttcg | ctgctattat | 240 |
| gaatcataat | gtaaatattt | gttttaaata | gaggtttgcc | aaagggacct | tgcccacagg | 300 |
| ttgagaactg | ccgctccaga | gagtaagggg | acacagttaa | gattgttaca | caccaggatg | 360 |
| ccccagattt | ggggagaggg | cactgtaatg | gaacttcttg | acatgaaact | ggcagatgaa | 420 |
| actggcagaa | aaaaaaaaaa | aagctgggca | gtggtggcac | acacctttaa | tcccagcact | 480 |
| tgggaggcag | aggcaggcgg | atttctgagt | tctaggccag | cctggtctac | agagtgagtt | 540 |
| tcaggacagc | cagggctaca | cagagaaacc | ctgtctcgaa | aaagcaaaa | aaaaaaaaa | 600 |
| aaaaaaaaaa | aaactggcag | atgaccagaa | aatacagata | tattggaata | actgtgactt | 660 |
| gaacccccaa | agacaagaga | ggaaataggc | ctgaagggc | ggcaggcatg | tcaagcatcc | 720 |
| agagccctgg | gttcgaacct | gaaaaaacaa | aggtgccgct | aaccacatgt | ggcttcggag | 780 |
| ccctccagac | atgaccatga | tcgacagaga | gggaaatgtg | cagagaagcc | tgtgagcagt | 840 |
| caagggtgca | gaagtgatat | aaaccatcac | tcttcaggga | accaggcttc | cagtcacagc | 900 |
| ccagctgcac | cctctccacg | aattgctcgg | ccgttcactg | gaactcctgg | gcctgaccca | 960 |
| gctccctgct | agtccctgcg | gcccacagtt | cccggaccc | gactcccttt | ccagaacgc | 1020 |
| agtagtctaa | gcccttagcc | tgcggttctc | tcctaggccc | cagcctttcc | tgccttcgac | 1080 |
| tgaaacagca | gcatcttcta | agccctgggg | gcttccccaa | gccccagccc | cgacctagaa | 1140 |
| cccgcccgct | gcctgccaca | ctgccgcttc | tctataaag | ggacccgagc | gccagcgccc | 1200 |
| aggacccgc | acagcaggtg | agcctctcct | accctgtctc | cttgggctta | ccctggtatc | 1260 |
| aggcatccct | caggatccta | cctcctttct | tgagccacag | cctttctat | acaacctgcc | 1320 |
| tggatcccca | gccttaatgg | gtctggtcct | cctgtcgtgg | ctttgatttt | tggtctgttc | 1380 |
| ctgtggcggc | cttatcagtc | tctctctctc | tctctctctc | tctctctctc | tctctctctc | 1440 |
| tctctctctc | tctccctctc | tctctctctc | tctctctctc | ttctctctct | ctgcctctgt | 1500 |
| tagccattgt | ctgattctat | ggtggagctt | tcctcttccc | ctctgtctct | ccttatccct | 1560 |
| gctcacttca | gggttcccct | gcctgtcccc | ttttctgtct | gtcgccctgt | ctctcagggt | 1620 |
| ggctgtctca | gctgggaggt | aagtctgtc | ttccgctgtg | tgccccgcct | ccgctacaca | 1680 |
| cacacactct | ctctctctct | ctcagcaggt | tctccacatg | acactgctcg | gccgtctcca | 1740 |
| cctcttgagg | gtgcttggca | cccctcctgt | cttcctcctg | gggctgctgc | tggccctgcc | 1800 |
| tctagggggcc | caggtgaggc | agcaagagat | tgggggtgct | ggggtggcct | agctaactca | 1860 |
| gagtcctaga | gtcctctcca | ctctcttctg | tcccagggac | tctctggtgt | ccgcttctcc | 1920 |
| gctgccagga | cagcccatcc | actccctcag | aagcacttga | cccatggcat | cctgaaacct | 1980 |
| gctgctcacc | ttgttggtaa | acttctgcct | ccagaggaga | ggtccagtcc | ctgccttttg | 2040 |
| tcctacttgc | ccagggctc | aggcgatctt | cccatctccc | cacaccaact | tttcttaccc | 2100 |
| ctaagggcag | gcaccccact | cccatctccc | taccaaccat | cccacttgtc | cagtgcctgc | 2160 |
| tcctcaggga | tggggacctc | tgatcttgat | agccccccaa | tgtcttgtgc | ctcttcccag | 2220 |
| ggtaccccag | caagcagaac | tcactgctct | ggagagcaag | cacggatcgt | gcctttctcc | 2280 |

```
gacatggctt ctctttgagc aacaactccc tcctgatccc caccagtggc ctctactttg   2340
tctactccca ggtggttttc tctggagaaa gctgctcccc cagggccatt cccactccca   2400
tctacctggc acacgaggtc cagctctttt cctcccaata ccccttccat gtgcctctcc   2460
tcagtgcgca gaagtctgtg tatccggggac ttcaaggacc gtgggtgcgc tcaatgtacc   2520 aggggctgt gttcctgctc agtaagggag accagctgtc cacccacacc gacggcatct   2580
cccatctaca cttcagcccc agcagtgtat tctttggagc ctttgcactg tagattctaa   2640
agaaacccaa gaattggatt ccaggcctcc atcctgaccg ttgtttcaag ggtcacatcc   2700
ccacagtctc cagccttccc cactaaaata acctggagct ctcacgggag tctgagacac   2760
ttcaggggac tacatcttcc ccagggccac tccagatgct caggggacga ctcaagccta   2820
cctagaagtt cctgcacaga gcaggttttt tgtgggtcta ggtcggacag agacctggac   2880
atgaaggagg gacagacatg ggagaggtgg ctgggaacag ggaaggttg actatttatg   2940 gagagaaaag ttaagttatt tatttataga gaatagaaag aggggaaaaa tagaaagccg   3000
tcagatgaca actaggtccc agacacaaag gtgtctcacc tcagacagga cccatctaag   3060
agagagatgg cgagagaatt agatgtgggt gaccaagggg ttctagaaga aagcacgaag   3120
ctctaaaagc cagccactgc ttggctagac atccacaggg accccctgca ccatctgtga   3180
aacccaataa acctcttttc tctgagattc tgtctgcttg tgtctgtctt gcgttggggg   3240
agaaacttcc tggtctcttt aaggagtgga gcagggggaca gaggcctcag ttggtccatg   3300
ggatccgggc agagcaaaga gacatgagga gcaggcagct cccagagaca tggtggattc   3360
acgggagtga ggcagcttaa ctgccgagag acccaaagga tgagctaggg agatccatcc   3420
aagggtggag agagatgagg gttctgggga gaagtgactc cactggaggg tgggagagtg   3480
tttaggagtg ggagggtggg ggaggggaat ccttggaaga ccggggagtc atacggattg   3540
ggagaaatcc tggaagcagg gctgtgggac ctaaatgtct gagttgatgt accgcagtca   3600
agatatggca gaggctccgt ggaaaactca cttgggagca gggacccaaa gcagcagcct   3660
gagctcatga tcagagtgaa aggagaaggc ttgtgaggtc cgtgaattcc cagggctgag   3720
ttcattccct ctgggctgcc ccatactcat cccattaccc cccccaccag ccctcccaaa   3780
gcccatgcac acttcccaac tctcaagctg ctctgccttc agccacttcc tccaagaact   3840
caaacagggg gctttccctc ctcaatatca tgtctccccc cttatgcacc cagctttcag   3900
aagcaccccc ccatgctaag ttctccccca tggatgtccc atttagaaat caaaggaaa   3960 tagacacagg catggtcttt ctacaaagaa acagacaatg attagctctg gaggacagag   4020
aagaaatggg tttcagttct cagggtccta tacaacacac acacacacac acacacacac   4080
acacacacac acacaccctc ctgattggcc ccagattgcc acagaatcct ggtggggacg   4140 acggggggaga gattccttga tgcctgggtg tccccaactt tccaaaccct ctgccccgc   4200 gatggagaag aaaccgagac agaggtgtag ggccactacc gcttcctcca catgagatca   4260
tggttttctc caccaaggaa gttttccgag ggttgaatga gagcttttcc ccgcctctct   4320
ccccaagggc tataaaggcg gccgtctgca cagccagcca gcagaagctc cctcagcgag   4380
gacagcaagg gactagccag gagggagaac agaaactcca gaacatcttg gaaatagctc   4440
ccagaaaagc aagcagccaa ccaggcaggt tctgtcccctt tcactcactg gcccaaggcg   4500
ccacatctcc ctccagaaaa gacacc atg agc aca gaa agc atg atc cgc gac   4553
                              Met Ser Thr Glu Ser Met Ile Arg Asp
                              1               5
```

```
gtg gaa ctg gca gaa gag gca ctc ccc caa aag atg ggg ggc ttc cag    4601
Val Glu Leu Ala Glu Glu Ala Leu Pro Gln Lys Met Gly Gly Phe Gln
 10              15                  20                  25 aac tcc agg cgg tgc cta tgt ctc agc ctc ttc tca ttc ctg ctt gtg    4649
Asn Ser Arg Arg Cys Leu Cys Leu Ser Leu Phe Ser Phe Leu Leu Val
            30                  35                  40 gca ggg gcc acc acg ctc ttc tgt cta ctg aac ttc ggg gtg atc ggt    4697
Ala Gly Ala Thr Thr Leu Phe Cys Leu Leu Asn Phe Gly Val Ile Gly
                45                  50                  55 ccc caa agg gat gag gtgagtgtct gggcaaccct tattctcgct cacaagcaaa    4752
Pro Gln Arg Asp Glu
            60 acgggttagg agggcaagaa ggacagtgtg agggaaagaa gtgggctaat gggcagggca    4812 aggtggagga gagtgtggag gggacagagt caggacctcg gacccatgcg tccagctgac    4872 taaacatcct tcgtcggatg cacagagaga tgaatgaacg aacaagtgtg ttcacacgtg    4932 gagagatctg gaaagatgtg gccagggaaa gaggggataa gcaagagata aaactcagag    4992 acagaaatga gagaggcatg agagataagg aggaagatga aggggagata acgggagatc    5052 aagcacagag ggcaccgcag aaagaagccg tgggttggac agatgaatga atgaagaaga    5112 aaacacaaag tgggggtgg gtggggcaaa gaggaactgt aagcgggca atcagccggg    5172 agcttctcct ttggggtgag tctgtcttaa ctaacctcct tttcctacac ag aag ttc    5230
                                                        Lys Phe cca aat ggc ctc cct ctc atc agt tct atg gcc cag acc ctc aca ctc    5278
Pro Asn Gly Leu Pro Leu Ile Ser Ser Met Ala Gln Thr Leu Thr Leu
 65              70                  75                  80 agtaagtgtt cccacacctc tctcttaatt taagatggag aagggcagtt aggcatggga    5338
Arg tgagatgggg tgggggaaa acttaaagct ttggtttggg aggaaagggg tctaagtgca    5398
tagatgcttc ctgggaagcc taaaaggctc atccttgcct ttgtctcttc ccctcca      5455 gga tca tct tct caa aat tcg agt gac aag cct gta gcc cac gtc gta    5503
    Ser Ser Ser Gln Asn Ser Ser Asp Lys Pro Val Ala His Val Val
                85                  90                  95 ggtaagattt ctttacatgt gccttgagaa tgaagggca tgattttggg gggcgggttg    5563
aggggtgtcg agccaggctg agaaaagaca gagctcttag agacagcacg tgagagtcag    5623
agcagtgact caaaagcaag gcatcagggg gccacccggg acctcatagc caatgggatg    5683
tggaaagaca gagggtgcag gaaccggaag tgaagtgtgg gtagctgctg aggctcagga    5743
tgtggagtgt gaactaagag ggtgacactg actcaatcct cccccccccc ctca gca     5800
                                                              Ala aac cac caa gtg gag gag cag ctg gag tgg ctg agc cag cgc gcc aac    5848
Asn His Gln Val Glu Glu Gln Leu Glu Trp Leu Ser Gln Arg Ala Asn
            100                 105                 110 gcc ctc ctg gcc aac ggc atg gat ctc aaa gac aac caa cta gtg gtg    5896
Ala Leu Leu Ala Asn Gly Met Asp Leu Lys Asp Asn Gln Leu Val Val
115                 120                 125 cca gcc gat ggg ttg tac ctt gtc tac tcc cag gtt ctc ttc aag gga    5944
Pro Ala Asp Gly Leu Tyr Leu Val Tyr Ser Gln Val Leu Phe Lys Gly
130                 135                 140                 145 caa ggc tgc ccc gac tac gtg ctc ctc acc cac acc gtc agc cga ttt    5992
Gln Gly Cys Pro Asp Tyr Val Leu Leu Thr His Thr Val Ser Arg Phe
                150                 155                 160 gct atc tca tac cag gag aaa gtc aac ctc ctc tct gcc gtc aag agc    6040
Ala Ile Ser Tyr Gln Glu Lys Val Asn Leu Leu Ser Ala Val Lys Ser
                165                 170                 175
```

| | | |
|---|---|---|
| ccc tgc ccc aag gac acc cct gag ggg gct gag ctc aaa ccc tgg tat | | 6088 |
| Pro Cys Pro Lys Asp Thr Pro Glu Gly Ala Glu Leu Lys Pro Trp Tyr | | |
| 180 185 190 | | |

| | | |
|---|---|---|
| gag ccc ata tac ctg gga gga gtc ttc cag ctg gag aag ggg gac caa | | 6136 |
| Glu Pro Ile Tyr Leu Gly Gly Val Phe Gln Leu Glu Lys Gly Asp Gln | | |
| 195 200 205 | | |

| | | |
|---|---|---|
| ctc agc gct gag gtc aat ctg ccc aag tac tta gac ttt gcg gag tcc | | 6184 |
| Leu Ser Ala Glu Val Asn Leu Pro Lys Tyr Leu Asp Phe Ala Glu Ser | | |
| 210 215 220 225 | | |

| | | |
|---|---|---|
| ggg cag gtc tac ttt gga gtc att gct ctg tga agggaatggg tgttcatcca | | 6237 |
| Gly Gln Val Tyr Phe Gly Val Ile Ala Leu | | |
| 230 235 | | |

| | |
|---|---|
| ttctctaccc agcccccact ctgacccctt tactctgacc cctttattgt ctactcctca | 6297 |
| gagcccccag tctgtgtcct tctaacttag aaagggatt atggctcaga gtccaactct | 6357 |
| gtgctcagag ctttcaacaa ctactcagaa acacaagatg ctgggacagt gacctggact | 6417 |
| gtgggcctct catgcaccac catcaaggac tcaaatgggc tttccgaatt cactggagcc | 6477 |
| tcgaatgtcc attcctgagt tctgcaaagg gagagtggtc aggttgcctc tgtctcagaa | 6537 |
| tgaggctgga taagatctca ggccttccta ccttcagacc tttccagact cttccctgag | 6597 |
| gtgcaatgca cagccttcct cacagagcca gccccctct atttatattt gcacttatta | 6657 |
| tttattattt atttattatt tatttatttg cttatgaatg tatttatttg gaaggccggg | 6717 |
| gtgtcctgga ggacccagtg tgggaagctg tcttcagaca gacatgtttt ctgtgaaaac | 6777 |
| ggagctgagc tgtccccacc tggcctctct accttgttgc ctcctctttt gcttatgttt | 6837 |
| aaaacaaaat atttatctaa cccaattgtc ttaataacgc tgatttggtg accaggctgt | 6897 |
| cgctacatca ctgaacctct gctccccacg ggagccgtga ctgtaattgc cctacagtca | 6957 |
| attgagagaa ataaagatcg cttggaaaag aaatgtgatt tctgtcttgg gatgaagtct | 7017 |
| gcatccatct ctttgcggag gcctaaagtc tctgggtcca gatctcagtc tttataccc | 7077 |
| tgggccatta agaccccaa gaccccgtg gaacaaaagg cagccaacat ccctacctct | 7137 |
| cccccggaaa caggagccta accctaatta cctttgccct ggggcatggg aatttcccac | 7197 |
| tctgggaatt c | 7208 |

<210> SEQ ID NO: 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
gagcttctgc tggctggctg           20

<210> SEQ ID NO: 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
ccttgctgtc ctcgctgagg           20

<210> SEQ ID NO: 110
<211> LENGTH: 20
<212> TYPE: DNA
<213> ORGANISM: Artificial Sequence

```
<220> FEATURE:
<223> OTHER INFORMATION: Synthetic

<400> SEQUENCE: 110
tcatggtgtc ttttctggag                                                    20

<210> SEQ ID NO: 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
ctttctgtgc tcatggtgtc                                                    20

<210> SEQ ID NO: 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
gcggatcatg ctttctgtgc                                                    20

<210> SEQ ID NO: 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
gggaggccat ttgggaactt                                                    20

<210> SEQ ID NO: 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
cgaattttga gaagatgatc                                                    20

<210> SEQ ID NO: 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
ctcctccact tggtggtttg                                                    20

<210> SEQ ID NO: 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
cctgagatct tatccagcct                                                    20
```

```
<210> SEQ ID NO: 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
caattacagt cacggctccc                                              20

<210> SEQ ID NO: 118
<211> LENGTH: 20
<212> TYPE: DNA
<213> ORGANISM: Artificial Sequence

<400> SEQUENCE: 118
cccttcattc tcaaggcaca                                              20

<210> SEQ ID NO: 119
<211> LENGTH: 20
<212> TYPE: DNA
<213> ORGANISM: Artificial Sequence
<220> FEATURE:
<223> OTHER INFORMATION: Synthetic

<400> SEQUENCE: 119 caccectcaa cccgccccc                                               20

<210> SEQ ID NO: 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
agagctctgt cttttctcag                                              20

<210> SEQ ID NO: 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
cactgctctg actctcacgt                                              20

<210> SEQ ID NO: 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
atgaggtccc gggtggcccc                                              20

<210> SEQ ID NO: 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
``` cacccctctgt ctttccacat                                              20

<210> SEQ ID NO: 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
ctccacatcc tgagcctcag                                               20

<210> SEQ ID NO: 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
attgagtcag tgtcaccctc                                               20

<210> SEQ ID NO: 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
gctggctcag ccactccagc                                               20

<210> SEQ ID NO: 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
tctttgagat ccatgccgtt                                               20

<210> SEQ ID NO: 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
aacccatcgg ctggcaccac                                               20

<210> SEQ ID NO: 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
gtttgagctc agcccccctca                                              20

<210> SEQ ID NO: 130
<211> LENGTH: 20
<212> TYPE: DNA
<213> ORGANISM: Artificial Sequence

```
<220> FEATURE:
<223> OTHER INFORMATION: Synthetic

<400> SEQUENCE: 130
ctcctcccag gtatatgggc                                               20

<210> SEQ ID NO: 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
tgagttggtc cccttctcc                                                20

<210> SEQ ID NO: 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
caaagtagac ctgcccggac                                               20

<210> SEQ ID NO: 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
acacccattc ccttcacaga                                               20

<210> SEQ ID NO: 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
cataatcccc tttctaagtt                                               20

<210> SEQ ID NO: 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
cacagagttg gactctgagc                                               20

<210> SEQ ID NO: 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
cagcatcttg tgtttctgag                                               20
```

```
<210> SEQ ID NO: 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
cacagtccag gtcactgtcc                                                    20

<210> SEQ ID NO: 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
tgatggtggt gcatgagagg                                                    20

<210> SEQ ID NO: 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
gtgaattcgg aaagcccatt                                                    20

<210> SEQ ID NO: 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
cctgaccact ctccctttgc                                                    20

<210> SEQ ID NO: 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
tgcatccccc aggccaccat                                                    20

<210> SEQ ID NO: 142
<211> LENGTH: 21
<212> TYPE: DNA
<213> ORGANISM: Artificial Sequence
<220> FEATURE:
<223> OTHER INFORMATION: Synthetic

<400> SEQUENCE: 142
gccgaggtcc atgtcgtacg c                                                  21

<210> SEQ ID NO: 143
<211> LENGTH: 20
<212> TYPE: DNA
<213> ORGANISM: Artificial Sequence
<220> FEATURE:
<223> OTHER INFORMATION: Synthetic
```

<400> SEQUENCE: 143
tcaagcagtg ccaccgatcc                                              20

<210> SEQ ID NO: 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
agtgtcttct gtgtgccaga                                              20

<210> SEQ ID NO: 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
gtgtcttctg tgtgccagac                                              20

<210> SEQ ID NO: 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
tgtcttctgt gtgccagaca                                              20

<210> SEQ ID NO: 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
gtcttctgtg tgccagacac                                              20

<210> SEQ ID NO: 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
tcttctgtgt gccagacacc                                              20

<210> SEQ ID NO: 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
cttctgtgtg ccagacaccc                                              20

<210> SEQ ID NO: 150

```
<211> LENGTH: 20
<212> TYPE: DNA
<213> ORGANISM: Artificial Sequence
<220> FEATURE:
<223> OTHER INFORMATION: Synthetic

<400> SEQUENCE: 150
ttctgtgtgc cagacaccct                                            20

<210> SEQ ID NO: 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
tctgtgtgcc agacacccta                                            20

<210> SEQ ID NO: 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
ctgtgtgcca gacaccctat                                            20

<210> SEQ ID NO: 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
tgtgtgccag acaccctatc                                            20

<210> SEQ ID NO: 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
tgtgccagac accctatctt                                            20

<210> SEQ ID NO: 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
gtgccagaca ccctatcttc                                            20

<210> SEQ ID NO: 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
```
tgccagacac cctatcttct                                                       20

<210> SEQ ID NO: 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
gccagacacc ctatcttctt                                                       20

<210> SEQ ID NO: 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
ccagacaccc tatcttcttc                                                       20

<210> SEQ ID NO: 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
cagacaccct atcttcttct                                                       20

<210> SEQ ID NO: 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
agacacccta tcttcttctc                                                       20

<210> SEQ ID NO: 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
gacaccctat cttcttctct                                                       20

<210> SEQ ID NO: 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
acaccctatc ttcttctctc                                                       20

<210> SEQ ID NO: 163
<211> LENGTH: 20
<212> TYPE: DNA

```
<213> ORGANISM: Artificial Sequence
<220> FEATURE:
<223> OTHER INFORMATION: Synthetic

<400> SEQUENCE: 163
caccctatct tcttctctcc                                              20

<210> SEQ ID NO: 164
<211> LENGTH: 18
<212> TYPE: DNA
<213> ORGANISM: Artificial Sequence
<220> FEATURE:
<223> OTHER INFORMATION: Synthetic

<400> SEQUENCE: 164
gtcttctgtg tgccagac                                                18

<210> SEQ ID NO: 165
<211> LENGTH: 18
<212> TYPE: DNA
<213> ORGANISM: Artificial Sequence
<220> FEATURE:
<223> OTHER INFORMATION: Synthetic

<400> SEQUENCE: 165
tcttctgtgt gccagaca                                                18

<210> SEQ ID NO: 166
<211> LENGTH: 18
<212> TYPE: DNA
<213> ORGANISM: Artificial Sequence
<220> FEATURE:
<223> OTHER INFORMATION: Synthetic

<400> SEQUENCE: 166
cttctgtgtg ccagacac                                                18

<210> SEQ ID NO: 167
<211> LENGTH: 18
<212> TYPE: DNA
<213> ORGANISM: Artificial Sequence
<220> FEATURE:
<223> OTHER INFORMATION: Synthetic

<400> SEQUENCE: 167
ttctgtgtgc cagacacc                                                18

<210> SEQ ID NO: 168
<211> LENGTH: 18
<212> TYPE: DNA
<213> ORGANISM: Artificial Sequence
<220> FEATURE:
<223> OTHER INFORMATION: Synthetic

<400> SEQUENCE: 168
tctgtgtgcc agacaccc                                                18

<210> SEQ ID NO: 169
<211> LENGTH: 18
<212> TYPE: DNA
<213> ORGANISM: Artificial Sequence
<220> FEATURE:
<223> OTHER INFORMATION: Synthetic

<400> SEQUENCE: 169
ctgtgtgcca gacaccct                                                18
```

<210> SEQ ID NO: 170
<211> LENGTH: 18
<212> TYPE: DNA
<213> ORGANISM: Artificial Sequence
<220> FEATURE:
<223> OTHER INFORMATION: Synthetic

<400> SEQUENCE: 170
tgtgtgccag acacccta                                                18

<210> SEQ ID NO: 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
gtgtgccaga cacccuat                                                18

<210> SEQ ID NO: 172
<211> LENGTH: 18
<212> TYPE: DNA
<213> ORGANISM: Artificial Sequence
<220> FEATURE:
<223> OTHER INFORMATION: Synthetic

<400> SEQUENCE: 172
tgtgccagac accctatc                                                18

<210> SEQ ID NO: 173
<211> LENGTH: 18
<212> TYPE: DNA
<213> ORGANISM: Artificial Sequence
<220> FEATURE:
<223> OTHER INFORMATION: Synthetic

<400> SEQUENCE: 173
tgccagacac cctatctt                                                18

<210> SEQ ID NO: 174
<211> LENGTH: 18
<212> TYPE: DNA
<213> ORGANISM: Artificial Sequence
<220> FEATURE:
<223> OTHER INFORMATION: Synthetic

<400> SEQUENCE: 174
gccagacacc ctatcttc                                                18

<210> SEQ ID NO: 175
<211> LENGTH: 18
<212> TYPE: DNA
<213> ORGANISM: Artificial Sequence
<220> FEATURE:
<223> OTHER INFORMATION: Synthetic

<400> SEQUENCE: 175
ccagacaccc tatcttct                                                18

<210> SEQ ID NO: 176
<211> LENGTH: 18
<212> TYPE: DNA
<213> ORGANISM: Artificial Sequence
<220> FEATURE:

<223> OTHER INFORMATION: Synthetic

<400> SEQUENCE: 176
cagacaccct atcttctt                                    18

<210> SEQ ID NO: 177
<211> LENGTH: 18
<212> TYPE: DNA
<213> ORGANISM: Artificial Sequence
<220> FEATURE:
<223> OTHER INFORMATION: Synthetic

<400> SEQUENCE: 177
agacacccta tcttcttc                                    18

<210> SEQ ID NO: 178
<211> LENGTH: 18
<212> TYPE: DNA
<213> ORGANISM: Artificial Sequence
<220> FEATURE:
<223> OTHER INFORMATION: Synthetic

<400> SEQUENCE: 178
gacaccctat cttcttct                                    18

<210> SEQ ID NO: 179
<211> LENGTH: 18
<212> TYPE: DNA
<213> ORGANISM: Artificial Sequence
<220> FEATURE:
<223> OTHER INFORMATION: Synthetic

<400> SEQUENCE: 179
acaccctatc ttcttctc                                    18

<210> SEQ ID NO: 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
agaggtttgg agacacttac                                  20

<210> SEQ ID NO: 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
gaattaggaa agaggtttgg                                  20

<210> SEQ ID NO: 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
cccaaaccca gaattaggaa                                  20

<210> SEQ ID NO: 183
<211> LENGTH: 20
<212> TYPE: DNA
<213> ORGANISM: Artificial Sequence
<220> FEATURE:
<223> OTHER INFORMATION: Synthetic

<400> SEQUENCE: 183 taccccaaa cccaaaccca                    20

<210> SEQ ID NO: 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
gtactaaccc taccccaaa                    20

<210> SEQ ID NO: 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
ttccataccg gtactaaccc                    20

<210> SEQ ID NO: 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
cccccactgc ttccataccg                    20

<210> SEQ ID NO: 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
ctttaaattt cccccactgc                    20

<210> SEQ ID NO: 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
aagaccaaaa ctttaaattt                    20

<210> SEQ ID NO: 189
<211> LENGTH: 20
<212> TYPE: DNA
<213> ORGANISM: Artificial Sequence
<220> FEATURE:
<223> OTHER INFORMATION: Synthetic

```
<400> SEQUENCE: 189
atcctccccc aagaccaaaa                                              20

<210> SEQ ID NO: 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
acctccatcc atcctccccc                                              20

<210> SEQ ID NO: 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
ccctactttc acctccatcc                                              20

<210> SEQ ID NO: 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
gaaaataccc ccctactttc                                              20

<210> SEQ ID NO: 193
<211> LENGTH: 20
<212> TYPE: DNA
<213> ORGANISM: Artificial Sequence
<220> FEATURE:
<223> OTHER INFORMATION: Synthetic

<400> SEQUENCE: 193
aaacttccta gaaaataccc                                              20

<210> SEQ ID NO: 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
tgagaccctt aaacttccta                                              20

<210> SEQ ID NO: 195
<211> LENGTH: 20
<212> TYPE: DNA
<213> ORGANISM: Artificial Sequence
<220> FEATURE:
<223> OTHER INFORMATION: Synthetic

<400> SEQUENCE: 195 aagaaaagc tgagaccctt                                               20

<210> SEQ ID NO: 196
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 196
ggagagagaa aagaaaaagc                                              20

<210> SEQ ID NO: 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
tgagccagaa gaggttgagg                                              20

<210> SEQ ID NO: 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
attctctttt tgagccagaa                                              20

<210> SEQ ID NO: 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
taagccccca attctctttt                                              20

<210> SEQ ID NO: 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
gttccgaccc taagccccca                                              20

<210> SEQ ID NO: 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
ctaagcttgg gttccgaccc                                              20

<210> SEQ ID NO: 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
```

```
gcttaaagtt ctaagcttgg                                              20

<210> SEQ ID NO: 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
tggtcttgtt gcttaaagtt                                              20

<210> SEQ ID NO: 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
ttcgaagtgg tggtcttgtt                                              20

<210> SEQ ID NO: 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
aatcccaggt ttcgaagtgg                                              20

<210> SEQ ID NO: 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
cacattcctg aatcccaggt                                              20

<210> SEQ ID NO: 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
gtgcaggcca cacattcctg                                              20

<210> SEQ ID NO: 208
<211> LENGTH: 20
<212> TYPE: DNA
<213> ORGANISM: Artificial Sequence
<220> FEATURE:
<223> OTHER INFORMATION: Synthetic

<400> SEQUENCE: 208
gcacttcact gtgcaggcca                                              20

<210> SEQ ID NO: 209
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 209
gtggttgcca gcacttcact                                               20

<210> SEQ ID NO: 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
tgaattctta gtggttgcca                                               20

<210> SEQ ID NO: 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
ggccccagtt tgaattctta                                               20

<210> SEQ ID NO: 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
gagttctgga ggccccagtt                                               20

<210> SEQ ID NO: 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
aggccccagt gagttctgga                                               20

<210> SEQ ID NO: 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
tcaaagctgt aggccccagt                                               20

<210> SEQ ID NO: 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
atgtcaggga tcaaagctgt                                               20
```

<210> SEQ ID NO: 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
cagattccag atgtcaggga                                           20

<210> SEQ ID NO: 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
ccctggtctc cagattccag                                           20

<210> SEQ ID NO: 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
accaaaggct ccctggtctc                                           20

<210> SEQ ID NO: 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
tctggccaga accaaaggct                                           20

<210> SEQ ID NO: 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
cctgcagcat tctggccaga                                           20

<210> SEQ ID NO: 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
cttctcaagt cctgcagcat                                           20

<210> SEQ ID NO: 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
taggtgaggt cttctcaagt                                                     20

<210> SEQ ID NO: 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
tgtcaatttc taggtgaggt                                                     20

<210> SEQ ID NO: 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
ggtccacttg tgtcaatttc                                                     20

<210> SEQ ID NO: 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
gaaggcctaa ggtccacttg                                                     20

<210> SEQ ID NO: 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
ctggagagag gaaggcctaa                                                     20

<210> SEQ ID NO: 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
ctggaaacat ctggagagag                                                     20

<210> SEQ ID NO: 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
tcaaggaagt ctggaaacat                                                     20

<210> SEQ ID NO: 229

-continued

<211> LENGTH: 20
<212> TYPE: DNA
<213> ORGANISM: Artificial Sequence
<220> FEATURE:
<223> OTHER INFORMATION: Synthetic

<400> SEQUENCE: 229
gctccgtgtc tcaaggaagt                                              20

<210> SEQ ID NO: 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
ataaatacat tcatctgtaa                                              20

<210> SEQ ID NO: 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
ggtctcccaa ataaatacat                                              20

<210> SEQ ID NO: 232
<211> LENGTH: 20
<212> TYPE: DNA
<213> ORGANISM: Artificial Sequence
<220> FEATURE:
<223> OTHER INFORMATION: Synthetic

<400> SEQUENCE: 232 aggataccccc ggtctcccaa                                             20

<210> SEQ ID NO: 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
tgggtccccc aggataccccc                                             20

<210> SEQ ID NO: 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
gctcctacat tgggtccccc                                              20

<210> SEQ ID NO: 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
agccaaggca gctcctacat                                    20

<210> SEQ ID NO: 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
aacatgtctg agccaaggca                                    20

<210> SEQ ID NO: 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
tttcacggaa aacatgtctg                                    20

<210> SEQ ID NO: 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
tcagctccgt tttcacggaa                                    20

<210> SEQ ID NO: 239
<211> LENGTH: 20
<212> TYPE: DNA
<213> ORGANISM: Artificial Sequence
<220> FEATURE:
<223> OTHER INFORMATION: Synthetic

<400> SEQUENCE: 239
agcctattgt tcagctccgt                                    20

<210> SEQ ID NO: 240
<211> LENGTH: 20
<212> TYPE: DNA
<213> ORGANISM: Artificial Sequence
<220> FEATURE:
<223> OTHER INFORMATION: Synthetic

<400> SEQUENCE: 240
acatgggaac agcctattgt                                    20

<210> SEQ ID NO: 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
atcaaaagaa ggcacagagg                                    20

<210> SEQ ID NO: 242
<211> LENGTH: 20
<212> TYPE: DNA

<213> ORGANISM: Artificial Sequence
<220> FEATURE:
<223> OTHER INFORMATION: Synthetic

<400> SEQUENCE: 242
gtttagacaa cttaatcaga                    20

<210> SEQ ID NO: 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
aatcagcatt gtttagacaa                    20

<210> SEQ ID NO: 244
<211> LENGTH: 20
<212> TYPE: DNA
<213> ORGANISM: Artificial Sequence
<220> FEATURE:
<223> OTHER INFORMATION: Synthetic

<400> SEQUENCE: 244
ttggtcacca aatcagcatt                    20

<210> SEQ ID NO: 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
tgagtgacag ttggtcacca                    20

<210> SEQ ID NO: 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
ggctcagcaa tgagtgacag                    20

<210> SEQ ID NO: 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
attacagaca caactcccct                    20

<210> SEQ ID NO: 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
tagtagggcg attacagaca                    20

<210> SEQ ID NO: 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
cgccactgaa tagtagggcg                                               20

<210> SEQ ID NO: 250
<211> LENGTH: 20
<212> TYPE: DNA
<213> ORGANISM: Artificial Sequence
<220> FEATURE:
<223> OTHER INFORMATION: Synthetic

<400> SEQUENCE: 250
ctttatttct cgccactgaa                                               20

<210> SEQ ID NO: 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
ctgagggagc gtctgctggc                                               20

<210> SEQ ID NO: 252
<211> LENGTH: 20
<212> TYPE: DNA
<213> ORGANISM: Artificial Sequence
<220> FEATURE:
<223> OTHER INFORMATION: Synthetic

<400> SEQUENCE: 252
ccttgctgag ggagcgtctg                                               20

<210> SEQ ID NO: 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
ctggtcctct gctgtccttg                                               20

<210> SEQ ID NO: 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
cctctgctgt ccttgctgag                                               20

<210> SEQ ID NO: 255
<211> LENGTH: 20
<212> TYPE: DNA
<213> ORGANISM: Artificial Sequence
<220> FEATURE:

<223> OTHER INFORMATION: Synthetic

<400> SEQUENCE: 255
ttctctccct cttagctggt                                                    20

<210> SEQ ID NO: 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
tccctcttag ctggtcctct                                                    20

<210> SEQ ID NO: 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
tctgagggtt gttttcaggg                                                    20

<210> SEQ ID NO: 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
ctgtagttgc ttctctccct                                                    20

<210> SEQ ID NO: 259
<211> LENGTH: 20
<212> TYPE: DNA
<213> ORGANISM: Artificial Sequence
<220> FEATURE:
<223> OTHER INFORMATION: Synthetic

<400> SEQUENCE: 259
acctgcctgg cagcttgtca                                                    20

<210> SEQ ID NO: 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
ggatgtggcg tctgagggtt                                                    20

<210> SEQ ID NO: 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
tgtgagagga agagaacctg                                                    20

-continued

```
<210> SEQ ID NO: 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
gaggaagaga acctgcctgg                                                    20

<210> SEQ ID NO: 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
agccgtgggt cagtatgtga                                                    20

<210> SEQ ID NO: 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
tgggtcagta tgtgagagga                                                    20

<210> SEQ ID NO: 265
<211> LENGTH: 20
<212> TYPE: DNA
<213> ORGANISM: Artificial Sequence
<220> FEATURE:
<223> OTHER INFORMATION: Synthetic

<400> SEQUENCE: 265
gagagggtga agccgtgggt                                                    20

<210> SEQ ID NO: 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
tcatggtgtc ctttccaggg                                                    20

<210> SEQ ID NO: 267
<211> LENGTH: 20
<212> TYPE: DNA
<213> ORGANISM: Artificial Sequence
<220> FEATURE:
<223> OTHER INFORMATION: Synthetic

<400> SEQUENCE: 267
ctttcagtgc tcatggtgtc                                                    20

<210> SEQ ID NO: 268
<211> LENGTH: 20
<212> TYPE: DNA
<213> ORGANISM: Artificial Sequence
<220> FEATURE:
<223> OTHER INFORMATION: Synthetic
```

-continued

```
<400> SEQUENCE: 268
tcatgctttc agtgctcatg                                              20

<210> SEQ ID NO: 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
acgtcccgga tcatgctttc                                              20

<210> SEQ ID NO: 270
<211> LENGTH: 20
<212> TYPE: DNA
<213> ORGANISM: Artificial Sequence
<220> FEATURE:
<223> OTHER INFORMATION: Synthetic

<400> SEQUENCE: 270
gctccacgtc ccggatcatg                                              20

<210> SEQ ID NO: 271
<211> LENGTH: 20
<212> TYPE: DNA
<213> ORGANISM: Artificial Sequence
<220> FEATURE:
<223> OTHER INFORMATION: Synthetic

<400> SEQUENCE: 271
tcctcggcca gctccacgtc                                              20

<210> SEQ ID NO: 272
<211> LENGTH: 20
<212> TYPE: DNA
<213> ORGANISM: Artificial Sequence
<220> FEATURE:
<223> OTHER INFORMATION: Synthetic

<400> SEQUENCE: 272
gcgcctcctc ggccagctcc                                              20

<210> SEQ ID NO: 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
aggaacaagc accgcctgga                                              20

<210> SEQ ID NO: 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
caagcaccgc ctggagccct                                              20

<210> SEQ ID NO: 275
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 275
aaggagaaga ggctgaggaa                                                    20

<210> SEQ ID NO: 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
gaagaggctg aggaacaagc                                                    20

<210> SEQ ID NO: 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
cctgccacga tcaggaagga                                                    20

<210> SEQ ID NO: 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
cacgatcagg aaggagaaga                                                    20

<210> SEQ ID NO: 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
aagagcgtgg tggcgcctgc                                                    20

<210> SEQ ID NO: 280
<211> LENGTH: 20
<212> TYPE: DNA
<213> ORGANISM: Artificial Sequence
<220> FEATURE:
<223> OTHER INFORMATION: Synthetic

<400> SEQUENCE: 280
cgtggtggcg cctgccacga                                                    20

<210> SEQ ID NO: 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
```
aagtgcagca ggcagaagag                                            20

<210> SEQ ID NO: 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
cagcaggcag aagagcgtgg                                            20

<210> SEQ ID NO: 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
gatcactcca aagtgcagca                                            20

<210> SEQ ID NO: 284
<211> LENGTH: 20
<212> TYPE: DNA
<213> ORGANISM: Artificial Sequence
<220> FEATURE:
<223> OTHER INFORMATION: Synthetic

<400> SEQUENCE: 284
gggccgatca ctccaaagtg                                            20

<210> SEQ ID NO: 285
<211> LENGTH: 20
<212> TYPE: DNA
<213> ORGANISM: Artificial Sequence
<220> FEATURE:
<223> OTHER INFORMATION: Synthetic

<400> SEQUENCE: 285
gggccagagg gctgattaga                                            20

<210> SEQ ID NO: 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
agagggctga ttagagagag                                            20

<210> SEQ ID NO: 287
<211> LENGTH: 20
<212> TYPE: DNA
<213> ORGANISM: Artificial Sequence
<220> FEATURE:
<223> OTHER INFORMATION: Synthetic

<400> SEQUENCE: 287
gctacaggct tgtcactcgg                                            20

<210> SEQ ID NO: 288
<211> LENGTH: 20
<212> TYPE: DNA
<213> ORGANISM: Artificial Sequence

```
<220> FEATURE:
<223> OTHER INFORMATION: Synthetic

<400> SEQUENCE: 288
ctgactgcct gggccagagg                                                    20

<210> SEQ ID NO: 289
<211> LENGTH: 20
<212> TYPE: DNA
<213> ORGANISM: Artificial Sequence
<220> FEATURE:
<223> OTHER INFORMATION: Synthetic

<400> SEQUENCE: 289
tacaacatgg gctacaggct                                                    20

<210> SEQ ID NO: 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
agccactgga gctgccctc                                                     20

<210> SEQ ID NO: 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
ctggagctgc ccctcagctt                                                    20

<210> SEQ ID NO: 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
ttggcccggc ggttcagcca                                                    20

<210> SEQ ID NO: 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
ttggccagga gggcattggc                                                    20

<210> SEQ ID NO: 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
ccggcggttc agccactgga                                                    20
```

<210> SEQ ID NO: 295
<211> LENGTH: 20
<212> TYPE: DNA
<213> ORGANISM: Artificial Sequence
<220> FEATURE:
<223> OTHER INFORMATION: Synthetic

<400> SEQUENCE: 295
ctcagctcca cgccattggc                                           20

<210> SEQ ID NO: 296
<211> LENGTH: 20
<212> TYPE: DNA
<213> ORGANISM: Artificial Sequence
<220> FEATURE:
<223> OTHER INFORMATION: Synthetic

<400> SEQUENCE: 296
caggagggca ttggcccggc                                           20

<210> SEQ ID NO: 297
<211> LENGTH: 20
<212> TYPE: DNA
<213> ORGANISM: Artificial Sequence
<220> FEATURE:
<223> OTHER INFORMATION: Synthetic

<400> SEQUENCE: 297
ctccacgcca ttggccagga                                           20

<210> SEQ ID NO: 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
accagctggt tatctctcag                                           20

<210> SEQ ID NO: 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
ctggttatct ctcagctcca                                           20

<210> SEQ ID NO: 300
<211> LENGTH: 20
<212> TYPE: DNA
<213> ORGANISM: Artificial Sequence
<220> FEATURE:
<223> OTHER INFORMATION: Synthetic

<400> SEQUENCE: 300
ccctctgatg gcaccaccag                                           20

<210> SEQ ID NO: 301
<211> LENGTH: 20
<212> TYPE: DNA
<213> ORGANISM: Artificial Sequence
<220> FEATURE:
<223> OTHER INFORMATION: Synthetic

<400> SEQUENCE: 301
tgatggcacc accagctggt                                                        20

<210> SEQ ID NO: 302
<211> LENGTH: 20
<212> TYPE: DNA
<213> ORGANISM: Artificial Sequence
<220> FEATURE:
<223> OTHER INFORMATION: Synthetic

<400> SEQUENCE: 302
tagatgaggt acaggccctc                                                        20

<210> SEQ ID NO: 303
<211> LENGTH: 20
<212> TYPE: DNA
<213> ORGANISM: Artificial Sequence
<220> FEATURE:
<223> OTHER INFORMATION: Synthetic

<400> SEQUENCE: 303
aagaggacct gggagtagat                                                        20

<210> SEQ ID NO: 304
<211> LENGTH: 20
<212> TYPE: DNA
<213> ORGANISM: Artificial Sequence
<220> FEATURE:
<223> OTHER INFORMATION: Synthetic

<400> SEQUENCE: 304
gaggtacagg ccctctgatg                                                        20

<210> SEQ ID NO: 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
cagccttggc ccttgaagag                                                        20

<210> SEQ ID NO: 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
gacctgggag tagatgaggt                                                        20

<210> SEQ ID NO: 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
ttggcccttg aagaggacct                                                        20

<210> SEQ ID NO: 308

-continued

<211> LENGTH: 20
<212> TYPE: DNA
<213> ORGANISM: Artificial Sequence
<220> FEATURE:
<223> OTHER INFORMATION: Synthetic

<400> SEQUENCE: 308
tggtgtgggt gaggagcaca                                                  20

<210> SEQ ID NO: 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
cggcgatgcg gctgatggtg                                                  20

<210> SEQ ID NO: 310
<211> LENGTH: 20
<212> TYPE: DNA
<213> ORGANISM: Artificial Sequence
<220> FEATURE:
<223> OTHER INFORMATION: Synthetic

<400> SEQUENCE: 310
tgggtgagga gcacatgggt                                                  20

<210> SEQ ID NO: 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
tggtctggta ggagacggcg                                                  20

<210> SEQ ID NO: 312
<211> LENGTH: 20
<212> TYPE: DNA
<213> ORGANISM: Artificial Sequence
<220> FEATURE:
<223> OTHER INFORMATION: Synthetic

<400> SEQUENCE: 312
atgcggctga tggtgtgggt                                                  20

<210> SEQ ID NO: 313
<211> LENGTH: 20
<212> TYPE: DNA
<213> ORGANISM: Artificial Sequence
<220> FEATURE:
<223> OTHER INFORMATION: Synthetic

<400> SEQUENCE: 313
agaggaggtt gaccttggtc                                                  20

<210> SEQ ID NO: 314
<211> LENGTH: 20
<212> TYPE: DNA
<213> ORGANISM: Artificial Sequence
<220> FEATURE:
<223> OTHER INFORMATION: Synthetic

<400> SEQUENCE: 314 tggtaggagac ggcgatgcg    20

<210> SEQ ID NO: 315
<211> LENGTH: 20
<212> TYPE: DNA
<213> ORGANISM: Artificial Sequence
<220> FEATURE:
<223> OTHER INFORMATION: Synthetic

<400> SEQUENCE: 315
aggttgacct tggtctggta    20

<210> SEQ ID NO: 316
<211> LENGTH: 20
<212> TYPE: DNA
<213> ORGANISM: Artificial Sequence
<220> FEATURE:
<223> OTHER INFORMATION: Synthetic

<400> SEQUENCE: 316
ggctcttgat ggcagagagg    20

<210> SEQ ID NO: 317
<211> LENGTH: 20
<212> TYPE: DNA
<213> ORGANISM: Artificial Sequence
<220> FEATURE:
<223> OTHER INFORMATION: Synthetic

<400> SEQUENCE: 317 tcataccaggg cttggcctc    20

<210> SEQ ID NO: 318
<211> LENGTH: 20
<212> TYPE: DNA
<213> ORGANISM: Artificial Sequence
<220> FEATURE:
<223> OTHER INFORMATION: Synthetic

<400> SEQUENCE: 318
ttgatggcag agaggaggtt    20

<210> SEQ ID NO: 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
agctggaaga cccctcccag    20

<210> SEQ ID NO: 320
<211> LENGTH: 20
<212> TYPE: DNA
<213> ORGANISM: Artificial Sequence
<220> FEATURE:
<223> OTHER INFORMATION: Synthetic

<400> SEQUENCE: 320
atagatgggc tcataccagg    20

<210> SEQ ID NO: 321
<211> LENGTH: 20
<212> TYPE: DNA

<213> ORGANISM: Artificial Sequence
<220> FEATURE:
<223> OTHER INFORMATION: Synthetic

<400> SEQUENCE: 321
cggtcaccct tctccagctg                                             20

<210> SEQ ID NO: 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
gaagacccct cccagataga                                             20

<210> SEQ ID NO: 323
<211> LENGTH: 20
<212> TYPE: DNA
<213> ORGANISM: Artificial Sequence
<220> FEATURE:
<223> OTHER INFORMATION: Synthetic

<400> SEQUENCE: 323
acccttctcc agctggaaga                                             20

<210> SEQ ID NO: 324
<211> LENGTH: 20
<212> TYPE: DNA
<213> ORGANISM: Artificial Sequence
<220> FEATURE:
<223> OTHER INFORMATION: Synthetic

<400> SEQUENCE: 324
tcggcaaagt cgagatagtc                                             20

<210> SEQ ID NO: 325
<211> LENGTH: 20
<212> TYPE: DNA
<213> ORGANISM: Artificial Sequence
<220> FEATURE:
<223> OTHER INFORMATION: Synthetic

<400> SEQUENCE: 325
gggccgattg atctcagcgc                                             20

<210> SEQ ID NO: 326
<211> LENGTH: 20
<212> TYPE: DNA
<213> ORGANISM: Artificial Sequence
<220> FEATURE:
<223> OTHER INFORMATION: Synthetic

<400> SEQUENCE: 326
tagacctgcc cagactcggc                                             20

<210> SEQ ID NO: 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
aaagtcgaga tagtcgggcc                                             20

<210> SEQ ID NO: 328
<211> LENGTH: 20
<212> TYPE: DNA
<213> ORGANISM: Artificial Sequence
<220> FEATURE:
<223> OTHER INFORMATION: Synthetic

<400> SEQUENCE: 328
gcaatgatcc caaagtagac                                                    20

<210> SEQ ID NO: 329
<211> LENGTH: 20
<212> TYPE: DNA
<213> ORGANISM: Artificial Sequence
<220> FEATURE:
<223> OTHER INFORMATION: Synthetic

<400> SEQUENCE: 329
ctgcccagac tcggcaaagt                                                    20

<210> SEQ ID NO: 330
<211> LENGTH: 20
<212> TYPE: DNA
<213> ORGANISM: Artificial Sequence
<220> FEATURE:
<223> OTHER INFORMATION: Synthetic

<400> SEQUENCE: 330
cgtcctcctc acagggcaat                                                    20

<210> SEQ ID NO: 331
<211> LENGTH: 20
<212> TYPE: DNA
<213> ORGANISM: Artificial Sequence
<220> FEATURE:
<223> OTHER INFORMATION: Synthetic

<400> SEQUENCE: 331
ggaaggttgg atgttcgtcc                                                    20

<210> SEQ ID NO: 332
<211> LENGTH: 20
<212> TYPE: DNA
<213> ORGANISM: Artificial Sequence
<220> FEATURE:
<223> OTHER INFORMATION: Synthetic

<400> SEQUENCE: 332
tcctcacagg gcaatgatcc                                                    20

<210> SEQ ID NO: 333
<211> LENGTH: 20
<212> TYPE: DNA
<213> ORGANISM: Artificial Sequence
<220> FEATURE:
<223> OTHER INFORMATION: Synthetic

<400> SEQUENCE: 333
gttgagggtg tctgaaggag                                                    20

<210> SEQ ID NO: 334
<211> LENGTH: 20
<212> TYPE: DNA
<213> ORGANISM: Artificial Sequence
<220> FEATURE:

<223> OTHER INFORMATION: Synthetic

<400> SEQUENCE: 334
gttggatgtt cgtcctcctc                                                  20

<210> SEQ ID NO: 335
<211> LENGTH: 20
<212> TYPE: DNA
<213> ORGANISM: Artificial Sequence
<220> FEATURE:
<223> OTHER INFORMATION: Synthetic

<400> SEQUENCE: 335
tttgagccag aagaggttga                                                  20

<210> SEQ ID NO: 336
<211> LENGTH: 20
<212> TYPE: DNA
<213> ORGANISM: Artificial Sequence
<220> FEATURE:
<223> OTHER INFORMATION: Synthetic

<400> SEQUENCE: 336
gaggcgtttg ggaaggttgg                                                  20

<210> SEQ ID NO: 337
<211> LENGTH: 20
<212> TYPE: DNA
<213> ORGANISM: Artificial Sequence
<220> FEATURE:
<223> OTHER INFORMATION: Synthetic

<400> SEQUENCE: 337
gcccccaatt ctcttttga                                                   20

<210> SEQ ID NO: 338
<211> LENGTH: 20
<212> TYPE: DNA
<213> ORGANISM: Artificial Sequence
<220> FEATURE:
<223> OTHER INFORMATION: Synthetic

<400> SEQUENCE: 338
gccagaagag gttgagggtg                                                  20

<210> SEQ ID NO: 339
<211> LENGTH: 20
<212> TYPE: DNA
<213> ORGANISM: Artificial Sequence
<220> FEATURE:
<223> OTHER INFORMATION: Synthetic

<400> SEQUENCE: 339
gggttccgac cctaagcccc                                                  20

<210> SEQ ID NO: 340
<211> LENGTH: 20
<212> TYPE: DNA
<213> ORGANISM: Artificial Sequence
<220> FEATURE:
<223> OTHER INFORMATION: Synthetic

<400> SEQUENCE: 340
caattctctt tttgagccag                                                  20

<210> SEQ ID NO: 341
<211> LENGTH: 20
<212> TYPE: DNA
<213> ORGANISM: Artificial Sequence
<220> FEATURE:
<223> OTHER INFORMATION: Synthetic

<400> SEQUENCE: 341
taaagttcta agcttgggtt                                              20

<210> SEQ ID NO: 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
ccgaccctaa gcccccaatt                                              20

<210> SEQ ID NO: 343
<211> LENGTH: 20
<212> TYPE: DNA
<213> ORGANISM: Artificial Sequence
<220> FEATURE:
<223> OTHER INFORMATION: Synthetic

<400> SEQUENCE: 343
ggtggtcttg ttgcttaaag                                              20

<210> SEQ ID NO: 344
<211> LENGTH: 20
<212> TYPE: DNA
<213> ORGANISM: Artificial Sequence
<220> FEATURE:
<223> OTHER INFORMATION: Synthetic

<400> SEQUENCE: 344
ttctaagctt gggttccgac                                              20

<210> SEQ ID NO: 345
<211> LENGTH: 20
<212> TYPE: DNA
<213> ORGANISM: Artificial Sequence
<220> FEATURE:
<223> OTHER INFORMATION: Synthetic

<400> SEQUENCE: 345
cccaggtttc gaagtggtgg                                              20

<210> SEQ ID NO: 346
<211> LENGTH: 20
<212> TYPE: DNA
<213> ORGANISM: Artificial Sequence
<220> FEATURE:
<223> OTHER INFORMATION: Synthetic

<400> SEQUENCE: 346
tcttgttgct taaagttcta                                              20

<210> SEQ ID NO: 347
<211> LENGTH: 20
<212> TYPE: DNA
<213> ORGANISM: Artificial Sequence
<220> FEATURE:
<223> OTHER INFORMATION: Synthetic -continued

<400> SEQUENCE: 347
cacacattcc tgaatcccag 20

<210> SEQ ID NO: 348
<211> LENGTH: 20
<212> TYPE: DNA
<213> ORGANISM: Artificial Sequence
<220> FEATURE:
<223> OTHER INFORMATION: Synthetic

<400> SEQUENCE: 348
gtttcgaagt ggtggtcttg 20

<210> SEQ ID NO: 349
<211> LENGTH: 20
<212> TYPE: DNA
<213> ORGANISM: Artificial Sequence
<220> FEATURE:
<223> OTHER INFORMATION: Synthetic

<400> SEQUENCE: 349
cttcactgtg caggccacac 20

<210> SEQ ID NO: 350
<211> LENGTH: 20
<212> TYPE: DNA
<213> ORGANISM: Artificial Sequence
<220> FEATURE:
<223> OTHER INFORMATION: Synthetic

<400> SEQUENCE: 350
attcctgaat cccaggtttc 20

<210> SEQ ID NO: 351
<211> LENGTH: 20
<212> TYPE: DNA
<213> ORGANISM: Artificial Sequence
<220> FEATURE:
<223> OTHER INFORMATION: Synthetic

<400> SEQUENCE: 351
tagtggttgc cagcacttca 20

<210> SEQ ID NO: 352
<211> LENGTH: 20
<212> TYPE: DNA
<213> ORGANISM: Artificial Sequence
<220> FEATURE:
<223> OTHER INFORMATION: Synthetic

<400> SEQUENCE: 352
cccagtttga attcttagtg 20

<210> SEQ ID NO: 353
<211> LENGTH: 20
<212> TYPE: DNA
<213> ORGANISM: Artificial Sequence
<220> FEATURE:
<223> OTHER INFORMATION: Synthetic

<400> SEQUENCE: 353
ctgtgcaggc cacacattcc 20

<210> SEQ ID NO: 354
<211> LENGTH: 20

<212> TYPE: DNA
<213> ORGANISM: Artificial Sequence
<220> FEATURE:
<223> OTHER INFORMATION: Synthetic

<400> SEQUENCE: 354
gtgagttctg gaggccccag 20

<210> SEQ ID NO: 355
<211> LENGTH: 20
<212> TYPE: DNA
<213> ORGANISM: Artificial Sequence
<220> FEATURE:
<223> OTHER INFORMATION: Synthetic

<400> SEQUENCE: 355
gttgccagca cttcactgtg 20

<210> SEQ ID NO: 356
<211> LENGTH: 20
<212> TYPE: DNA
<213> ORGANISM: Artificial Sequence
<220> FEATURE:
<223> OTHER INFORMATION: Synthetic

<400> SEQUENCE: 356
tttgaattct tagtggttgc 20

<210> SEQ ID NO: 357
<211> LENGTH: 20
<212> TYPE: DNA
<213> ORGANISM: Artificial Sequence
<220> FEATURE:
<223> OTHER INFORMATION: Synthetic

<400> SEQUENCE: 357
aagctgtagg ccccagtgag 20

<210> SEQ ID NO: 358
<211> LENGTH: 20
<212> TYPE: DNA
<213> ORGANISM: Artificial Sequence
<220> FEATURE:
<223> OTHER INFORMATION: Synthetic

<400> SEQUENCE: 358
ttctggaggc cccagtttga 20

<210> SEQ ID NO: 359
<211> LENGTH: 20
<212> TYPE: DNA
<213> ORGANISM: Artificial Sequence
<220> FEATURE:
<223> OTHER INFORMATION: Synthetic

<400> SEQUENCE: 359
agatgtcagg gatcaaagct 20

<210> SEQ ID NO: 360
<211> LENGTH: 20
<212> TYPE: DNA
<213> ORGANISM: Artificial Sequence
<220> FEATURE:
<223> OTHER INFORMATION: Synthetic

<400> SEQUENCE: 360
tggtctccag attccagatg 20

<210> SEQ ID NO: 361
<211> LENGTH: 20
<212> TYPE: DNA
<213> ORGANISM: Artificial Sequence
<220> FEATURE:
<223> OTHER INFORMATION: Synthetic

<400> SEQUENCE: 361
gtaggcccca gtgagttctg 20

<210> SEQ ID NO: 362
<211> LENGTH: 20
<212> TYPE: DNA
<213> ORGANISM: Artificial Sequence
<220> FEATURE:
<223> OTHER INFORMATION: Synthetic

<400> SEQUENCE: 362
gaaccaaagg ctccctggtc 20

<210> SEQ ID NO: 363
<211> LENGTH: 20
<212> TYPE: DNA
<213> ORGANISM: Artificial Sequence
<220> FEATURE:
<223> OTHER INFORMATION: Synthetic

<400> SEQUENCE: 363
tcagggatca aagctgtagg 20

<210> SEQ ID NO: 364
<211> LENGTH: 20
<212> TYPE: DNA
<213> ORGANISM: Artificial Sequence
<220> FEATURE:
<223> OTHER INFORMATION: Synthetic

<400> SEQUENCE: 364
tccagattcc agatgtcagg 20

<210> SEQ ID NO: 365
<211> LENGTH: 20
<212> TYPE: DNA
<213> ORGANISM: Artificial Sequence
<220> FEATURE:
<223> OTHER INFORMATION: Synthetic

<400> SEQUENCE: 365
gcagcattct ggccagaacc 20

<210> SEQ ID NO: 366
<211> LENGTH: 20
<212> TYPE: DNA
<213> ORGANISM: Artificial Sequence
<220> FEATURE:
<223> OTHER INFORMATION: Synthetic

<400> SEQUENCE: 366
gtcttctcaa gtcctgcagc 20

<210> SEQ ID NO: 367
<211> LENGTH: 20
<212> TYPE: DNA
<213> ORGANISM: Artificial Sequence

```
<220> FEATURE:
<223> OTHER INFORMATION: Synthetic

<400> SEQUENCE: 367
aaaggctccc tggtctccag                                              20

<210> SEQ ID NO: 368
<211> LENGTH: 20
<212> TYPE: DNA
<213> ORGANISM: Artificial Sequence
<220> FEATURE:
<223> OTHER INFORMATION: Synthetic

<400> SEQUENCE: 368
caatttctag gtgaggtctt                                              20

<210> SEQ ID NO: 369
<211> LENGTH: 20
<212> TYPE: DNA
<213> ORGANISM: Artificial Sequence
<220> FEATURE:
<223> OTHER INFORMATION: Synthetic

<400> SEQUENCE: 369
attctggcca gaaccaaagg                                              20

<210> SEQ ID NO: 370
<211> LENGTH: 20
<212> TYPE: DNA
<213> ORGANISM: Artificial Sequence
<220> FEATURE:
<223> OTHER INFORMATION: Synthetic

<400> SEQUENCE: 370
aaggtccact tgtgtcaatt                                              20

<210> SEQ ID NO: 371
<211> LENGTH: 20
<212> TYPE: DNA
<213> ORGANISM: Artificial Sequence
<220> FEATURE:
<223> OTHER INFORMATION: Synthetic

<400> SEQUENCE: 371
gagagaggaa ggcctaaggt                                              20

<210> SEQ ID NO: 372
<211> LENGTH: 20
<212> TYPE: DNA
<213> ORGANISM: Artificial Sequence
<220> FEATURE:
<223> OTHER INFORMATION: Synthetic

<400> SEQUENCE: 372
tctaggtgag gtcttctcaa                                              20

<210> SEQ ID NO: 373
<211> LENGTH: 20
<212> TYPE: DNA
<213> ORGANISM: Artificial Sequence
<220> FEATURE:
<223> OTHER INFORMATION: Synthetic

<400> SEQUENCE: 373
ccacttgtgt caatttctag                                              20
```

<210> SEQ ID NO: 374
<211> LENGTH: 20
<212> TYPE: DNA
<213> ORGANISM: Artificial Sequence
<220> FEATURE:
<223> OTHER INFORMATION: Synthetic

<400> SEQUENCE: 374
gtctggaaac atctggagag                    20

<210> SEQ ID NO: 375
<211> LENGTH: 20
<212> TYPE: DNA
<213> ORGANISM: Artificial Sequence
<220> FEATURE:
<223> OTHER INFORMATION: Synthetic

<400> SEQUENCE: 375
ccgtgtctca aggaagtctg                    20

<210> SEQ ID NO: 376
<211> LENGTH: 20
<212> TYPE: DNA
<213> ORGANISM: Artificial Sequence
<220> FEATURE:
<223> OTHER INFORMATION: Synthetic

<400> SEQUENCE: 376
aggaaggcct aaggtccact                    20

<210> SEQ ID NO: 377
<211> LENGTH: 20
<212> TYPE: DNA
<213> ORGANISM: Artificial Sequence
<220> FEATURE:
<223> OTHER INFORMATION: Synthetic

<400> SEQUENCE: 377
gagggagctg gctccatggg                    20

<210> SEQ ID NO: 378
<211> LENGTH: 20
<212> TYPE: DNA
<213> ORGANISM: Artificial Sequence
<220> FEATURE:
<223> OTHER INFORMATION: Synthetic

<400> SEQUENCE: 378
gaaacatctg gagagaggaa                    20

<210> SEQ ID NO: 379
<211> LENGTH: 20
<212> TYPE: DNA
<213> ORGANISM: Artificial Sequence
<220> FEATURE:
<223> OTHER INFORMATION: Synthetic

<400> SEQUENCE: 379
gtgcaaacat aaatagaggg                    20

<210> SEQ ID NO: 380
<211> LENGTH: 20
<212> TYPE: DNA
<213> ORGANISM: Artificial Sequence
<220> FEATURE:
<223> OTHER INFORMATION: Synthetic

<400> SEQUENCE: 380
tctcaaggaa gtctggaaac                                                                 20

<210> SEQ ID NO: 381
<211> LENGTH: 20
<212> TYPE: DNA
<213> ORGANISM: Artificial Sequence
<220> FEATURE:
<223> OTHER INFORMATION: Synthetic

<400> SEQUENCE: 381
aataaataat cacaagtgca                                                                 20

<210> SEQ ID NO: 382
<211> LENGTH: 20
<212> TYPE: DNA
<213> ORGANISM: Artificial Sequence
<220> FEATURE:
<223> OTHER INFORMATION: Synthetic

<400> SEQUENCE: 382
gggctgggct ccgtgtctca                                                                 20

<210> SEQ ID NO: 383
<211> LENGTH: 20
<212> TYPE: DNA
<213> ORGANISM: Artificial Sequence
<220> FEATURE:
<223> OTHER INFORMATION: Synthetic

<400> SEQUENCE: 383
taccccggtc tcccaaataa                                                                 20

<210> SEQ ID NO: 384
<211> LENGTH: 20
<212> TYPE: DNA
<213> ORGANISM: Artificial Sequence
<220> FEATURE:
<223> OTHER INFORMATION: Synthetic

<400> SEQUENCE: 384
aacataaata gagggagctg                                                                 20

<210> SEQ ID NO: 385
<211> LENGTH: 20
<212> TYPE: DNA
<213> ORGANISM: Artificial Sequence
<220> FEATURE:
<223> OTHER INFORMATION: Synthetic

<400> SEQUENCE: 385
ttgggtcccc caggataccc                                                                 20

<210> SEQ ID NO: 386
<211> LENGTH: 20
<212> TYPE: DNA
<213> ORGANISM: Artificial Sequence
<220> FEATURE:
<223> OTHER INFORMATION: Synthetic

<400> SEQUENCE: 386
ataatcacaa gtgcaaacat                                                                 20

<210> SEQ ID NO: 387

```
<211> LENGTH: 20
<212> TYPE: DNA
<213> ORGANISM: Artificial Sequence
<220> FEATURE:
<223> OTHER INFORMATION: Synthetic

<400> SEQUENCE: 387
aaggcagctc ctacattggg                                              20

<210> SEQ ID NO: 388
<211> LENGTH: 20
<212> TYPE: DNA
<213> ORGANISM: Artificial Sequence
<220> FEATURE:
<223> OTHER INFORMATION: Synthetic

<400> SEQUENCE: 388
cggtctccca aataaataca                                              20

<210> SEQ ID NO: 389
<211> LENGTH: 20
<212> TYPE: DNA
<213> ORGANISM: Artificial Sequence
<220> FEATURE:
<223> OTHER INFORMATION: Synthetic

<400> SEQUENCE: 389
aaacatgtct gagccaaggc                                              20

<210> SEQ ID NO: 390
<211> LENGTH: 20
<212> TYPE: DNA
<213> ORGANISM: Artificial Sequence
<220> FEATURE:
<223> OTHER INFORMATION: Synthetic

<400> SEQUENCE: 390
tcccccagga taccccggtc                                              20

<210> SEQ ID NO: 391
<211> LENGTH: 20
<212> TYPE: DNA
<213> ORGANISM: Artificial Sequence
<220> FEATURE:
<223> OTHER INFORMATION: Synthetic

<400> SEQUENCE: 391
agctcctaca ttgggtcccc                                              20

<210> SEQ ID NO: 392
<211> LENGTH: 20
<212> TYPE: DNA
<213> ORGANISM: Artificial Sequence
<220> FEATURE:
<223> OTHER INFORMATION: Synthetic

<400> SEQUENCE: 392
tgtctgagcc aaggcagctc                                              20

<210> SEQ ID NO: 393
<211> LENGTH: 20
<212> TYPE: DNA
<213> ORGANISM: Artificial Sequence
<220> FEATURE:
<223> OTHER INFORMATION: Synthetic

<400> SEQUENCE: 393
```
cagcctattg ttcagctccg                                               20

<210> SEQ ID NO: 394
<211> LENGTH: 20
<212> TYPE: DNA
<213> ORGANISM: Artificial Sequence
<220> FEATURE:
<223> OTHER INFORMATION: Synthetic

<400> SEQUENCE: 394
agaaggcaca gaggccaggg                                               20

<210> SEQ ID NO: 395
<211> LENGTH: 20
<212> TYPE: DNA
<213> ORGANISM: Artificial Sequence
<220> FEATURE:
<223> OTHER INFORMATION: Synthetic

<400> SEQUENCE: 395
ttttcacgga aaacatgtct                                               20

<210> SEQ ID NO: 396
<211> LENGTH: 20
<212> TYPE: DNA
<213> ORGANISM: Artificial Sequence
<220> FEATURE:
<223> OTHER INFORMATION: Synthetic

<400> SEQUENCE: 396
tattgttcag ctccgttttc                                               20

<210> SEQ ID NO: 397
<211> LENGTH: 20
<212> TYPE: DNA
<213> ORGANISM: Artificial Sequence
<220> FEATURE:
<223> OTHER INFORMATION: Synthetic

<400> SEQUENCE: 397
aaaaacataa tcaaaagaag                                               20

<210> SEQ ID NO: 398
<211> LENGTH: 20
<212> TYPE: DNA
<213> ORGANISM: Artificial Sequence
<220> FEATURE:
<223> OTHER INFORMATION: Synthetic

<400> SEQUENCE: 398
cagataaata ttttaaaaaa                                               20

<210> SEQ ID NO: 399
<211> LENGTH: 20
<212> TYPE: DNA
<213> ORGANISM: Artificial Sequence
<220> FEATURE:
<223> OTHER INFORMATION: Synthetic

<400> SEQUENCE: 399
tacatgggaa cagcctattg                                               20

<210> SEQ ID NO: 400
<211> LENGTH: 20
<212> TYPE: DNA

<213> ORGANISM: Artificial Sequence
<220> FEATURE:
<223> OTHER INFORMATION: Synthetic

<400> SEQUENCE: 400
tttagacaac ttaatcagat                     20

<210> SEQ ID NO: 401
<211> LENGTH: 20
<212> TYPE: DNA
<213> ORGANISM: Artificial Sequence
<220> FEATURE:
<223> OTHER INFORMATION: Synthetic

<400> SEQUENCE: 401
cataatcaaa agaaggcaca                     20

<210> SEQ ID NO: 402
<211> LENGTH: 20
<212> TYPE: DNA
<213> ORGANISM: Artificial Sequence
<220> FEATURE:
<223> OTHER INFORMATION: Synthetic

<400> SEQUENCE: 402
accaaatcag cattgtttag                     20

<210> SEQ ID NO: 403
<211> LENGTH: 20
<212> TYPE: DNA
<213> ORGANISM: Artificial Sequence
<220> FEATURE:
<223> OTHER INFORMATION: Synthetic

<400> SEQUENCE: 403
aaatatttta aaaacataa                      20

<210> SEQ ID NO: 404
<211> LENGTH: 20
<212> TYPE: DNA
<213> ORGANISM: Artificial Sequence
<220> FEATURE:
<223> OTHER INFORMATION: Synthetic

<400> SEQUENCE: 404
gagtgacagt tggtcaccaa                     20

<210> SEQ ID NO: 405
<211> LENGTH: 20
<212> TYPE: DNA
<213> ORGANISM: Artificial Sequence
<220> FEATURE:
<223> OTHER INFORMATION: Synthetic

<400> SEQUENCE: 405 acaacttaatc agataaata                     20

<210> SEQ ID NO: 406
<211> LENGTH: 20
<212> TYPE: DNA
<213> ORGANISM: Artificial Sequence
<220> FEATURE:
<223> OTHER INFORMATION: Synthetic

<400> SEQUENCE: 406
cagaggctca gcaatgagtg                     20

<210> SEQ ID NO: 407
<211> LENGTH: 20
<212> TYPE: DNA
<213> ORGANISM: Artificial Sequence
<220> FEATURE:
<223> OTHER INFORMATION: Synthetic

<400> SEQUENCE: 407
atcagcattg tttagacaac                                                     20

<210> SEQ ID NO: 408
<211> LENGTH: 20
<212> TYPE: DNA
<213> ORGANISM: Artificial Sequence
<220> FEATURE:
<223> OTHER INFORMATION: Synthetic

<400> SEQUENCE: 408
agggcgatta cagacacaac                                                     20

<210> SEQ ID NO: 409
<211> LENGTH: 20
<212> TYPE: DNA
<213> ORGANISM: Artificial Sequence
<220> FEATURE:
<223> OTHER INFORMATION: Synthetic

<400> SEQUENCE: 409
acagttggtc accaaatcag                                                     20

<210> SEQ ID NO: 410
<211> LENGTH: 20
<212> TYPE: DNA
<213> ORGANISM: Artificial Sequence
<220> FEATURE:
<223> OTHER INFORMATION: Synthetic

<400> SEQUENCE: 410
tcgccactga atagtagggc                                                     20

<210> SEQ ID NO: 411
<211> LENGTH: 20
<212> TYPE: DNA
<213> ORGANISM: Artificial Sequence
<220> FEATURE:
<223> OTHER INFORMATION: Synthetic

<400> SEQUENCE: 411
gctcagcaat gagtgacagt                                                     20

<210> SEQ ID NO: 412
<211> LENGTH: 20
<212> TYPE: DNA
<213> ORGANISM: Artificial Sequence
<220> FEATURE:
<223> OTHER INFORMATION: Synthetic

<400> SEQUENCE: 412
agcaaacttt atttctcgcc                                                     20

<210> SEQ ID NO: 413
<211> LENGTH: 20
<212> TYPE: DNA
<213> ORGANISM: Artificial Sequence
<220> FEATURE:

<223> OTHER INFORMATION: Synthetic

<400> SEQUENCE: 413
gattacagac acaactcccc                                                        20

<210> SEQ ID NO: 414
<211> LENGTH: 20
<212> TYPE: DNA
<213> ORGANISM: Artificial Sequence
<220> FEATURE:
<223> OTHER INFORMATION: Synthetic

<400> SEQUENCE: 414
actgaatagt agggcgatta                                                        20

<210> SEQ ID NO: 415
<211> LENGTH: 20
<212> TYPE: DNA
<213> ORGANISM: Artificial Sequence
<220> FEATURE:
<223> OTHER INFORMATION: Synthetic

<400> SEQUENCE: 415
actttatttc tcgccactga                                                        20

<210> SEQ ID NO: 416
<211> LENGTH: 20
<212> TYPE: DNA
<213> ORGANISM: Artificial Sequence
<220> FEATURE:
<223> OTHER INFORMATION: Synthetic

<400> SEQUENCE: 416
gctgtccttg ctgagggagc                                                        20

<210> SEQ ID NO: 417
<211> LENGTH: 20
<212> TYPE: DNA
<213> ORGANISM: Artificial Sequence
<220> FEATURE:
<223> OTHER INFORMATION: Synthetic

<400> SEQUENCE: 417
cttagctggt cctctgctgt                                                        20

<210> SEQ ID NO: 418
<211> LENGTH: 20
<212> TYPE: DNA
<213> ORGANISM: Artificial Sequence
<220> FEATURE:
<223> OTHER INFORMATION: Synthetic

<400> SEQUENCE: 418
gttgcttctc tccctcttag                                                        20

<210> SEQ ID NO: 419
<211> LENGTH: 20
<212> TYPE: DNA
<213> ORGANISM: Artificial Sequence
<220> FEATURE:
<223> OTHER INFORMATION: Synthetic

<400> SEQUENCE: 419
tggcgtctga gggttgtttt                                                        20

```
<210> SEQ ID NO: 420
<211> LENGTH: 20
<212> TYPE: DNA
<213> ORGANISM: Artificial Sequence
<220> FEATURE:
<223> OTHER INFORMATION: Synthetic

<400> SEQUENCE: 420
agagaacctg cctggcagct                                               20

<210> SEQ ID NO: 421
<211> LENGTH: 20
<212> TYPE: DNA
<213> ORGANISM: Artificial Sequence
<220> FEATURE:
<223> OTHER INFORMATION: Synthetic

<400> SEQUENCE: 421
cagtatgtga gaggaagaga                                               20

<210> SEQ ID NO: 422
<211> LENGTH: 20
<212> TYPE: DNA
<213> ORGANISM: Artificial Sequence
<220> FEATURE:
<223> OTHER INFORMATION: Synthetic

<400> SEQUENCE: 422
ggtgaagccg tgggtcagta                                               20

<210> SEQ ID NO: 423
<211> LENGTH: 20
<212> TYPE: DNA
<213> ORGANISM: Artificial Sequence
<220> FEATURE:
<223> OTHER INFORMATION: Synthetic

<400> SEQUENCE: 423
agtgctcatg gtgtcctttc                                               20

<210> SEQ ID NO: 424
<211> LENGTH: 20
<212> TYPE: DNA
<213> ORGANISM: Artificial Sequence
<220> FEATURE:
<223> OTHER INFORMATION: Synthetic

<400> SEQUENCE: 424
ccggatcatg ctttcagtgc                                               20

<210> SEQ ID NO: 425
<211> LENGTH: 20
<212> TYPE: DNA
<213> ORGANISM: Artificial Sequence
<220> FEATURE:
<223> OTHER INFORMATION: Synthetic

<400> SEQUENCE: 425
ggccagctcc acgtcccgga                                               20

<210> SEQ ID NO: 426
<211> LENGTH: 20
<212> TYPE: DNA
<213> ORGANISM: Artificial Sequence
<220> FEATURE:
<223> OTHER INFORMATION: Synthetic
```

-continued

<400> SEQUENCE: 426 ggccccctg tcttcttggg                                                  20

<210> SEQ ID NO: 427
<211> LENGTH: 20
<212> TYPE: DNA
<213> ORGANISM: Artificial Sequence
<220> FEATURE:
<223> OTHER INFORMATION: Synthetic

<400> SEQUENCE: 427
ggctgaggaa caagcaccgc                                                 20

<210> SEQ ID NO: 428
<211> LENGTH: 20
<212> TYPE: DNA
<213> ORGANISM: Artificial Sequence
<220> FEATURE:
<223> OTHER INFORMATION: Synthetic

<400> SEQUENCE: 428
tcaggaagga gaagaggctg                                                 20

<210> SEQ ID NO: 429
<211> LENGTH: 20
<212> TYPE: DNA
<213> ORGANISM: Artificial Sequence
<220> FEATURE:
<223> OTHER INFORMATION: Synthetic

<400> SEQUENCE: 429
tggcgcctgc cacgatcagg                                                 20

<210> SEQ ID NO: 430
<211> LENGTH: 20
<212> TYPE: DNA
<213> ORGANISM: Artificial Sequence
<220> FEATURE:
<223> OTHER INFORMATION: Synthetic

<400> SEQUENCE: 430
ggcagaagag cgtggtggcg                                                 20

<210> SEQ ID NO: 431
<211> LENGTH: 20
<212> TYPE: DNA
<213> ORGANISM: Artificial Sequence
<220> FEATURE:
<223> OTHER INFORMATION: Synthetic

<400> SEQUENCE: 431
ctccaaagtg cagcaggcag                                                 20

<210> SEQ ID NO: 432
<211> LENGTH: 20
<212> TYPE: DNA
<213> ORGANISM: Artificial Sequence
<220> FEATURE:
<223> OTHER INFORMATION: Synthetic

<400> SEQUENCE: 432
gctgattaga gagaggtccc                                                 20

<210> SEQ ID NO: 433
<211> LENGTH: 20

<212> TYPE: DNA
<213> ORGANISM: Artificial Sequence
<220> FEATURE:
<223> OTHER INFORMATION: Synthetic

<400> SEQUENCE: 433
tgcctgggcc agagggctga                                                20

<210> SEQ ID NO: 434
<211> LENGTH: 20
<212> TYPE: DNA
<213> ORGANISM: Artificial Sequence
<220> FEATURE:
<223> OTHER INFORMATION: Synthetic

<400> SEQUENCE: 434
gctgcccctc agcttgaggg                                                20

<210> SEQ ID NO: 435
<211> LENGTH: 20
<212> TYPE: DNA
<213> ORGANISM: Artificial Sequence
<220> FEATURE:
<223> OTHER INFORMATION: Synthetic

<400> SEQUENCE: 435
ggttcagcca ctggagctgc                                                20

<210> SEQ ID NO: 436
<211> LENGTH: 20
<212> TYPE: DNA
<213> ORGANISM: Artificial Sequence
<220> FEATURE:
<223> OTHER INFORMATION: Synthetic

<400> SEQUENCE: 436
gggcattggc ccggcggttc                                                20

<210> SEQ ID NO: 437
<211> LENGTH: 20
<212> TYPE: DNA
<213> ORGANISM: Artificial Sequence
<220> FEATURE:
<223> OTHER INFORMATION: Synthetic

<400> SEQUENCE: 437
cgccattggc caggagggca                                                20

<210> SEQ ID NO: 438
<211> LENGTH: 20
<212> TYPE: DNA
<213> ORGANISM: Artificial Sequence
<220> FEATURE:
<223> OTHER INFORMATION: Synthetic

<400> SEQUENCE: 438
tatctctcag ctccacgcca                                                20

<210> SEQ ID NO: 439
<211> LENGTH: 20
<212> TYPE: DNA
<213> ORGANISM: Artificial Sequence
<220> FEATURE:
<223> OTHER INFORMATION: Synthetic

<400> SEQUENCE: 439
gcaccaccag ctggttatct 20

<210> SEQ ID NO: 440
<211> LENGTH: 20
<212> TYPE: DNA
<213> ORGANISM: Artificial Sequence
<220> FEATURE:
<223> OTHER INFORMATION: Synthetic

<400> SEQUENCE: 440
acaggccctc tgatggcacc 20

<210> SEQ ID NO: 441
<211> LENGTH: 20
<212> TYPE: DNA
<213> ORGANISM: Artificial Sequence
<220> FEATURE:
<223> OTHER INFORMATION: Synthetic

<400> SEQUENCE: 441
gggagtagat gaggtacagg 20

<210> SEQ ID NO: 442
<211> LENGTH: 20
<212> TYPE: DNA
<213> ORGANISM: Artificial Sequence
<220> FEATURE:
<223> OTHER INFORMATION: Synthetic

<400> SEQUENCE: 442
ccttgaagag gacctgggag 20

<210> SEQ ID NO: 443
<211> LENGTH: 20
<212> TYPE: DNA
<213> ORGANISM: Artificial Sequence
<220> FEATURE:
<223> OTHER INFORMATION: Synthetic

<400> SEQUENCE: 443
gaggagcaca tgggtggagg 20

<210> SEQ ID NO: 444
<211> LENGTH: 20
<212> TYPE: DNA
<213> ORGANISM: Artificial Sequence
<220> FEATURE:
<223> OTHER INFORMATION: Synthetic

<400> SEQUENCE: 444
gctgatggtg tgggtgagga 20

<210> SEQ ID NO: 445
<211> LENGTH: 20
<212> TYPE: DNA
<213> ORGANISM: Artificial Sequence
<220> FEATURE:
<223> OTHER INFORMATION: Synthetic

<400> SEQUENCE: 445
ggagacggcg atgcggctga 20

<210> SEQ ID NO: 446
<211> LENGTH: 20
<212> TYPE: DNA
<213> ORGANISM: Artificial Sequence
<220> FEATURE:
<223> OTHER INFORMATION: Synthetic

<400> SEQUENCE: 446
gaccttggtc tggtaggaga                                       20

<210> SEQ ID NO: 447
<211> LENGTH: 20
<212> TYPE: DNA
<213> ORGANISM: Artificial Sequence
<220> FEATURE:
<223> OTHER INFORMATION: Synthetic

<400> SEQUENCE: 447
ggcagagagg aggttgacct                                       20

<210> SEQ ID NO: 448
<211> LENGTH: 20
<212> TYPE: DNA
<213> ORGANISM: Artificial Sequence
<220> FEATURE:
<223> OTHER INFORMATION: Synthetic

<400> SEQUENCE: 448
tgggctcata ccagggcttg                                       20

<210> SEQ ID NO: 449
<211> LENGTH: 20
<212> TYPE: DNA
<213> ORGANISM: Artificial Sequence
<220> FEATURE:
<223> OTHER INFORMATION: Synthetic

<400> SEQUENCE: 449
cccctcccag atagatgggc                                       20

<210> SEQ ID NO: 450
<211> LENGTH: 20
<212> TYPE: DNA
<213> ORGANISM: Artificial Sequence
<220> FEATURE:
<223> OTHER INFORMATION: Synthetic

<400> SEQUENCE: 450
tgagtcggtc acccttctcc                                       20

<210> SEQ ID NO: 451
<211> LENGTH: 20
<212> TYPE: DNA
<213> ORGANISM: Artificial Sequence
<220> FEATURE:
<223> OTHER INFORMATION: Synthetic

<400> SEQUENCE: 451
gattgatctc agcgctgagt                                       20

<210> SEQ ID NO: 452
<211> LENGTH: 20
<212> TYPE: DNA
<213> ORGANISM: Artificial Sequence
<220> FEATURE:
<223> OTHER INFORMATION: Synthetic

<400> SEQUENCE: 452
cgagatagtc gggccgattg                                       20

<210> SEQ ID NO: 453
<211> LENGTH: 20
<212> TYPE: DNA
<213> ORGANISM: Artificial Sequence
<220> FEATURE:
<223> OTHER INFORMATION: Synthetic

<400> SEQUENCE: 453
caaagtagac ctgcccagac                                                     20

<210> SEQ ID NO: 454
<211> LENGTH: 20
<212> TYPE: DNA
<213> ORGANISM: Artificial Sequence
<220> FEATURE:
<223> OTHER INFORMATION: Synthetic

<400> SEQUENCE: 454
acagggcaat gatcccaaag                                                     20

<210> SEQ ID NO: 455
<211> LENGTH: 20
<212> TYPE: DNA
<213> ORGANISM: Artificial Sequence
<220> FEATURE:
<223> OTHER INFORMATION: Synthetic

<400> SEQUENCE: 455
atgttcgtcc tcctcacagg                                                     20

<210> SEQ ID NO: 456
<211> LENGTH: 20
<212> TYPE: DNA
<213> ORGANISM: Artificial Sequence
<220> FEATURE:
<223> OTHER INFORMATION: Synthetic

<400> SEQUENCE: 456
gtttgggaag gttggatgtt                                                     20

<210> SEQ ID NO: 457
<211> LENGTH: 20
<212> TYPE: DNA
<213> ORGANISM: Artificial Sequence
<220> FEATURE:
<223> OTHER INFORMATION: Synthetic

<400> SEQUENCE: 457
aagaggttga gggtgtctga                                                     20

<210> SEQ ID NO: 458
<211> LENGTH: 20
<212> TYPE: DNA
<213> ORGANISM: Artificial Sequence
<220> FEATURE:
<223> OTHER INFORMATION: Synthetic

<400> SEQUENCE: 458 ctcttttga gccagaagag                                                      20

<210> SEQ ID NO: 459
<211> LENGTH: 20
<212> TYPE: DNA
<213> ORGANISM: Artificial Sequence
<220> FEATURE:
<223> OTHER INFORMATION: Synthetic

<400> SEQUENCE: 459
cctaagcccc caattctctt         20

<210> SEQ ID NO: 460
<211> LENGTH: 20
<212> TYPE: DNA
<213> ORGANISM: Artificial Sequence
<220> FEATURE:
<223> OTHER INFORMATION: Synthetic

<400> SEQUENCE: 460
agcttgggtt ccgaccctaa         20

<210> SEQ ID NO: 461
<211> LENGTH: 20
<212> TYPE: DNA
<213> ORGANISM: Artificial Sequence
<220> FEATURE:
<223> OTHER INFORMATION: Synthetic

<400> SEQUENCE: 461
ttgcttaaag ttctaagctt         20

<210> SEQ ID NO: 462
<211> LENGTH: 20
<212> TYPE: DNA
<213> ORGANISM: Artificial Sequence
<220> FEATURE:
<223> OTHER INFORMATION: Synthetic

<400> SEQUENCE: 462
gaagtggtgg tcttgttgct         20

<210> SEQ ID NO: 463
<211> LENGTH: 20
<212> TYPE: DNA
<213> ORGANISM: Artificial Sequence
<220> FEATURE:
<223> OTHER INFORMATION: Synthetic

<400> SEQUENCE: 463
tgaatcccag gtttcgaagt         20

<210> SEQ ID NO: 464
<211> LENGTH: 20
<212> TYPE: DNA
<213> ORGANISM: Artificial Sequence
<220> FEATURE:
<223> OTHER INFORMATION: Synthetic

<400> SEQUENCE: 464
caggccacac attcctgaat         20

<210> SEQ ID NO: 465
<211> LENGTH: 20
<212> TYPE: DNA
<213> ORGANISM: Artificial Sequence
<220> FEATURE:
<223> OTHER INFORMATION: Synthetic

<400> SEQUENCE: 465
cagcacttca ctgtgcaggc         20

<210> SEQ ID NO: 466

```
<211> LENGTH: 20
<212> TYPE: DNA
<213> ORGANISM: Artificial Sequence
<220> FEATURE:
<223> OTHER INFORMATION: Synthetic

<400> SEQUENCE: 466
attcttagtg gttgccagca                                              20

<210> SEQ ID NO: 467
<211> LENGTH: 20
<212> TYPE: DNA
<213> ORGANISM: Artificial Sequence
<220> FEATURE:
<223> OTHER INFORMATION: Synthetic

<400> SEQUENCE: 467
gaggccccag tttgaattct                                              20

<210> SEQ ID NO: 468
<211> LENGTH: 20
<212> TYPE: DNA
<213> ORGANISM: Artificial Sequence
<220> FEATURE:
<223> OTHER INFORMATION: Synthetic

<400> SEQUENCE: 468
ccccagtgag ttctggaggc                                              20

<210> SEQ ID NO: 469
<211> LENGTH: 20
<212> TYPE: DNA
<213> ORGANISM: Artificial Sequence
<220> FEATURE:
<223> OTHER INFORMATION: Synthetic

<400> SEQUENCE: 469
gatcaaagct gtaggcccca                                              20

<210> SEQ ID NO: 470
<211> LENGTH: 20
<212> TYPE: DNA
<213> ORGANISM: Artificial Sequence
<220> FEATURE:
<223> OTHER INFORMATION: Synthetic

<400> SEQUENCE: 470
attccagatg tcagggatca                                              20

<210> SEQ ID NO: 471
<211> LENGTH: 20
<212> TYPE: DNA
<213> ORGANISM: Artificial Sequence
<220> FEATURE:
<223> OTHER INFORMATION: Synthetic

<400> SEQUENCE: 471
ctccctggtc tccagattcc                                              20

<210> SEQ ID NO: 472
<211> LENGTH: 20
<212> TYPE: DNA
<213> ORGANISM: Artificial Sequence
<220> FEATURE:
<223> OTHER INFORMATION: Synthetic

<400> SEQUENCE: 472
```
ggccagaacc aaaggctccc                                                    20

<210> SEQ ID NO: 473
<211> LENGTH: 20
<212> TYPE: DNA
<213> ORGANISM: Artificial Sequence
<220> FEATURE:
<223> OTHER INFORMATION: Synthetic

<400> SEQUENCE: 473
gtcctgcagc attctggcca                                                    20

<210> SEQ ID NO: 474
<211> LENGTH: 20
<212> TYPE: DNA
<213> ORGANISM: Artificial Sequence
<220> FEATURE:
<223> OTHER INFORMATION: Synthetic

<400> SEQUENCE: 474
gtgaggtctt ctcaagtcct                                                    20

<210> SEQ ID NO: 475
<211> LENGTH: 20
<212> TYPE: DNA
<213> ORGANISM: Artificial Sequence
<220> FEATURE:
<223> OTHER INFORMATION: Synthetic

<400> SEQUENCE: 475
tgtgtcaatt tctaggtgag                                                    20

<210> SEQ ID NO: 476
<211> LENGTH: 20
<212> TYPE: DNA
<213> ORGANISM: Artificial Sequence
<220> FEATURE:
<223> OTHER INFORMATION: Synthetic

<400> SEQUENCE: 476
ggcctaaggt ccacttgtgt                                                    20

<210> SEQ ID NO: 477
<211> LENGTH: 20
<212> TYPE: DNA
<213> ORGANISM: Artificial Sequence
<220> FEATURE:
<223> OTHER INFORMATION: Synthetic

<400> SEQUENCE: 477
atctggagag aggaaggcct                                                    20

<210> SEQ ID NO: 478
<211> LENGTH: 20
<212> TYPE: DNA
<213> ORGANISM: Artificial Sequence
<220> FEATURE:
<223> OTHER INFORMATION: Synthetic

<400> SEQUENCE: 478
aggaagtctg gaaacatctg                                                    20

<210> SEQ ID NO: 479
<211> LENGTH: 20
<212> TYPE: DNA

```
<213> ORGANISM: Artificial Sequence
<220> FEATURE:
<223> OTHER INFORMATION: Synthetic

<400> SEQUENCE: 479
gggctccgtg tctcaaggaa                                              20

<210> SEQ ID NO: 480
<211> LENGTH: 20
<212> TYPE: DNA
<213> ORGANISM: Artificial Sequence
<220> FEATURE:
<223> OTHER INFORMATION: Synthetic

<400> SEQUENCE: 480
aaatagaggg agctggctcc                                              20

<210> SEQ ID NO: 481
<211> LENGTH: 20
<212> TYPE: DNA
<213> ORGANISM: Artificial Sequence
<220> FEATURE:
<223> OTHER INFORMATION: Synthetic

<400> SEQUENCE: 481
cacaagtgca aacataaata                                              20

<210> SEQ ID NO: 482
<211> LENGTH: 20
<212> TYPE: DNA
<213> ORGANISM: Artificial Sequence
<220> FEATURE:
<223> OTHER INFORMATION: Synthetic

<400> SEQUENCE: 482
tcccaaataa atacattcat                                              20

<210> SEQ ID NO: 483
<211> LENGTH: 20
<212> TYPE: DNA
<213> ORGANISM: Artificial Sequence
<220> FEATURE:
<223> OTHER INFORMATION: Synthetic

<400> SEQUENCE: 483
caggataccc cggtctccca                                              20

<210> SEQ ID NO: 484
<211> LENGTH: 20
<212> TYPE: DNA
<213> ORGANISM: Artificial Sequence
<220> FEATURE:
<223> OTHER INFORMATION: Synthetic

<400> SEQUENCE: 484
ctacattggg tcccccagga                                              20

<210> SEQ ID NO: 485
<211> LENGTH: 20
<212> TYPE: DNA
<213> ORGANISM: Artificial Sequence
<220> FEATURE:
<223> OTHER INFORMATION: Synthetic

<400> SEQUENCE: 485
gagccaaggc agctcctaca                                              20
```

<210> SEQ ID NO: 486
<211> LENGTH: 20
<212> TYPE: DNA
<213> ORGANISM: Artificial Sequence
<220> FEATURE:
<223> OTHER INFORMATION: Synthetic

<400> SEQUENCE: 486
acggaaaaca tgtctgagcc                                            20

<210> SEQ ID NO: 487
<211> LENGTH: 20
<212> TYPE: DNA
<213> ORGANISM: Artificial Sequence
<220> FEATURE:
<223> OTHER INFORMATION: Synthetic

<400> SEQUENCE: 487
ttcagctccg ttttcacgga                                            20

<210> SEQ ID NO: 488
<211> LENGTH: 20
<212> TYPE: DNA
<213> ORGANISM: Artificial Sequence
<220> FEATURE:
<223> OTHER INFORMATION: Synthetic

<400> SEQUENCE: 488
gggaacagcc tattgttcag                                            20

<210> SEQ ID NO: 489
<211> LENGTH: 20
<212> TYPE: DNA
<213> ORGANISM: Artificial Sequence
<220> FEATURE:
<223> OTHER INFORMATION: Synthetic

<400> SEQUENCE: 489 tcaaagaag gcacagaggc                                             20

<210> SEQ ID NO: 490
<211> LENGTH: 20
<212> TYPE: DNA
<213> ORGANISM: Artificial Sequence
<220> FEATURE:
<223> OTHER INFORMATION: Synthetic

<400> SEQUENCE: 490
ttttaaaaaa cataatcaaa                                            20

<210> SEQ ID NO: 491
<211> LENGTH: 20
<212> TYPE: DNA
<213> ORGANISM: Artificial Sequence
<220> FEATURE:
<223> OTHER INFORMATION: Synthetic

<400> SEQUENCE: 491
ttaatcagat aaatatttta                                            20

<210> SEQ ID NO: 492
<211> LENGTH: 20
<212> TYPE: DNA
<213> ORGANISM: Artificial Sequence
<220> FEATURE:

```
<223> OTHER INFORMATION: Synthetic

<400> SEQUENCE: 492
cattgtttag acaacttaat                                               20

<210> SEQ ID NO: 493
<211> LENGTH: 20
<212> TYPE: DNA
<213> ORGANISM: Artificial Sequence
<220> FEATURE:
<223> OTHER INFORMATION: Synthetic

<400> SEQUENCE: 493
tggtcaccaa atcagcattg                                               20

<210> SEQ ID NO: 494
<211> LENGTH: 20
<212> TYPE: DNA
<213> ORGANISM: Artificial Sequence
<220> FEATURE:
<223> OTHER INFORMATION: Synthetic

<400> SEQUENCE: 494
gcaatgagtg acagttggtc                                               20

<210> SEQ ID NO: 495
<211> LENGTH: 20
<212> TYPE: DNA
<213> ORGANISM: Artificial Sequence
<220> FEATURE:
<223> OTHER INFORMATION: Synthetic

<400> SEQUENCE: 495
gggagcagag gctcagcaat                                               20

<210> SEQ ID NO: 496
<211> LENGTH: 20
<212> TYPE: DNA
<213> ORGANISM: Artificial Sequence
<220> FEATURE:
<223> OTHER INFORMATION: Synthetic

<400> SEQUENCE: 496
atagtagggc gattacagac                                               20

<210> SEQ ID NO: 497
<211> LENGTH: 20
<212> TYPE: DNA
<213> ORGANISM: Artificial Sequence
<220> FEATURE:
<223> OTHER INFORMATION: Synthetic

<400> SEQUENCE: 497
atttctcgcc actgaatagt                                               20

<210> SEQ ID NO: 498
<211> LENGTH: 19
<212> TYPE: DNA
<213> ORGANISM: Artificial Sequence
<220> FEATURE:
<223> OTHER INFORMATION: Synthetic

<400> SEQUENCE: 498
ctgattagag agaggtccc                                                19
```

-continued

```
<210> SEQ ID NO: 499
<211> LENGTH: 18
<212> TYPE: DNA
<213> ORGANISM: Artificial Sequence
<220> FEATURE:
<223> OTHER INFORMATION: Synthetic

<400> SEQUENCE: 499
ctgattagag agaggtcc                                                       18

<210> SEQ ID NO: 500
<211> LENGTH: 20
<212> TYPE: DNA
<213> ORGANISM: Artificial Sequence
<220> FEATURE:
<223> OTHER INFORMATION: Synthetic

<400> SEQUENCE: 500
tgagtgtctt ctgtgtgcca                                                     20

<210> SEQ ID NO: 501
<211> LENGTH: 20
<212> TYPE: DNA
<213> ORGANISM: Artificial Sequence
<220> FEATURE:
<223> OTHER INFORMATION: Synthetic

<400> SEQUENCE: 501
gagtgtcttc tgtgtgccag                                                     20
```